US012806036B2

(12) United States Patent
Bergey

(10) Patent No.: US 12,806,036 B2
(45) Date of Patent: Nov. 24, 2026

(54) SACROILIAC, ANCHORING APPARATUS AND METHOD

(71) Applicant: Darren L. Bergey, Riverside, CA (US)

(72) Inventor: Darren L. Bergey, Riverside, CA (US)

( * ) Notice: Subject to any disclaimer, the term of this patent is extended or adjusted under 35 U.S.C. 154(b) by 120 days.

(21) Appl. No.: 18/222,441

(22) Filed: Jul. 15, 2023

(65) Prior Publication Data

US 2023/0390078 A1 Dec. 7, 2023

Related U.S. Application Data

(60) Continuation-in-part of application No. 16/838,827, filed on Apr. 2, 2020, now Pat. No. 11,701,238, (Continued)

(51) Int. Cl.
*A61F 2/44* (2006.01)
*A61F 2/28* (2006.01)
*A61F 2/30* (2006.01)

(52) U.S. Cl.
CPC ............ *A61F 2/447* (2013.01); *A61F 2/4425* (2013.01); *A61F 2/4455* (2013.01); (Continued)

(58) Field of Classification Search
CPC ................................ A61F 2/447; F16B 15/06
See application file for complete search history.

(56) References Cited

U.S. PATENT DOCUMENTS 1,635,923 A 7/1927 Bray
6,128,867 A 10/2000 MacKarvich
(Continued)

FOREIGN PATENT DOCUMENTS

CA 2758922 A1 10/2010
CN 1244105 A 2/2000
(Continued)

OTHER PUBLICATIONS

American Society for Reproductive Medicine, Adhesion Prevention: A Standard of Care, Surgical Techniques and Cost Effectiveness of Adhesion Prevention, Aug. 20, 2014.
(Continued)

*Primary Examiner* — Andrew Yang
(74) *Attorney, Agent, or Firm* — Morriss O'Bryant Compagni Cannon, PLLC

(57) ABSTRACT

A long-pitch, helical anchor (where long pitch is greater than length, itself greater than twice maximum diameter; and very long, extra-long, or hyper pitch exceeding several lengths of such anchor, typically at least 2 and usually 5 or 6) includes splines radially extending and helically progressing circumferentially around and axially along an elongate core. The center line or axis may be solid, all splines meeting near the center line. In other embodiments, the center line passes along the center of a lumen or channel of a hollow core, while the splines extend radially outward from, and axially along a length of the core. Installation may be from a posterior access or a lateral-posterior access, fixing two bones in two degrees of freedom, three degrees of freedom, or multiple anchors fixing the bones firmly in three degrees of freedom.

28 Claims, 30 Drawing Sheets

Related U.S. Application Data which is a continuation-in-part of application No. 16/263,405, filed on Jan. 31, 2019, now Pat. No. 10,898,345, which is a division of application No. 15/380,048, filed on Dec. 15, 2016, now Pat. No. 10,195,051, which is a division of application No. 15/001,502, filed on Jan. 20, 2016, now Pat. No. 9,539,110, which is a division of application No. 13/937,208, filed on Jul. 8, 2013, now Pat. No. 9,248,029, which is a continuation of application No. PCT/US2012/020560, filed on Jan. 6, 2012.

(60) Provisional application No. 61/430,296, filed on Jan. 6, 2011.

(52) U.S. Cl.

CPC ................. *A61F 2002/2817* (2013.01); *A61F 2002/2835* (2013.01); *A61F 2002/30187* (2013.01); *A61F 2002/3023* (2013.01); *A61F 2002/30578* (2013.01); *A61F 2002/30593* (2013.01); *A61F 2002/30607* (2013.01); *A61F 2002/30616* (2013.01); *A61F 2002/30782* (2013.01); *A61F 2002/30787* (2013.01); *A61F 2002/30841* (2013.01); *A61F 2002/30878* (2013.01); *A61F 2002/30904* (2013.01); *A61F 2/4465* (2013.01); *A61F 2310/00023* (2013.01); *A61F 2310/00161* (2013.01)

(56) References Cited

U.S. PATENT DOCUMENTS

| | | | | |
|---|---|---|---|---|
| 6,432,106 | B1 | 8/2002 | Fraser | |
| 8,092,505 | B2 * | 1/2012 | Sommers ............... | A61B 17/68 606/317 |
| 8,142,508 | B1 | 3/2012 | Bruffey et al. | |
| 8,167,949 | B2 | 5/2012 | Tyber et al. | |
| 8,267,997 | B2 | 9/2012 | Colleran | |
| 8,292,958 | B1 | 10/2012 | Bruffey et al. | |
| 8,353,938 | B2 | 1/2013 | Trieu et al. | |
| 8,366,774 | B1 | 2/2013 | Bruffey et al. | |
| 8,414,651 | B2 | 4/2013 | Tyber et al. | |
| 8,460,294 | B2 | 6/2013 | Overes | |
| 8,500,784 | B2 | 8/2013 | Hulliger et al. | |
| 8,506,534 | B2 | 8/2013 | Marnay et al. | |
| 8,523,916 | B2 | 9/2013 | Anderson et al. | |
| 8,568,483 | B2 | 10/2013 | Coppes et al. | |
| 8,579,903 | B2 | 11/2013 | Carl | |
| 8,579,978 | B2 | 11/2013 | Marnay et al. | |
| 8,591,513 | B2 | 11/2013 | Overes et al. | |
| 8,603,144 | B2 | 12/2013 | Kwak et al. | |
| 8,617,225 | B2 | 12/2013 | McShane et al. | |
| 8,623,057 | B2 | 1/2014 | Jahng et al. | |
| 8,641,734 | B2 | 2/2014 | Moumene et al. | |
| 8,641,766 | B2 | 2/2014 | Donner et al. | |
| 8,647,347 | B2 | 2/2014 | Runco et al. | |
| 8,663,229 | B2 | 3/2014 | Marnay et al. | |
| 8,663,292 | B2 | 3/2014 | Dec et al. | |
| 8,663,298 | B2 | 3/2014 | Keyer et al. | |
| 8,679,162 | B2 | 3/2014 | Strausbaugh et al. | |
| 8,685,066 | B2 | 4/2014 | Stad et al. | |
| 8,685,104 | B2 | 4/2014 | Lee et al. | |
| 8,696,703 | B2 | 4/2014 | Anspach, III et al. | |
| 8,721,692 | B2 | 5/2014 | Anderson et al. | |
| 8,734,490 | B2 | 5/2014 | Anderson et al. | |
| 8,740,946 | B2 | 6/2014 | Peterson et al. | |
| 8,757,035 | B2 | 6/2014 | Kerboul et al. | |
| 8,771,271 | B2 | 7/2014 | Overes | |
| 8,777,960 | B2 | 7/2014 | Murray et al. | |
| 8,795,371 | B2 | 8/2014 | Marnay et al. | |
| 8,828,007 | B2 | 9/2014 | Stad et al. | |
| 8,845,697 | B2 | 9/2014 | Montello et al. | |
| 8,845,700 | B2 | 9/2014 | Kwak et al. | |
| 2006/0085071 | A1 | 4/2006 | Lechmann | |
| 2011/0098747 | A1 | 4/2011 | Donner et al. | |
| 2011/0230971 | A1 | 9/2011 | Donner et al. | |

FOREIGN PATENT DOCUMENTS

| | | | |
|---|---|---|---|
| CN | 101442944 | B | 5/2009 |
| EP | 0427906 | A1 | 5/1991 |
| EP | 2361573 | A2 | 8/2011 |

OTHER PUBLICATIONS

Sprayshield.org, Informations about adhesions barriers and SprayShield Adhesion barrier, the new product by Covidien, Oct. 2011.

Women's Surgery Group, Adhesion Overview, Aug. 21, 2014.

The American Journal of Surgery, Peritoneal adhesions and their relation to abdominal surgery, vol. 126, Issue 3, pp. 345-353, Sep. 1973.

British Journal of Surgery Society Ltd, Morbidity and mortality of inadvertent enterotomy during adhesiotomy, vol. 87, Issue 4, Apr. 2000, published online Dec. 6, 2002.

American Academy of Orthopaedic Surgeons, Choosing Wisely, An initiative of the ABIM Foundation, Sep. 11, 2013.

Human Reproduction Update, Clinical implications of postsurgical adhesions, vol. 7, No. 6, pp. 567-576, 2001.

The Lancet, Adhesion-related hospital readmissions after abdominal and pelvic surgery: a retrospective cohort study, vol. 353, Issue 9163, pp. 1476-1480, 1999.

PubMed NCBI, Peritoneal adhesions; etiology, pathophysiology, and clinical significance. Recent advances in prevention and management Dig. Surg. 2001; 18(4):260-73.

MedicineNet.com, Abdominal Adhesions (Scar Tissue), Aug. 20, 2014.

Better Health Channel, Fact Sheet, Adhesions, Aug. 20, 2014.

Journal of Surgical Research, Heated and Humidified CO, Prevents Hypothermia, Peritoneal Injury, and Intra-Abdominal Adhesions During Prolonged Laparoscopic Insufflations, vol. 152, Issue 1, pp. 40-47, Jan. 2009, published online May 12, 2008.

Oxford Journals, Medicine and Health, Human Reproduction Update, vol. 19, Issue 1, pp. 12-25, Jan./Feb. 2013, published online Aug. 16, 2012.

Synechion, Inc., Adhesions Related Disease-Adhesions Related Deaths, Sep. 23, 2003.

PubMed NCBI, Histologic study of peritoneal adhesions in children and in rat model, Pediatr Surg Int. Dec. 2002; 18(8):676-6, Epub Sep. 24, 2002.

Human Reproduction Update, Peritoneal repair and post-surgical adhesion formation, vol. 7, No. 6, pp. 547-555, 2001.

* cited by examiner

SACROILIAC, ANCHORING APPARATUS AND METHOD

RELATED APPLICATIONS

This application: is a continuation-in-part of U.S. patent application Ser. No. 16/838,827, filed Apr. 2, 2020 scheduled to issue as U.S. Pat. No. 11,701,238 on Jul. 18, 2023; which is a continuation-in-part of U.S. patent application Ser. No. 16/263,405, filed Jan. 31, 2019, issued as U.S. Pat. No. 10,898,345, issued on Jan. 26, 2021; which is a divisional application of U.S. patent application Ser. No. 15/380,048, filed Dec. 15, 2016, issued as U.S. Pat. No. 10,195,051 on Feb. 5, 2019; which is a divisional application of U.S. patent application Ser. No. 15/001,502, filed Jan. 20, 2016, issued as U.S. Pat. No. 9,539,110 on Jan. 10, 2017; which is a divisional application of U.S. patent application Ser. No. 13/937,208, filed Jul. 8, 2013, issued as U.S. Pat. No. 9,248,029 on Feb. 2, 2016; which is a continuation of PCT Application Serial No. PCT/US2012/020560, filed Jan. 6, 2012; which claims the benefit of U.S. Provisional Patent Application Ser. No. 61/430,296, filed Jan. 6, 2011. All the foregoing references are hereby incorporated herein by reference.

BACKGROUND

1. Field of the Invention

This invention relates to orthopedic surgery and, more particularly, to novel systems and methods for anchoring to and between bone structures.

2. Background Art

Orthopedic surgery has long depended on unique instruments and unique securement arrangements in order to encourage healing of fractures, regrowth of bone structures, and the like. Various securement mechanisms involve combinations of plates and screws, sometimes rods, and various other hardware.

Bones have a structure that is harder around the outside envelope (boundary) thereof, called cortical bone. Meanwhile, enclosed therewithin is medullar bone, sometimes called cancellous bone. Cancellous bone hosts the marrow and vasculature associated therewith. Consequently, the bone itself is quite porous and sparse, sometimes referred to as "spongey." Cancellous or medullar bone material has less actual structural material forming around vacuoles containing soft tissues (marrow, vasculature, etc.). It has reduced ability to maintain embedded rigidly therein a conventional thread of a screw.

Meanwhile, thread pitch is of the same order of magnitude as the height of the threads from the shank (solid shaft) of a screw. Thus, the actual "purchase" (physical engagement or contact between the screw and the structural material of the bone) is much less in the cancellous bone than in the cortical bone. However, the cortical bone is comparatively thin, typically, or a comparatively small fraction of many bones or bone structures and length of screws anchored therein.

That is, just as in wood, threads on a screw or similar hardware may simply shear (core out) the corresponding threads they cut into the receiving bone. Thus, pull-out strength may be severely compromised by the spiraling threads with their intermediate bone material therebetween. It would be an advance in the art to provide a more secure form of anchoring. It would be an advance in the art to provide anchors capable of securing into cortical bone and cancellous bone with reduced risk of simply "coring" out.

Meanwhile, bone regrowth or "through growth" around and through foreign objects such as screws, plates, spacers, or the like is to be promoted. It would be an advance in the art to improve spaces for "through growth" through spacers or frames used with anchors in various types of surgery.

It would be an advance in the art to provide anchors capable of securing one bone structure to another in order to promote joinder therebetween. It would be an advance in the art likewise to provide both spacers and anchors having apertures, porosity, highly textured surfaces, and the like in order to provide more shear strength, as opposed to mere friction securing new bone growth to spacers, anchors, and so forth.

BRIEF SUMMARY OF THE INVENTION

In view of the foregoing, in accordance with the invention as embodied and broadly described herein, a method and apparatus are disclosed in one embodiment of the present invention as including an anchor selected from several types that may be directly driven (malleted) rather than screwed with a driver. Anchors may include a central aperture or channel along a center line, where the center line is itself curved, such as on a radius or arc. In certain embodiments, the anchors may include splines. The splines may parallel the center line (center curve) as they extend radially away from a wall of a central channel or core. Splines may each progress helically in a comparatively long pitch, helical direction. By "long pitch" is meant that the pitch is typically multiple diameters, and even multiple lengths long. Pitch represents a distance traversed by a flute (where a flute may be a thread or a spline) per revolution of rotational progress. The twist (distance per revolution) in a conventional screw is typically sufficiently small that a full 360 degree rotation (two pi radians, or $2\times\pi$ radians) occurs at a fraction of the diameter distance.

For example, a one quarter by 20 (¼×20) bolt or screw has a one quarter inch diameter in which 20 threads or 20 revolutions of the threads occur in every inch of length. This means an inch of axial progress occurs in 20 complete circles or complete spirals of the threads. In contrast, an anchor in accordance with the invention has a pitch that is typically several lengths (even up to dozens of diameters) of the fastener or anchor.

Splines are angled primarily to travel along their length, while progressing along a helical path that will typically not make a full revolution within the entire length, or even a few lengths, but many (e.g., four, six, eight, or more).

Thus, such splines will typically make less than one quarter (usually from one sixth to one tenth) of a revolution or progress about the circumference within the entire length. Meanwhile the aspect ratio of diameter to length is itself less than a fifth to a tenth (1:5 to 1:10). In fact, the progression or the amount of angle traversed circumferentially is typically on the order of only one eighth (⅛) of the circumference or less.

Thus, anchors in accordance with the invention may be malleted (driven axially by impact loading) into place. Spiraling and twisting by the splines moves the anchor through the cortical bone and along both an arcuate centerline and a helical path through the cancellous bone therewithin. The result is that only a small fraction of the spline surface area aligns parallel to the pull-out direction (back toward the head. Thus, the splines resist any force tending to pull out, while they themselves present a significantly greater surface area and less load (pressure, force per unit area) against the cancellous bone than does a conventional screw.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

FIGS. 16A through 16H, are examples of one embodiment of an anchor in accordance with the invention, illustrating various types of texturing, including regular, irregular, convex surfaces, concavities, barbs, and so forth;

FIG. 19A is a dilator, which amounts to a tissue stretching device for providing access to tools, without incising tissues, blood vessels, muscle, and the like;

DETAILED DESCRIPTION OF THE PREFERRED EMBODIMENTS

Figure 1A:
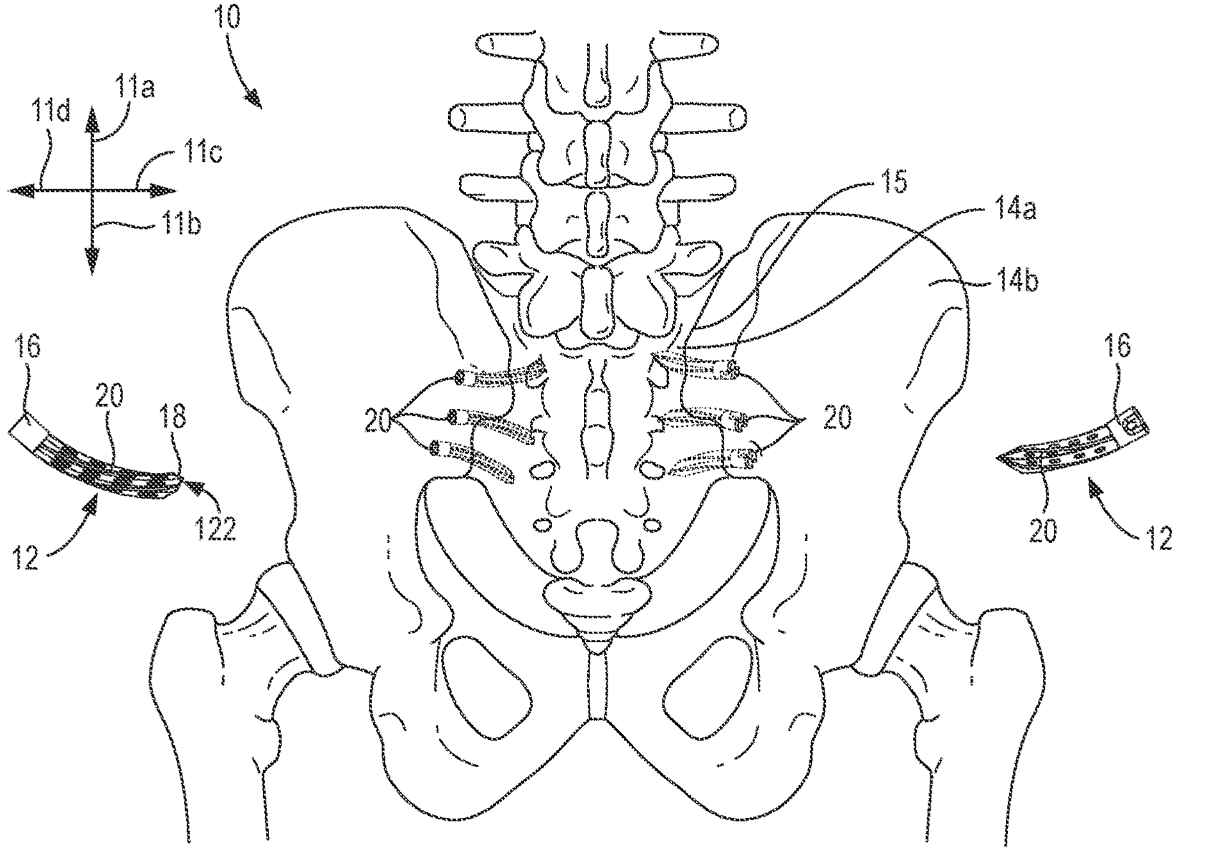
FIG. 1A is a posterior (rear elevation) view of a sacroiliac (SI) joint fusion relying on one embodiment of three anchors for each joint fixation, illustrating one embodiment of an anchor on the right, and another embodiment on the left, implemented in an apparatus and method in accordance with the invention.
Figure 1B:
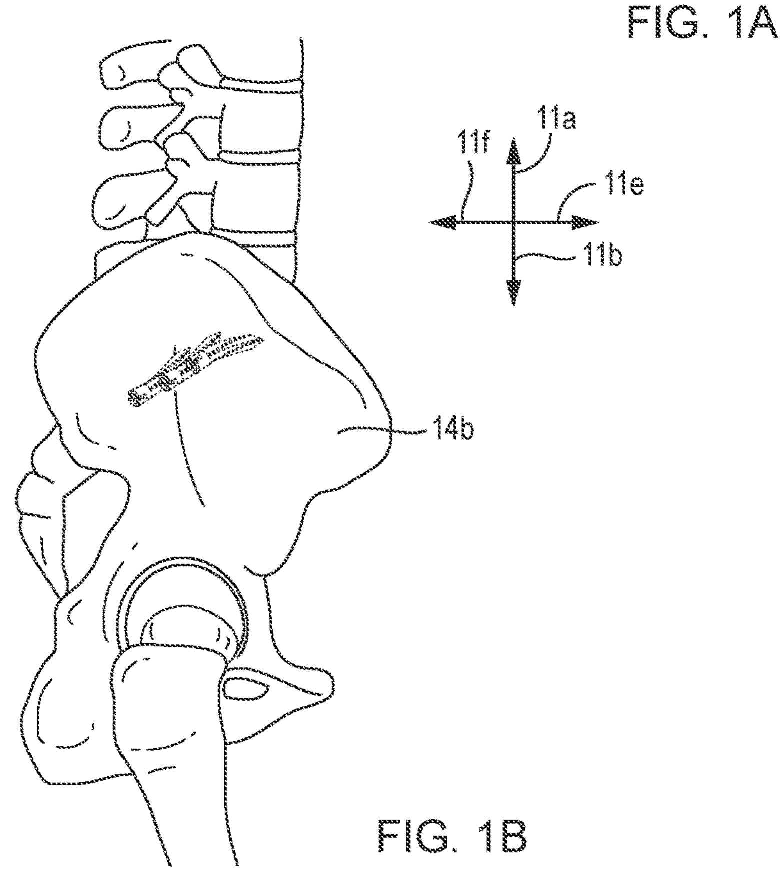
FIG. 1B is a lateral (right side elevation) view thereof, an opposite side being a mirror image thereon.
Figure 1C:
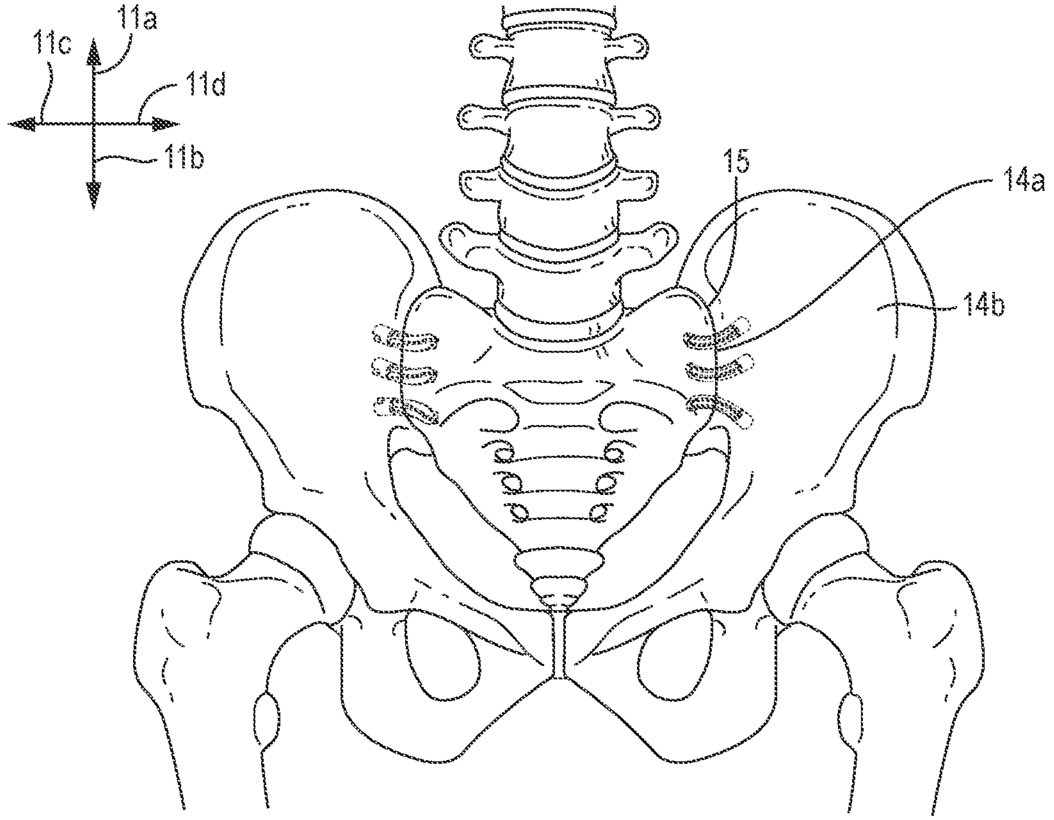
FIG. 1C is an anterior (front elevation) view thereof.
Figure 1D:
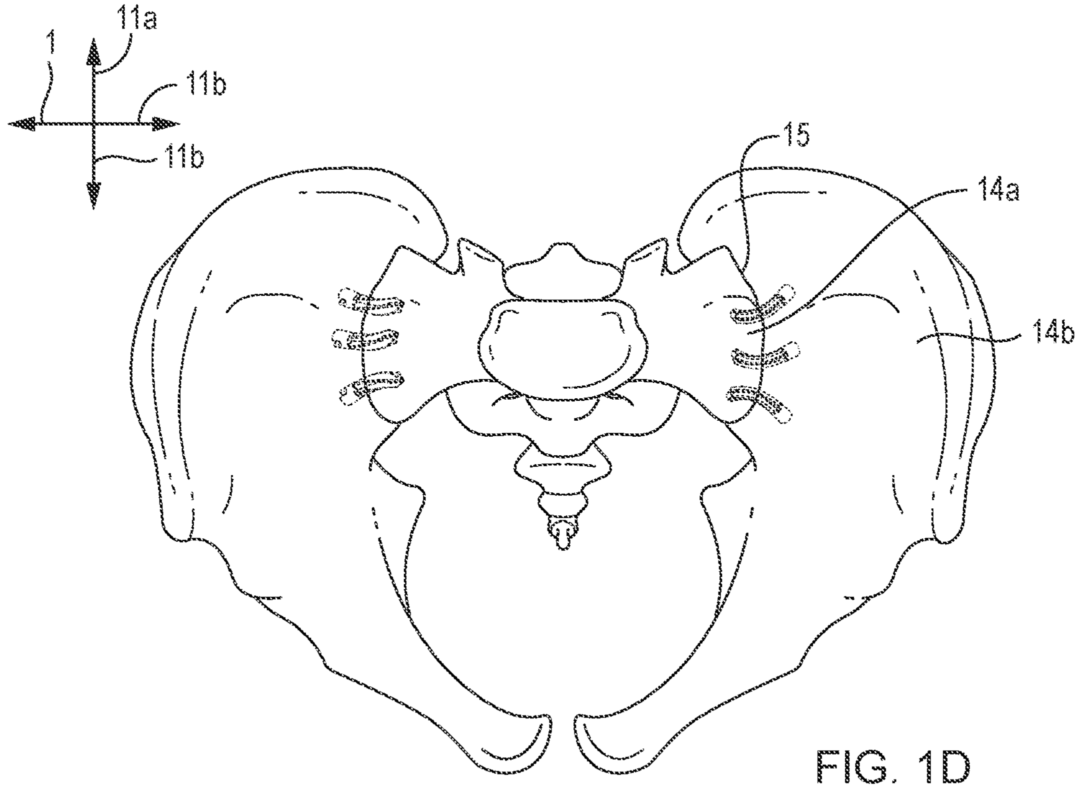
FIG. 1D is a superior (top plan) view thereof.
Figure 1E:
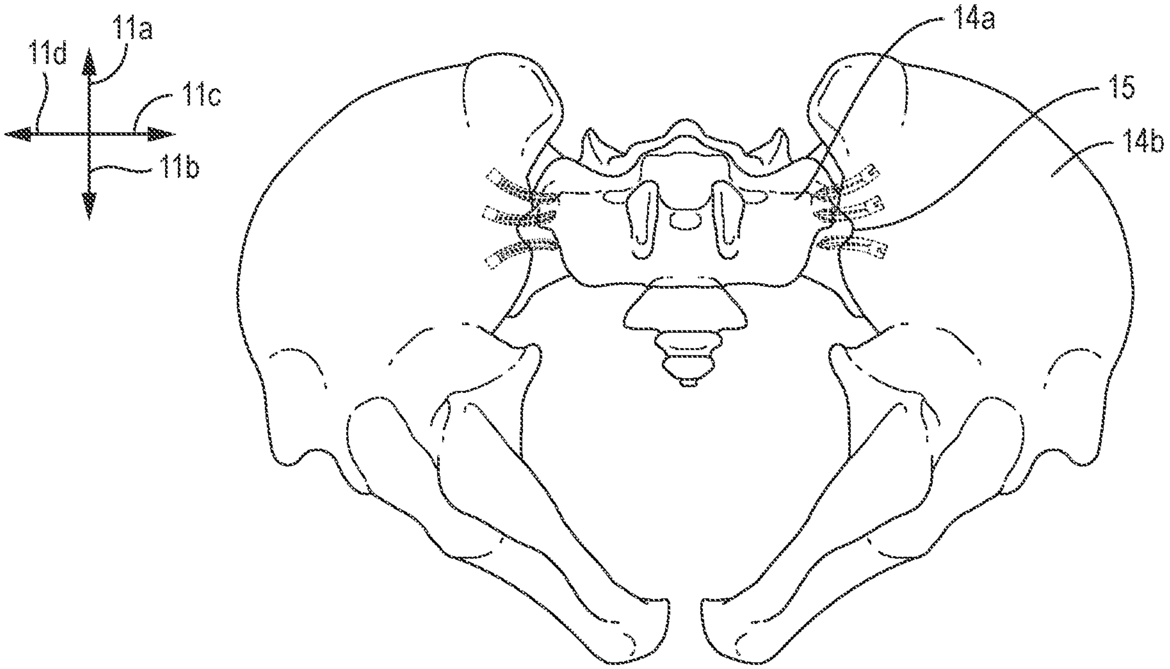
FIG. 1E is an inferior (bottom plan) view thereof.
Figure 1F:
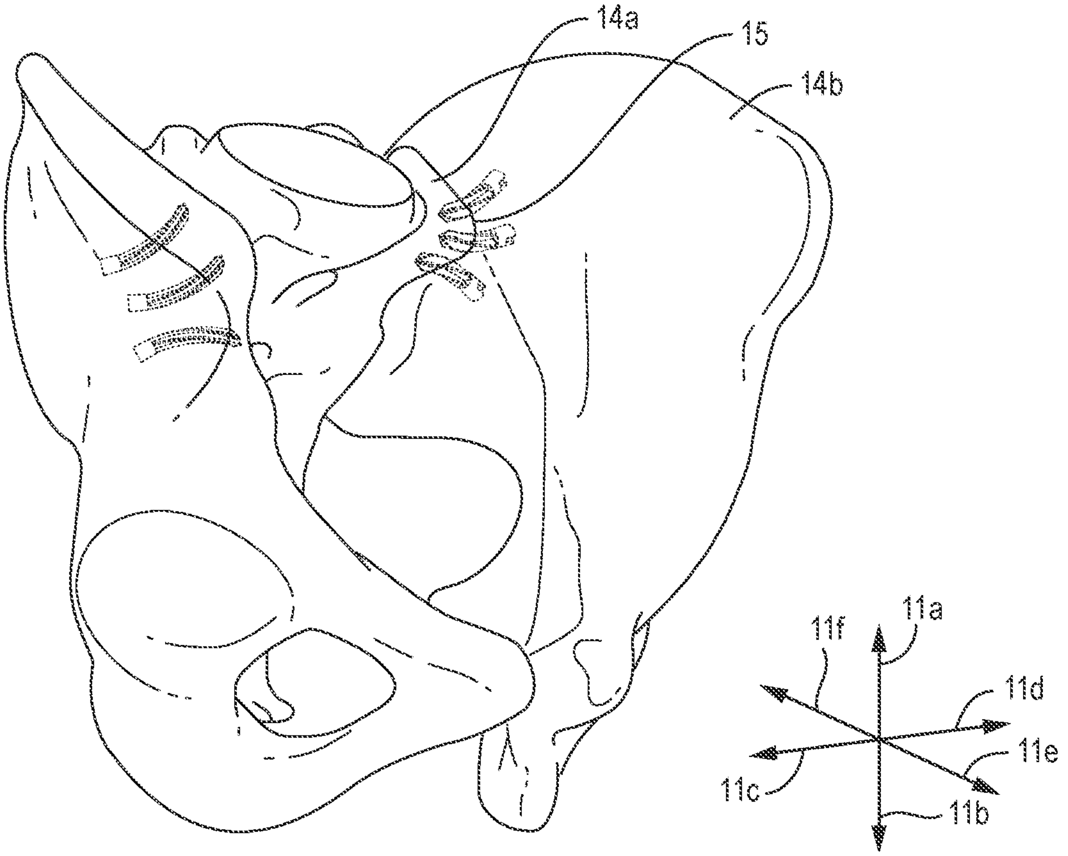
FIG. 1F is a superior and anterior (upper and frontal), perspective view thereof.
Figure 1G:
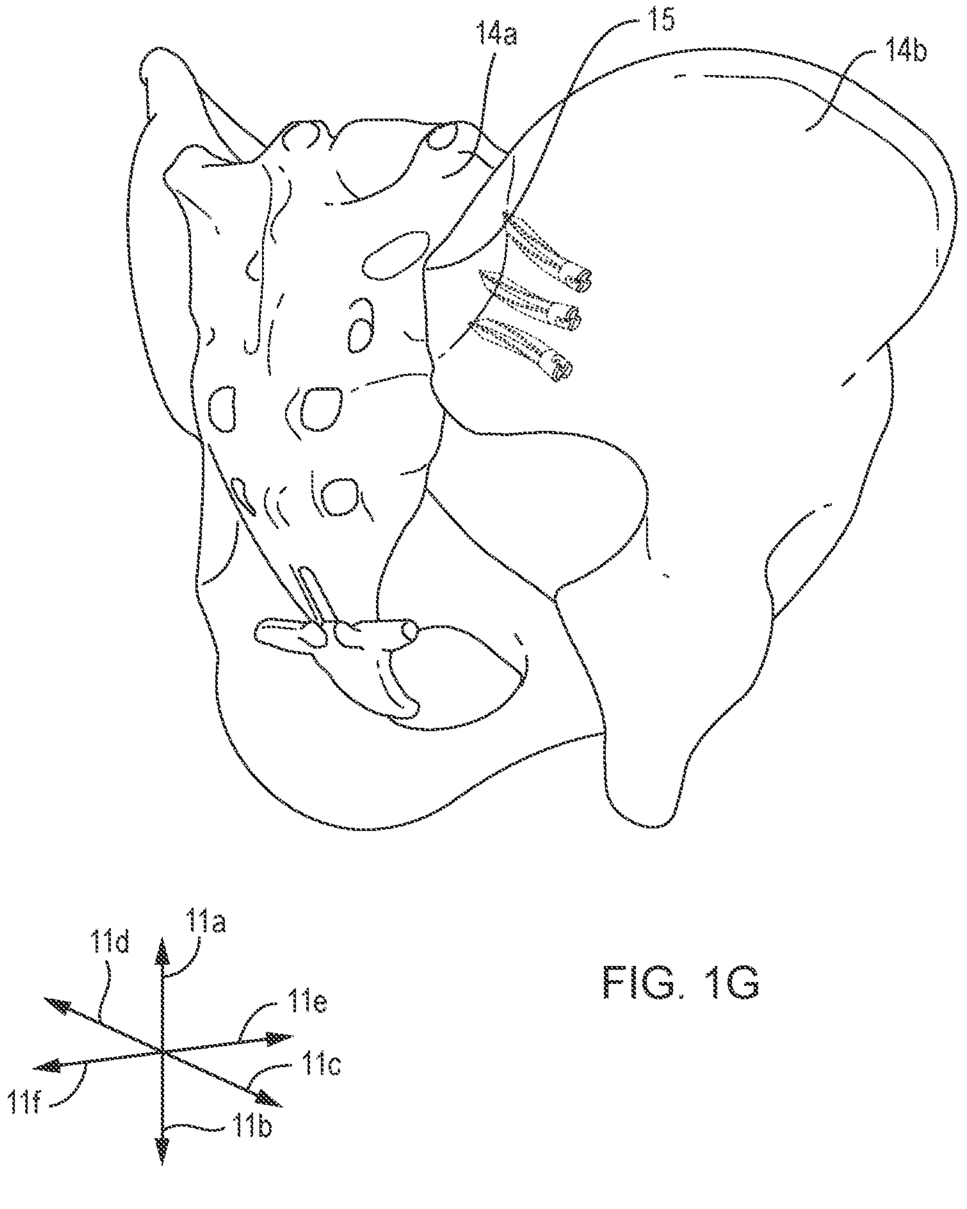
FIG. 1G is an inferior and posterior (lower and rear), perspective view thereof.
Figure 1H:
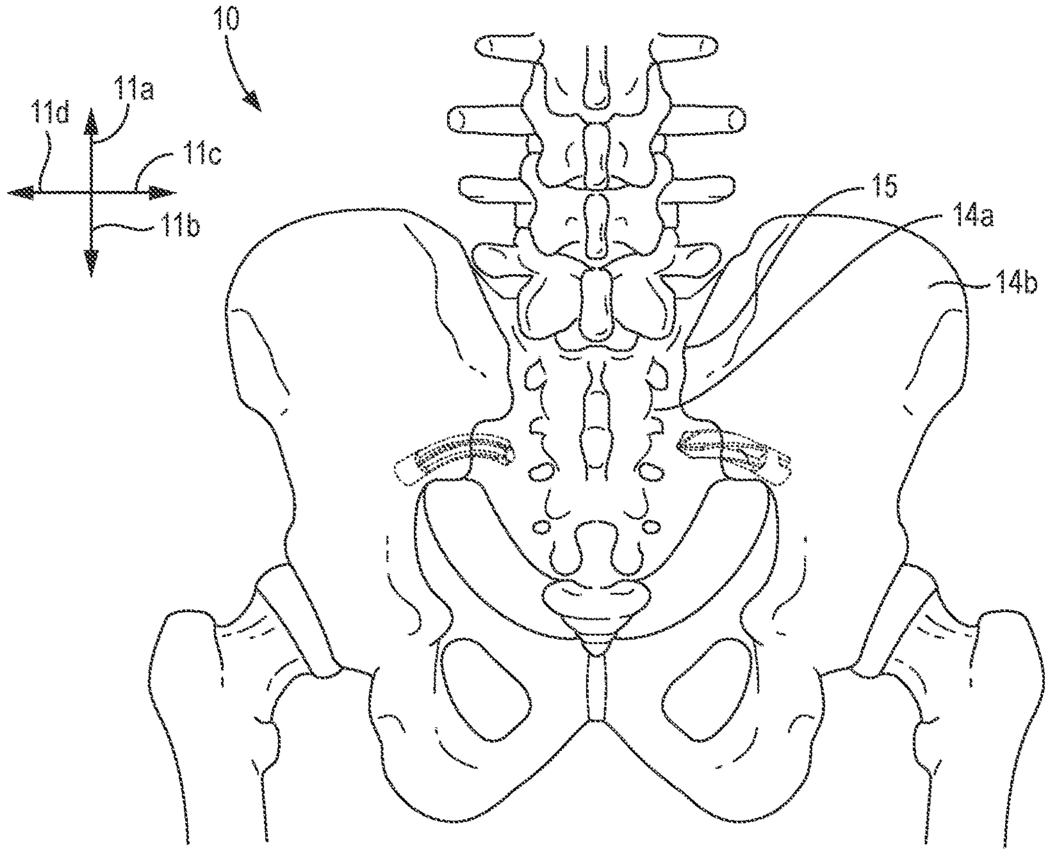
FIG. 1H is a posterior (rear elevation) view of a sacroiliac (SI) joint fusion relying on a single anchor (different embodiments shown on left and right sides) for each joint fixation in alternate embodiments of an apparatus and method in accordance with the invention.
Figure 1J:
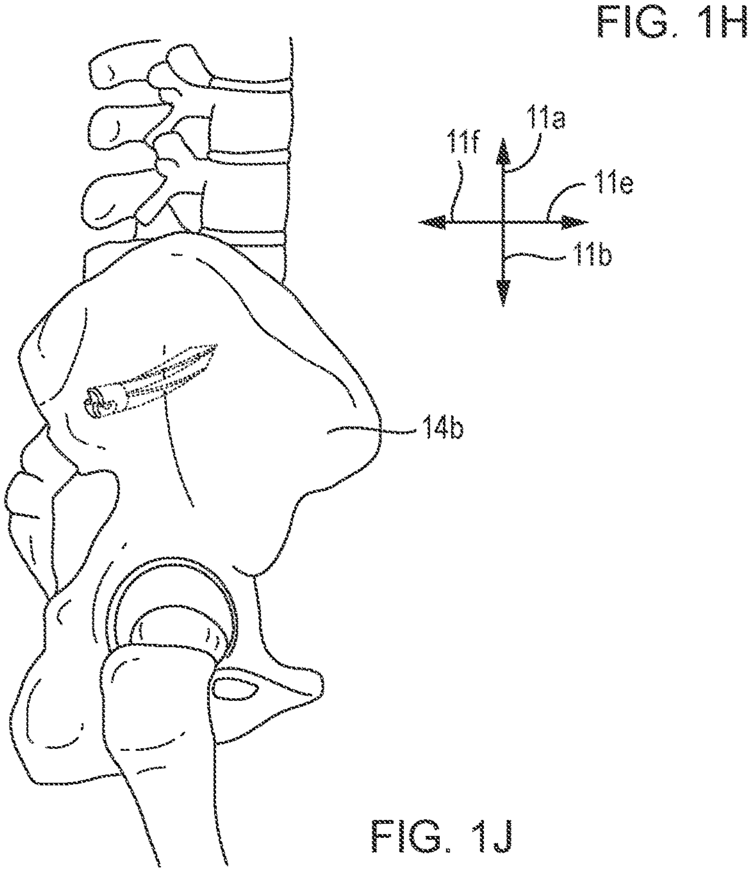
FIG. 1J is a lateral (right side elevation) view thereof, an opposite side being a mirror image thereon.
Figure 1K:
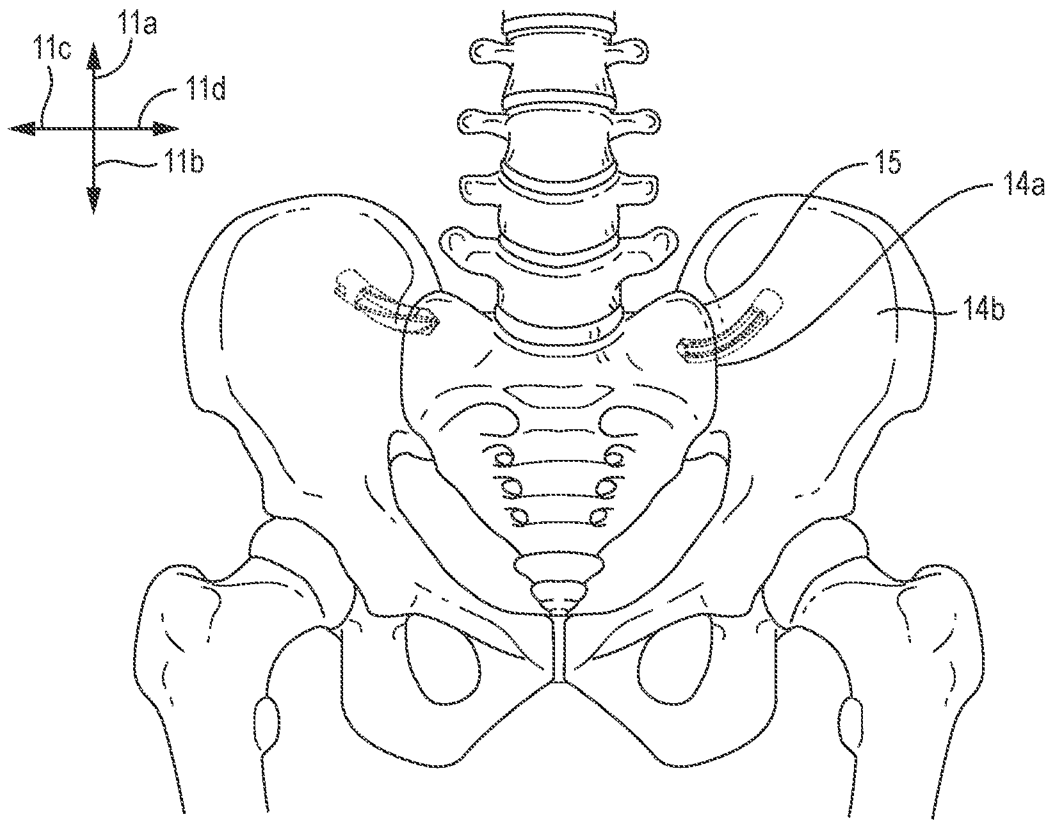
FIG. 1K is an anterior (front elevation) view thereof.
Figure 1M:
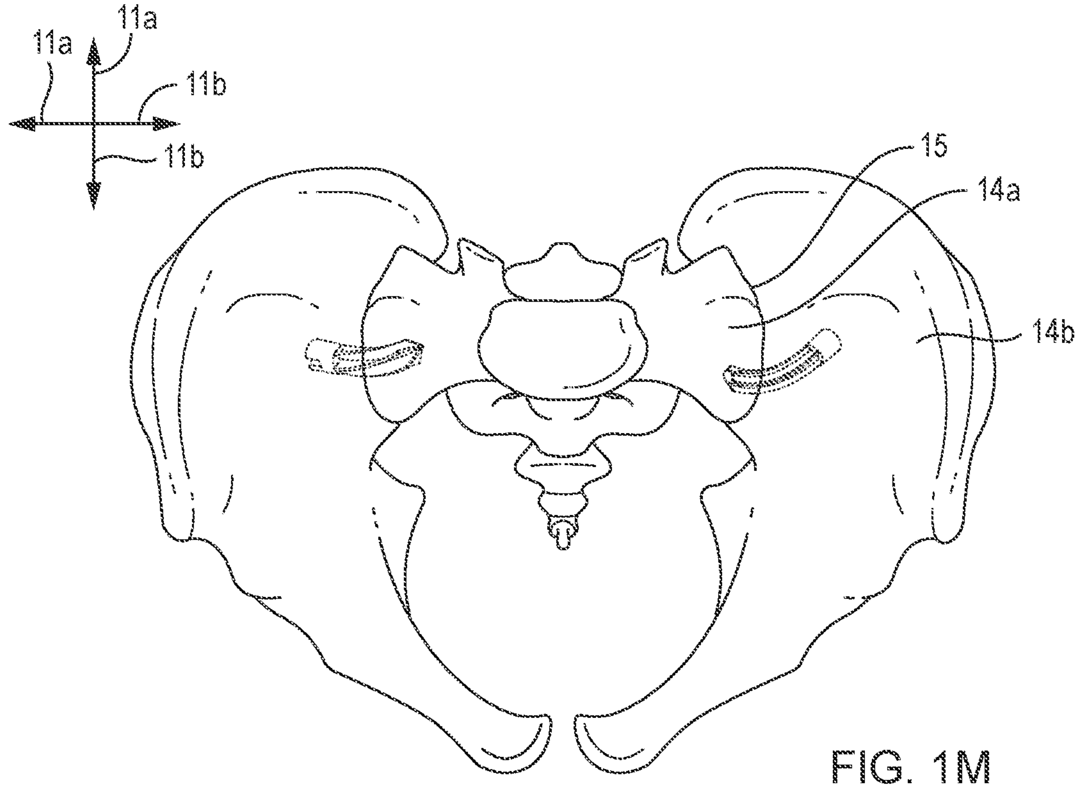
FIG. 1M is a superior (top plan) view thereof.
Figure 1N:
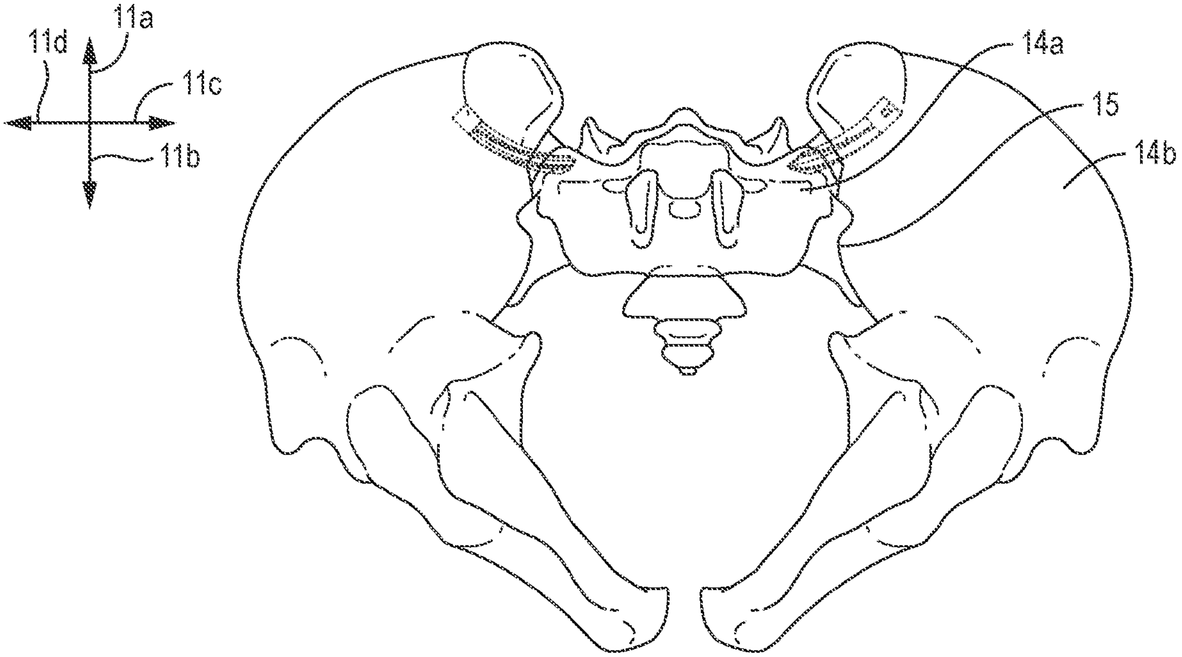
FIG. 1N is an inferior (bottom plan) view thereof.
Figure 1P:
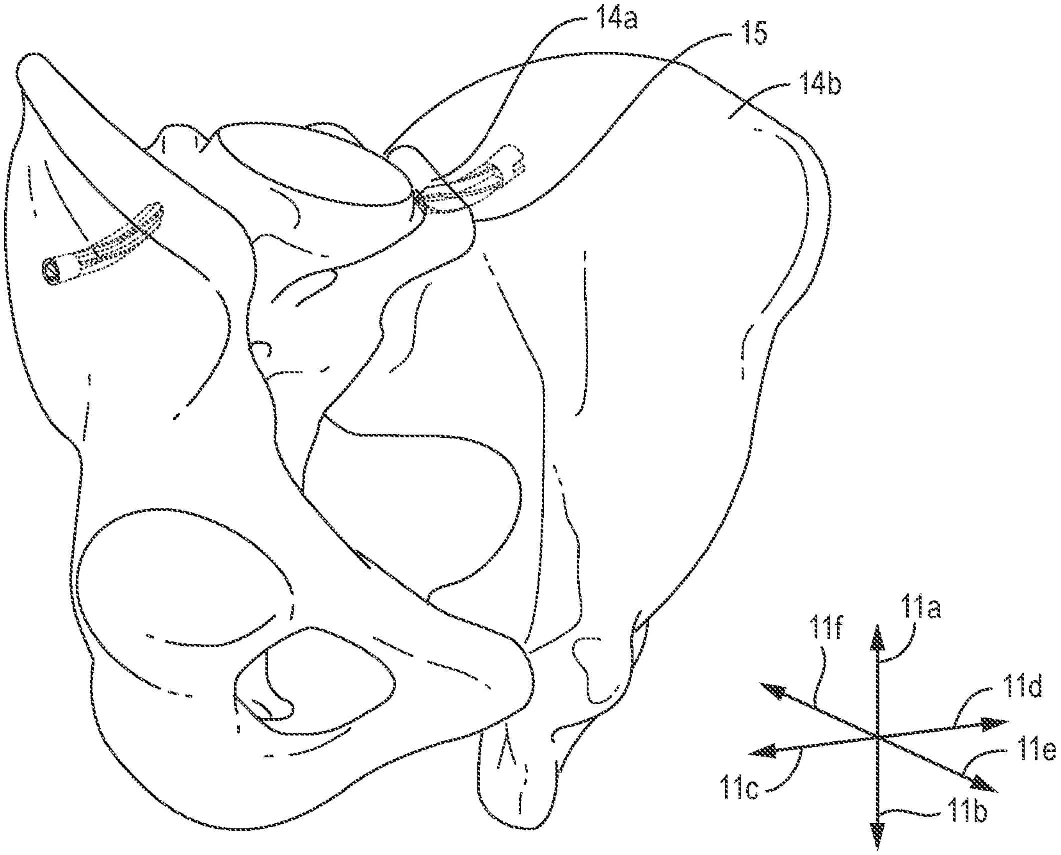
FIG. 1P is a superior and anterior (upper and frontal), perspective view thereof.
Figure 1Q:
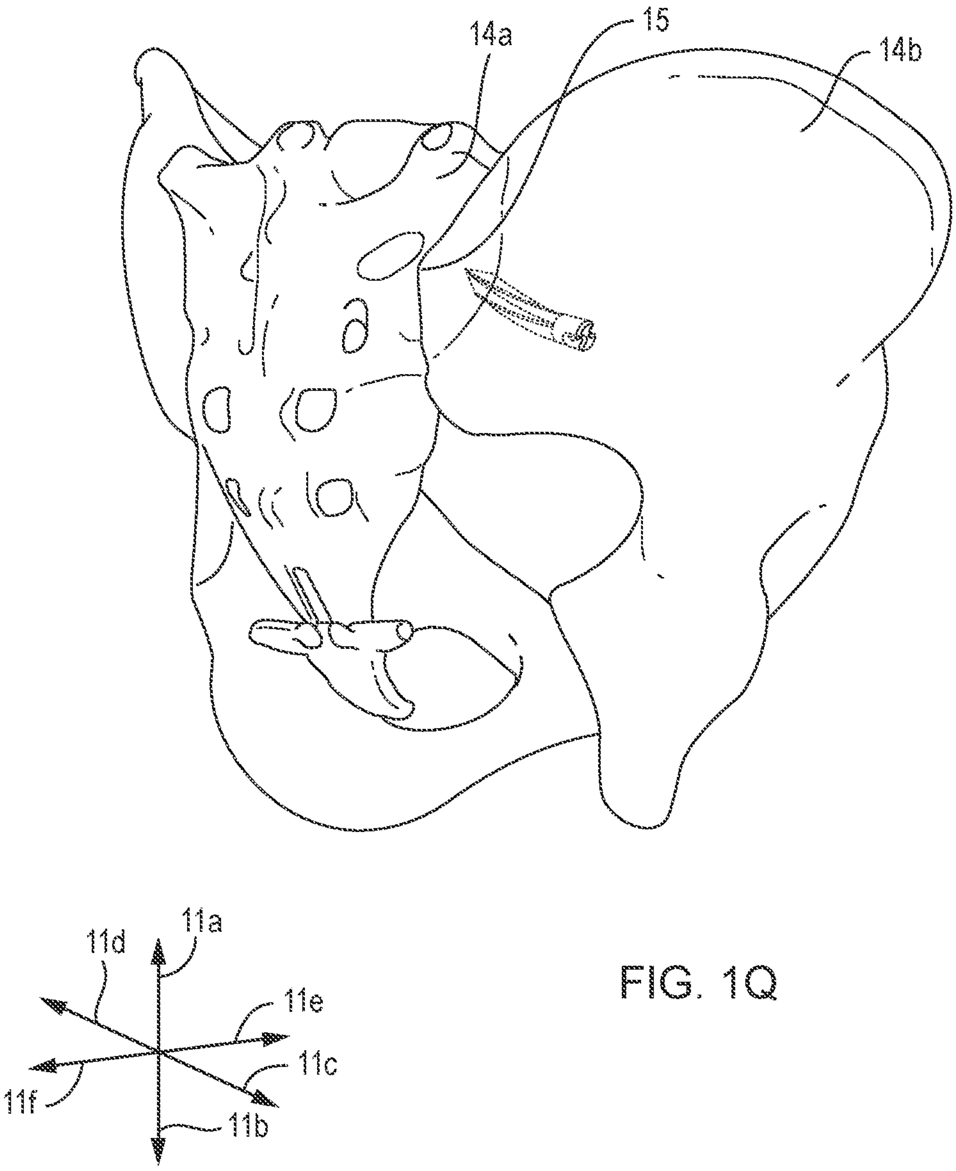
FIG. 1Q is an inferior and posterior (lower and rear), perspective view thereof.
Figure 1R:
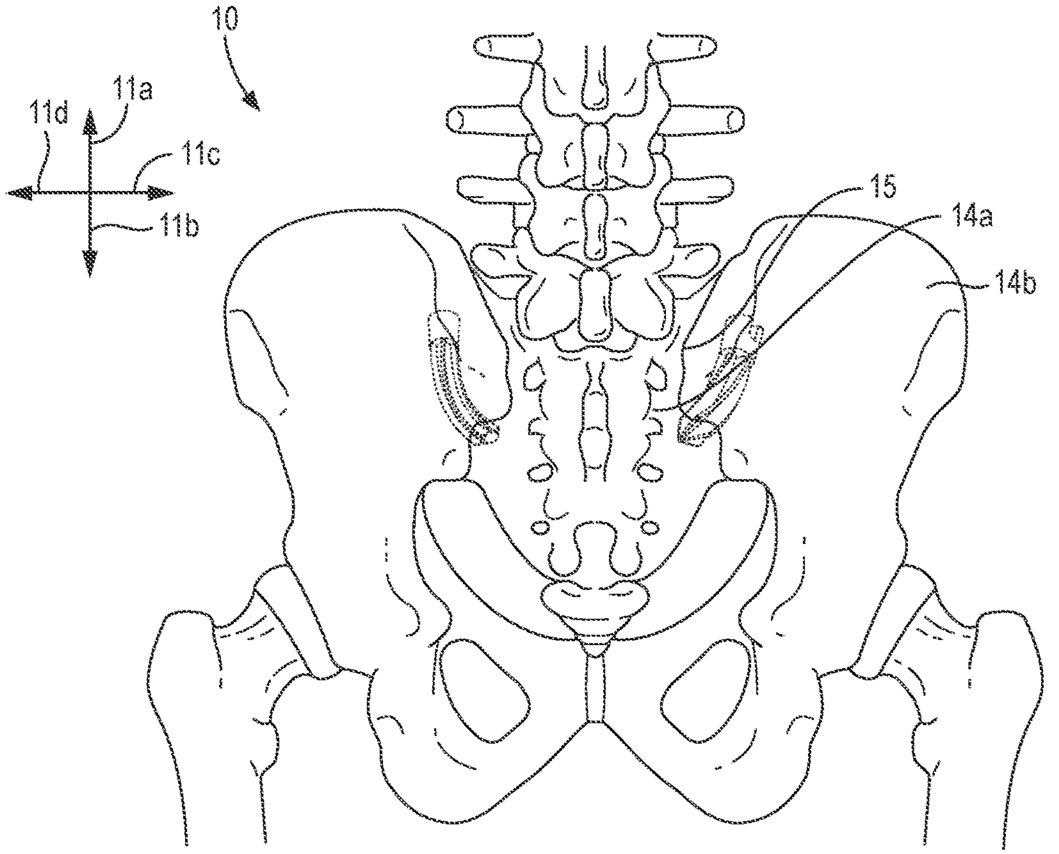
FIG. 1R is a posterior (rear elevation) view of a sacroiliac (SI) joint fusion relying on a single anchor inserted from posterior access in a joint along the direction of the joint boundary, between the sacrum and the ilium, for each joint fixation in an alternate embodiment of an apparatus and method in accordance with the invention.
Figure 1S:
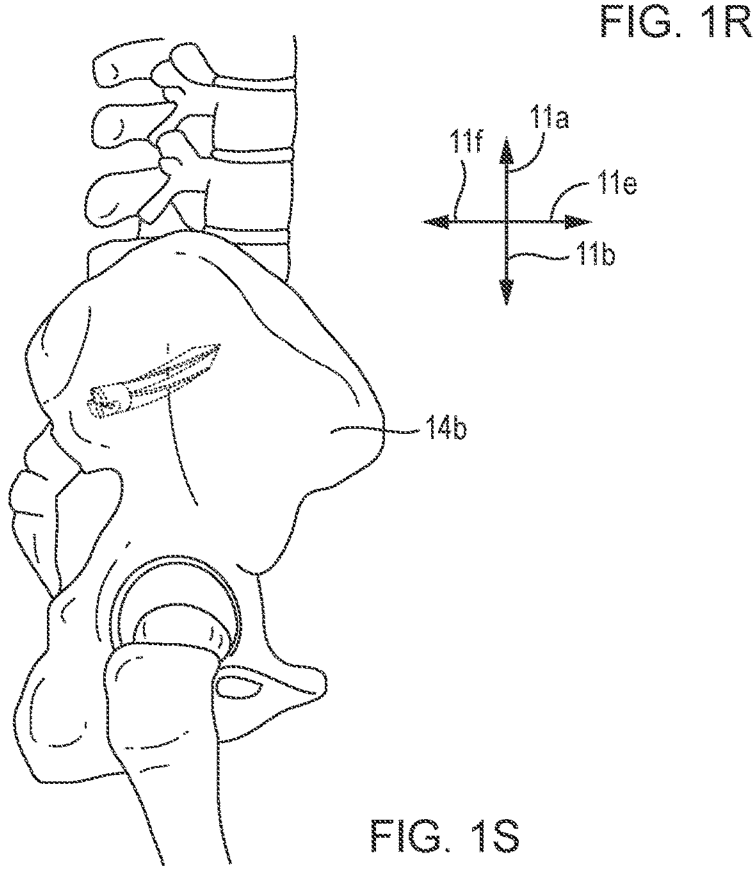
FIG. 1S is a lateral (right side elevation) view thereof, an opposite side being a mirror image thereon.
Figure 1T:
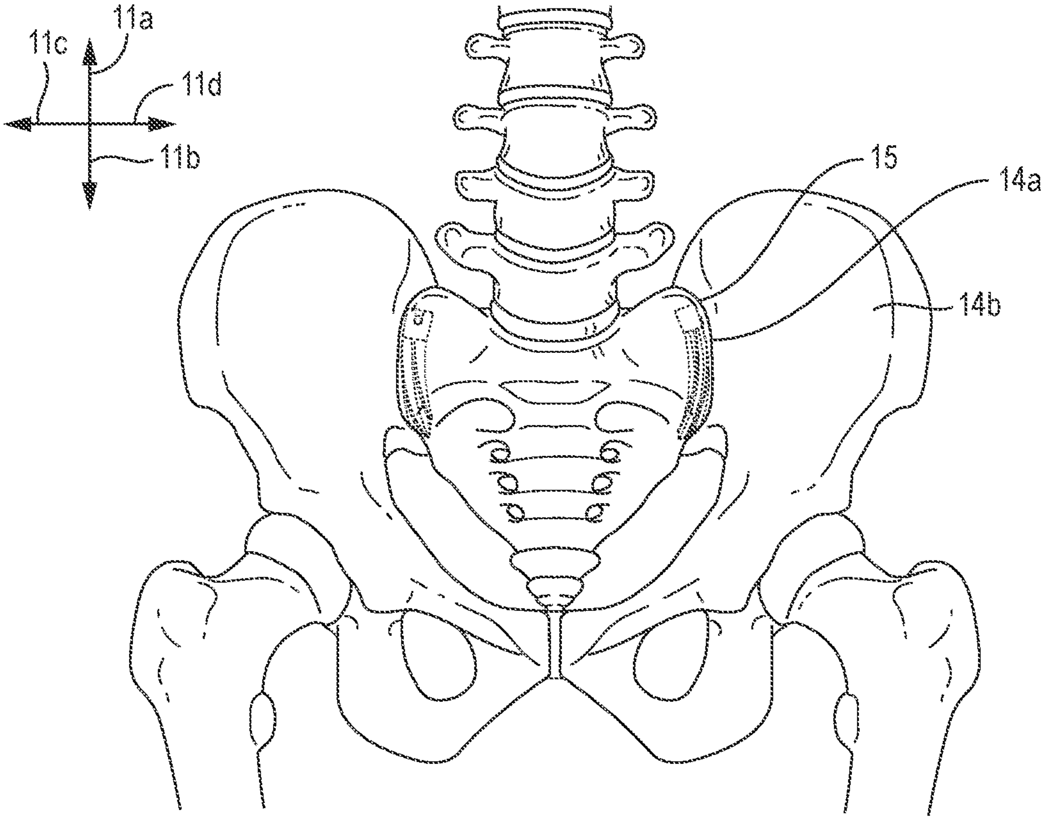
FIG. 1T is an anterior (front elevation) view thereof.
Figure 1U:
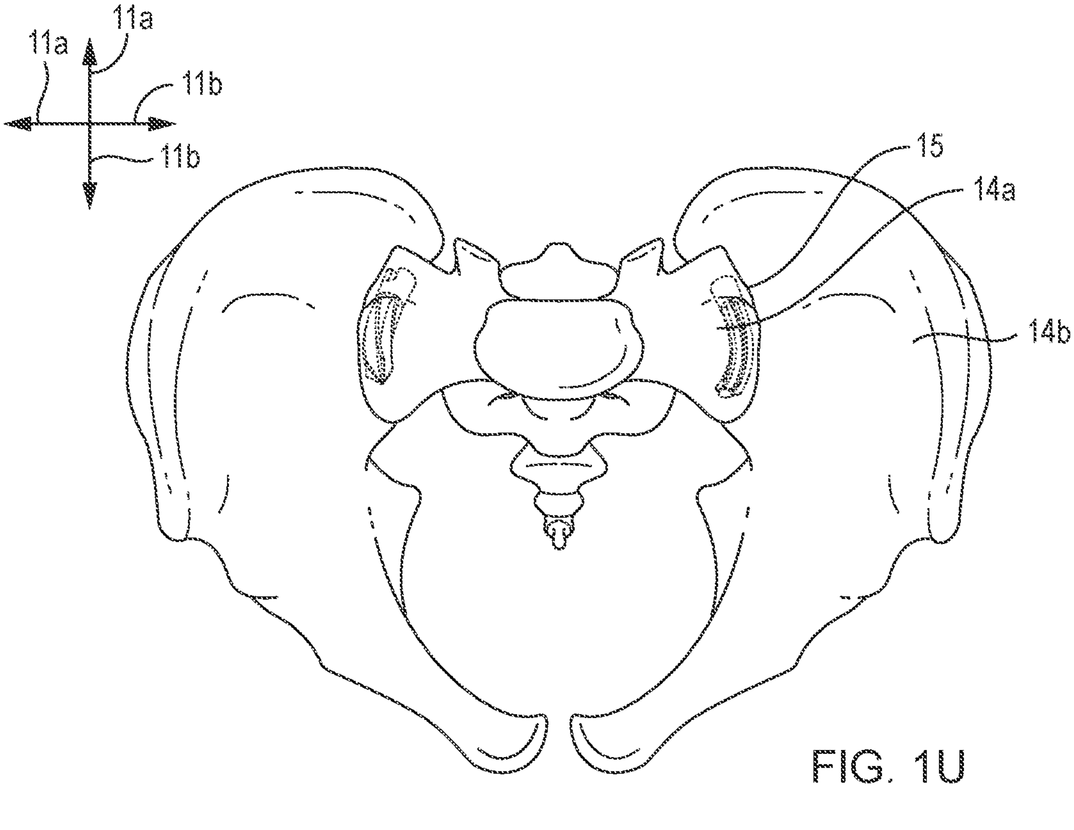
FIG. 1U is a superior (top plan) view thereof.
Figure 1V:
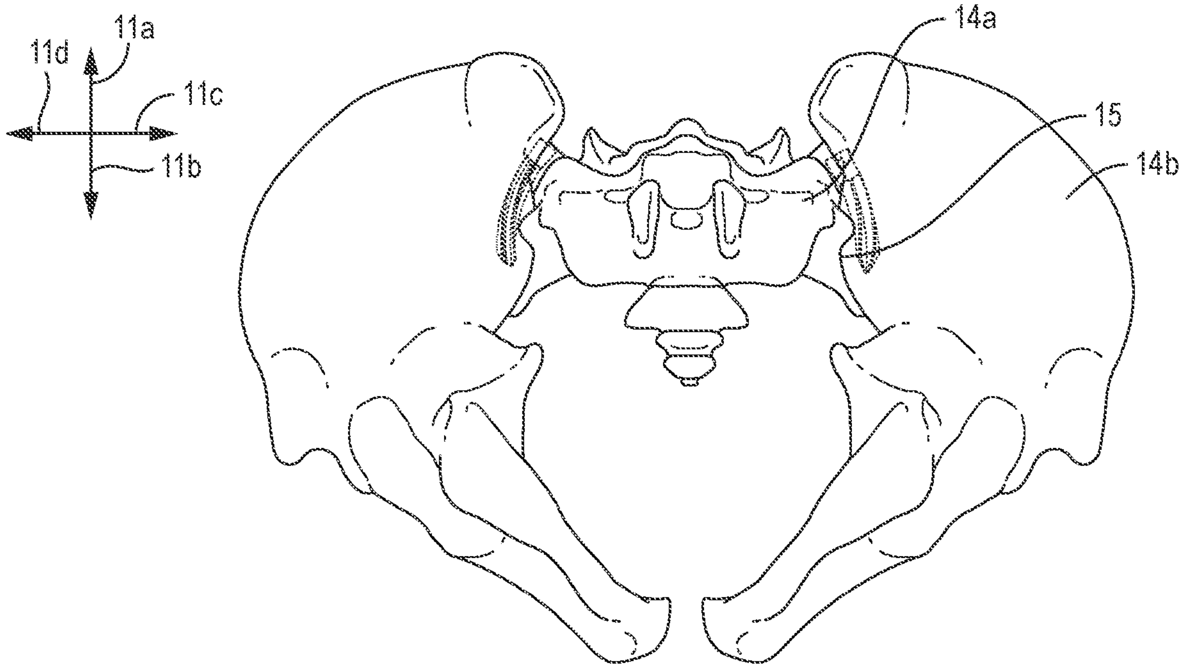
FIG. 1V is an inferior (bottom plan) view thereof.
Figure 1W:
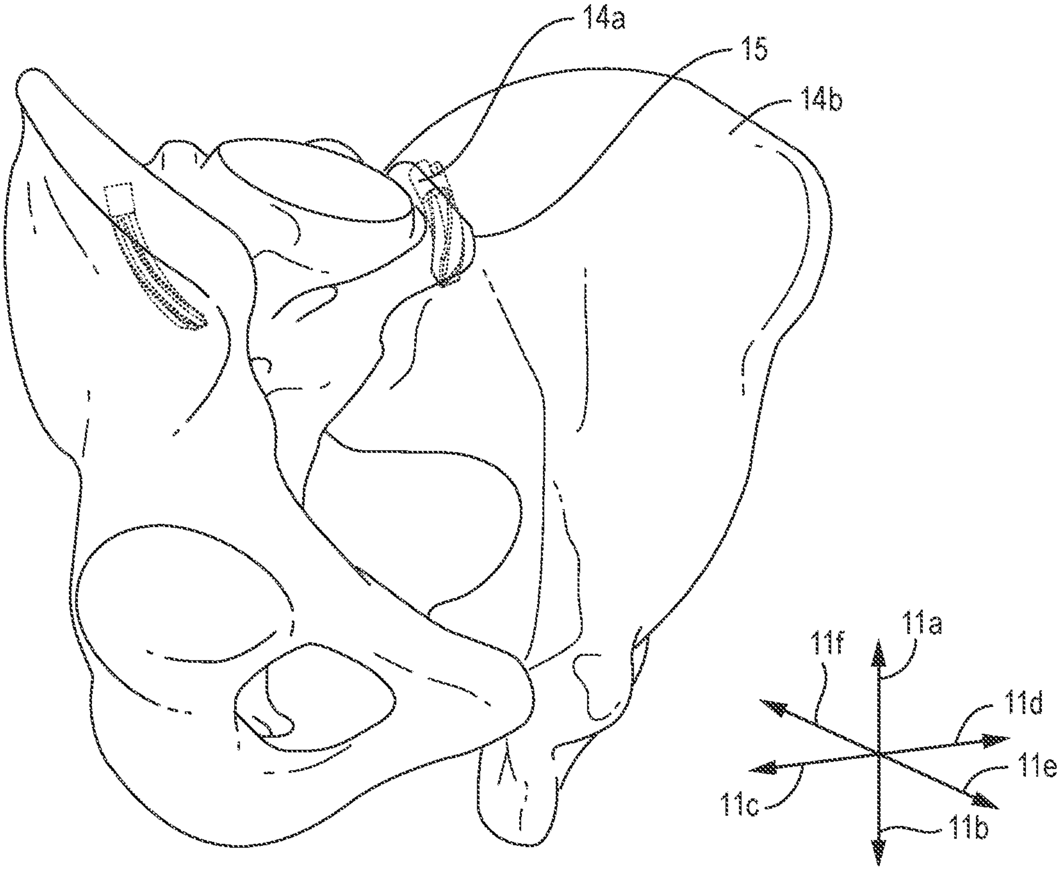
FIG. 1W is a superior and anterior, right aspect, (right, upper, and frontal) perspective view thereof.

It will be readily understood that the components of the present invention, as generally described and illustrated in the drawings herein, may be arranged and designed in a wide variety of different configurations. Thus, the following more detailed description of the embodiments of the system and method of the present invention, as represented in the drawings, is not intended to limit the scope of the invention, as claimed, but is merely representative of various embodiments of the invention. The illustrated embodiments of the invention will be best understood by reference to the drawings, wherein like parts are designated by like numerals throughout.

Herein, a number of unique terms are used, and others have unique definitions. Definitions of conventional structures are inadequate to describe certain features of embodiments of certain features in accordance with the invention. Moreover, certain terms will be necessarily terms of art specifically defined herein due to the lack of any suitable definition in prior art or in the art to which this invention pertains. Likewise, sometimes a definition or group of definitions may need to be narrowed down to the specific intent desired in order to adequately describe and claim the invention described herein.

An aperture is basically a hole. An aperture through a thin material may be virtually a two-dimensional plane. An orifice or an exit opening may be thought of as a plane past which a fluid flows. Other apertures may have to pass through a wall, or conduit, and therefore will not only have an area through which it passes but also a distance through which it passes. However, the point of the use of the word aperture is simply to show that a hole has been created for some purpose. The length of an aperture is insignificant. That is, if a significant distance is involved, then a channel or a path is spoken of. That is not typically defined as an aperture, but a line, path, channel, conduit, or the like, and may even have an entrance, exit (both of which are planes), or both identified.

Orthogonal means two items are oriented at right angles to each other. However, orthogonality applies in all kinds of reference systems. In polar coordinates a radius from an axis is based on circular, planar geometry, while the azimuth or the distance along that axis may be defined either by an angle from an axis or a distance from a reference plane. Similarly, spherical coordinates have a frame of reference in which an angle must be defined from three different axes or with respect at three different axes, and a radius to a location must be defined. Herein, orthogonal means that two items, axes, directions, forces, or anything else capable of being characterized by a directionality are oriented at right angles to one another.

However, effectively orthogonal is used to mean that the two items need not be at the exactly orthogonal angles but they are at an angular orientation that if they were connected rigidly, relative motion would be precluded outside the plan of their intersecting axes. In general, three dimensions can be defined in a set of any three coordinates using radii, axial distances, translating distances along Cartesian coordinate axes (rectangular three axis geometry), and so forth. Therefore, it may be necessary sometimes to refer to items that are effectively orthogonal, effectively parallel, or the like.

One reason for this “effective” adjective is the fact that bones are round not square. They tend to have rounded surfaces, edges, and ends, not sharp points. Thus, in running an anchor into a joint “effectively parallel” to the joint or to the two cortical surfaces that are to be fixed “rigidized” to one another will not necessarily be parallel. A straight object may be parallel to a tangent surface (plane instantaneously parallel at a point of contact) or pass along an undulating surface, and thus be called “effectively parallel.

Similarly, an anchor may pass primarily through a cortical surface of a bone, being “effectively” or “primarily” orthogonal thereto. Likewise, two bones may be spaced apart and extend so for some distance, even though they may be rounded conformally with one another or congruent with one another. Thus, the parallelism or the orthogonality may not be absolute. For that purpose, the term “effectively” may be used with the principal term parallel or orthogonal.

Likewise, principally parallel or principally orthogonal are used herein to mean that a device or a force or the like has an effect (typically its greatest effect) in a parallel direction or an orthogonal direction, even though the exact angle may not be precisely parallel or orthogonal. In general, one may rely on the fact that effectively parallel means that a tangent surface or tangent line may be approximately parallel to another even though both are curving. Likewise, principally orthogonal means that most of the orientation is in the orthogonal direction, notwithstanding it may also involve angular variation in other dimensions as well or even in the direction that was intended to be orthogonal but cannot be due to curvatures and so forth. One may typically regard principally parallel to mean less than forty five degrees off of parallel. One may consider principally orthogonal to mean less than forty five degrees off of orthogonal. Most typically, the angular discrepancy will be much less than forty five, much less than thirty.

An implant herein is anything that is embedded in the body of a subject by surgery, minor or major. The anchors used are considered to be implants, because they are intended to take a permanent place in the body, in this case between bones. An anchor as used herein may be relied upon to hold a bone in at least one degree, and typically at least two degrees, of freedom with respect to the anchor. It may anchor to another bone in more degrees of freedom.

Typically, an anchor will hold two bones with respect to one another in at least two degrees of freedom. For example, if an anchor has an axis, and that axis passes through two bones effectively orthogonally with respect to their cortical surfaces, then any plane perpendicular or orthogonal to that axis has two dimensions, and the axial orientation of the anchor fixes those two bones with respect to one another in those two degrees of freedom, the two degrees of freedom that can be used to define the plane perpendicular to the axis of the anchor.

However, in some embodiments, an additional degree of freedom or more may be fixed by virtue of the angles, or by virtue of additional anchors. Meanwhile, those anchors, in the case of multiples, may each fix two bones in two degrees of freedom, and yet duplicate restriction in certain of those degrees of freedom. The action of splines tends to fix anchors in a third degree of freedom.

By degrees of freedom is meant one of the six possible degrees of freedom in a three-dimensional, Cartesian space. In a Cartesian space, three axes, orthogonal to one another, and typically called an x, y, and z axis, define the space. Translation (linear motion) in any direction may be defined in terms of motion or displacement along each of those axes. However, in addition to translation, rotation may also occur. Rotation may similarly be defined according to degrees of rotation of any object or thing about any of those three axes.

The vector algebra may be somewhat complicated. Therefore, it is possible and often relied upon, to use a coordinate system centered, that is it has its origin in or on an object itself. This often simplifies the mathematics by fixing the axis system for translation and rotation to the object, rather than some arbitrary location in space, which might otherwise complicate the mathematics.

By fixing two objects or any object in a degree of freedom means that the freedom to move in that particular direction or degree of freedom has been restricted. Thus to restrict in degrees of freedom is to fix against movement in those particular degrees of freedom, where the degrees of freedom involve three axes of translation (linear movement in the directions of the axes) and any rotation about each of those three axes.

Various definitions used herein or terms needing definitions may include medical terms. For example, distract, means to move apart in tension, such as distracting two bones or distracting ligaments. Typically, in the SI joint (sacroiliac joint) the bones may need to be distracted or moved apart from one another resulting in tensioning or stretching ligaments. Both of these are considered distracting. Stretching or stressing a tissue is to distract it. Likewise, to move two items apart is to distract them.

The medical terms for direction may be used, as well as directional terms. Thus, posterior means rear, anterior means front, superior means above, inferior means below, lateral means a side, and typically means laterally from a center plane of the human body. Likewise, medial typically means at or near or toward a center plane of symmetry through the body, so one may speak of laterally or medially as far as positioning or motion. Pronation is rolling or rocking forward. This would be considered pitching in in aeronautic parlance. Pitching forward, that is nosing down is pronation. Pitching upward, nose up or pitching backward nose up is considered to be supination.

By access herein, is typically meant posterior access or a lateral-posterior access. Posterior access means access through tissues behind the sacroiliac joint whereas lateral-posterior means accessing at an angle that will give access from a side of the ilium but toward the rear, as opposed to from a frontal or anterior access.

Herein, anchoring means that the anchors or an anchor crosses both of the cortical surfaces that it is intended to fix with respect to one another. Parallel engagement or within-the-joint engagement means that an anchor is being installed along the two cortical surfaces sharing a joint, thus distracting the ligaments that hold those bones together. An anchor engages both the bones with at least splines on the anchor, thereby forming a stable fixation. The ligaments drawing the bones together and the anchor cutting into the bones with the splines and distracting the ligaments provide a stabilization.

Materials of the anchors may be inert metals, meaning that they will not react nor degenerate in the presence of materials naturally occurring in the body. However, polymers (plastics) and filled (reinforced) polymers, are improving all the time. Certain ones of these materials may be suitable for certain anchors in certain positions. Likewise, bone itself may be machined to form an anchor, and may thus eventually be subsumed within the bone growth fixing permanently a joint.

Typically, these types of grafts are called allografts, or homografts where the bone is from a same species, but not necessarily of a same blood type, and so forth. Meanwhile, it is conceivable that an autograft (from the subject) may be used, but this is less likely. An autograft involves using bone from the very subject of a surgery. Sacroiliac joint fusions or fixations are typically undertaken due to degeneration of the joint. This is typically a function of health and age. Accordingly, using an autograft is not a reliable process.

Force means force, a fundamental parameter of physics. It may be measured in any units of force. Stress means a force applied per unit area. Stress may occur in tension or compression or shear. The units of stress are force per unit of area. Any units of force and any units of area may be used to define a stress. Strain is a fraction having no dimensions (units) in that it is a measure of stretch in compression or tension of any material as divided by the unit length. Thus, strain is inches per inch, microns per micron, meters per meter, or any length over length, meaning it is a dimensionless (no units of measurement) value.

"Grow-through" means that a region has a porosity, an aperture, a window, a lattice, or some other vacancy through which bone may grow in order to strengthen the region and the attachment where an anchor or implant has been implanted (installed).

"Grow-on" identifies a characteristic of a material in which a texture includes shapes, convex, concave, some combination, or the like that do not pass through the wall onto which these textures are formed, and thus cannot allow bone to grow-through them, but bone may grow around them, and have strength due to the shear strength (shear being a technical engineering term meaning stress in a material orthogonal to the applied force). A coefficient of friction exists between any two materials.

The coefficient of friction is defined as the amount of force required to slide one material along another in a plane per unit of normal force forcing the two materials together at the plane. This is often defined as a Force equals Mu times N, where N is the normal force pushing the two materials together at their surfaces, Mu is the coefficient of friction (a property of those two materials in contact), and the force is the amount of force required to cause them to slip at that interface surface. Again, the coefficient of friction is dimensionless (unitless) because it is the ratio of two forces acting. One benefit of surface texturing is that it does not permanently rely on a coefficient of friction between surfaces, but rather provides small pillars extending up into the bone as it grows and to which the bone may attach itself.

"Pull-out" resistance or force represents a force required to withdraw a fastener once it has been inserted by pulling on that fastener from the direction in which it was forced into place. Screws are typically problematic in this type of testing. Because screws advance only a small fraction of their diameter with each rotation of the head, the threads act like blades or scrapers. Thus, as those threads thread into a material like bone, they are so close together (axially), and have so compromised the material penetrated, that drawing a screw out of the place where it has been threaded in will often "core out" the bone (literally shear out all the material engaged by the threads) where it had been originally threaded. This may happen intentionally or accidentally.

In an apparatus and method in accordance with the invention, threads are not used. Rather splines that extend helically at a very long pitch, where pitch is the distance between one revolution of a helix about a central axis, and the next revolution to the same circumferential point advanced along the helix. Thus with screws the pitch length is often a small fraction of a diameter of the screw. Certain types of screws in woodwork such as bugle-head screws or sheetrock screws, or the like have a larger pitch compared to machine screws, conventional threads, bolts, and the like with lesser pitch. Both are effectively wedges of a few degrees, about 3 degrees off a plane normal (perpendicular, at a right angle) to the longitudinal axis for a machine screw and about 10 degrees for a bugle head screw. In contrast, a helical spline in accordance with the invention typically has a wedge angle of over 90 degrees from that same plane.

One may think of any helical screw as a wedge that is simply coiled around itself so that the wedge may continue advancing longitudinally throughout multiple revolutions. Each revolution is a wedge having a length of Pi times the outer diameter of the screw. Each rotation of a screw advances axially by the distance of the pitch (crest to crest of each adjacent pair of threads). Even a very short, sheet metal screw must have one full turn of threads on a length of about one diameter.

In systems and methods in accordance with the invention, threads are not used. Instead, helical splines are used. Splines as used herein are helical walls that extend out from a central core or even a central axis. These splines extend radially outward but also extend longitudinally in a helical pattern that rotates around the core as they advance longitudinally along the length of the anchor. In accordance with the invention, the helices are not screw threads because their pitch is multiple lengths of the anchor. This means that a spline never completes a single rotation or a single 360 degree helical path around the core.

Typically, an odd number of splines is preferred, and that odd number of splines may be three, but is typically five, and may be more. Pitch does not depend on the number of splines. Three to seven splines may serve, but five splines have been found suitable in practice for both manufacturing and use. A typical pitch in accordance with the invention is greater than five lengths of the anchor, and may be more.

In general, herein, a long pitch means a pitch greater than the total length of the splined portion of an anchor, wherein the length of the anchor is greater than two of its greatest diameter around the splines, and typically about five diameters or more. Nothing sold as a "screw," "bolt," or other "threaded fastener" can qualify as having a "long pitch." A very long pitch is at least two, and typically three to more than five times the splined length of an anchor of length greater than two diameters. Typical anchors are two to four and a half diameters long, and have a pitch of more than five lengths of the anchor. This translates to about three and a half degrees of angle from a longitudinal, axial line drawn at the outer surface of the core from which the splines extend. That is over 95 degrees of angle measured from a plane perpendicular to the longitudinal axis, when compared to screws, which have less than eight degrees for that angle, and typically closer to three degrees for that "wedge angle".

Meanwhile, the term spline herein is used to mean a specific structure. Conventional splines typically involve connectors in which lands, extending radially outward as part of a shaft, alternate with grooves machined radially down into the shaft, alternating circumferentially between the lands. Typically, the circumferential distance across a land and an adjacent groove are essentially the same. Even when a spline has a triangular shape that comes to a single ridge, or if it is a "buttressed" trapezoidal shape adjacent a machined groove, the circumferential distance across the middle or the median radius of a land is the same as that of a groove.

Herein, the relative dimensions circumferentially are much more disproportionate. A spline is more like a thin blade compared to other splines and the grooves here. The groove occupies the great majority of the circumferential distance, and the spline occupies a relatively small fraction, typically about a fifth or less. This may be as little as one tenth of the circumference covered by splines, and ninety percent covered by grooves. However, this will depend on whether the spline and anchor are formed of a metal, a polymer, or bone.

Barbs, texturing, and grow-through regions may be used for resistance to sliding of bone with respect to an anchor along the longitudinal and axial direction of an anchor. Barbs and texturing may have an immediate effect against sliding, which is improved as bone growth continues. Grow-through areas initially provide insignificant resistance to axial displacement of bone along an anchor.

St. Venant's principle applies to most solid materials. Especially isotropic materials. Isotropic materials are materials in which the mechanical properties are the same in every direction. Cortical bone is typically isotropic. Cancellas bone, the central or marrow portion of bone is also typically isotropic. However, cancellas bone is much weaker and includes an almost sponge like hard structure filled in a mushy marrow, including vascular material. Thus, cancellas bone does not support force in any direction well. Cortical bone does support forces much better. Nevertheless, cortical bone, being essentially isotropic obeys the conventions of solid materials.

St. Venant's principle observes that stress or load (load being a force or a stress) begins distributing itself immediately from the point of application of the load out at a forty five degree angle. That forty five degree angle is a line, plane, or surface of principal shear stress. Maximum shear stress supportable is typically half the value of maximum compressive stress and maximum tensile stress supportable. Accordingly, driving screws into bone often has the effect of damaging the bone by forcing a shearing failure, flaking off chips of bone along the planes of principal shear. Accordingly, in accordance with the invention, drills, broaches, and the like are used to pilot and thereby reduce the stresses placed by anchors on cortical bone material.

Mohr's circle of stress defines maximum shear with respect to maximum compressive stress and maximum tensile stress. Mohr's circle of stress actually defines the principal stress line (in two dimensions), which moves away from the forty five degree plane depending on whether a second force other than a single direct compression or direction is being applied orthogonally to a first force.

A symmetric splining herein is used to define and indicate the fact that the grooves are a much larger portion of the circumference of an anchor than is a spline. Lands and grooves are not of similar dimensions.

Some terms used herein are not necessarily common. The term "pitch advance ratio" is a term coined herein to mean the circumferential distance (at maximum spline diameter) advanced by a single spline of an anchor divided by the overall length of an anchor. Thus, over the length of an anchor, a pitch advance will occur that is much less than the length, because the pitch is itself many times the length. It is typically less than Pi times the maximum diameter divided by five times the length. With fewer splines, it is not necessarily proper to use the number of splines to define pitch advance, because the issue is not dependent on number of splines, but the angle of progression circumferentially with advance axially.

The term "pitch length" means exactly the same as pitch length as pitch in screw threads. Pitch is the distance from one peak to the next peak along a threaded shaft, such as a screw or bolt. It is the distance that the screw or threaded rod travels for each rotation of 360 degrees by the head. Herein, the term "pitch advance angle" is a coined term meaning the angle that the helical spline makes with a plane that passes through the center line of an anchor, and the center line of the spline, at any point, measuring the angle that the ongoing helical path of that line makes with that plane at the outermost radius of the spline.

The term "pitch swept angle" is used to mean the total angular difference between a plane passing through the center line of the anchor and the center line of a spline closest to the head end or base of an anchor, and a plane through that center line of the anchor and the center line of the spline closest to the point end or leading end of the anchor. Thus, on a clock face, the pitch swept angle measures how much circumferential progress the spline makes over the length of that spline in an anchor.

Herein, the term plane will seldom apply to any physical part or location in a bone, other than an imaginary plane through certain points or lines. This is because bones are fundamentally rounded everywhere. They are not sharp and they are not angular. Accordingly, when two bones have curvature, one may pick a location on one bone and a corresponding location on another bone and one may draw a tangent plane to any surface. Any time the "plane" of a bone surface is spoken of, and it is not a plane, one may understand the plane to mean a tangent plane.

Referring to FIGS. 1A-1H, 1J-1K, 1M-1N, and 1P-1W, leaving the trailing letters "I," "L," and "O" unused to avoid confusion, a system 10 in accordance with the invention may be used to anchor one bone or bone structure (fragment, bone, or the like) to another. Various embodiments are shown, grouped as FIGS. 1A through 1G directed to cross-joint anchoring by multiple anchors, FIGS. 1H, 1J-1K, 1M-1N, and 1P-1Q directed to cross-joint anchoring by a single anchor, and FIGS. 1R through 1W directed to anchoring by an implant (metallic anchor) within and along the direction of the sacroiliac (SI) joint requiring fixation by the presence of the implant.

Typically, the bones 14 may be defined by the body part to which they pertain. The body may be used to define directions 11 with respect thereto (e.g., a human or an animal, but typically a human). In the illustrated embodiment, the direction 11*a* is a vertical direction 11*a*, while a lateral direction 11*b* may be thought of as a left or right direction.

In medical parlance, lateral is an expression meaning toward the left or right side of a subject outward. Meanwhile, medial is used to mean toward a center plane or center of symmetry of a subject. Here, lateral and medial will be used as in medical technology. However, a lateral direction 11*b* will be either left or right without regard to whether it is traversing in a lateral direction, with respect to the subject, or a medial direction. Finally, a direction 11*c* covers any forward or backward (anterior or posterior) direction with respect to a subject. Thus, a direction 11*c* refers to that front and rear, forward and backward, direction. Nevertheless, without a reference number, anterior and posterior maintain their same medical meanings, as do lateral and medial, as well as superior (up) and inferior (down).

Figure 5:
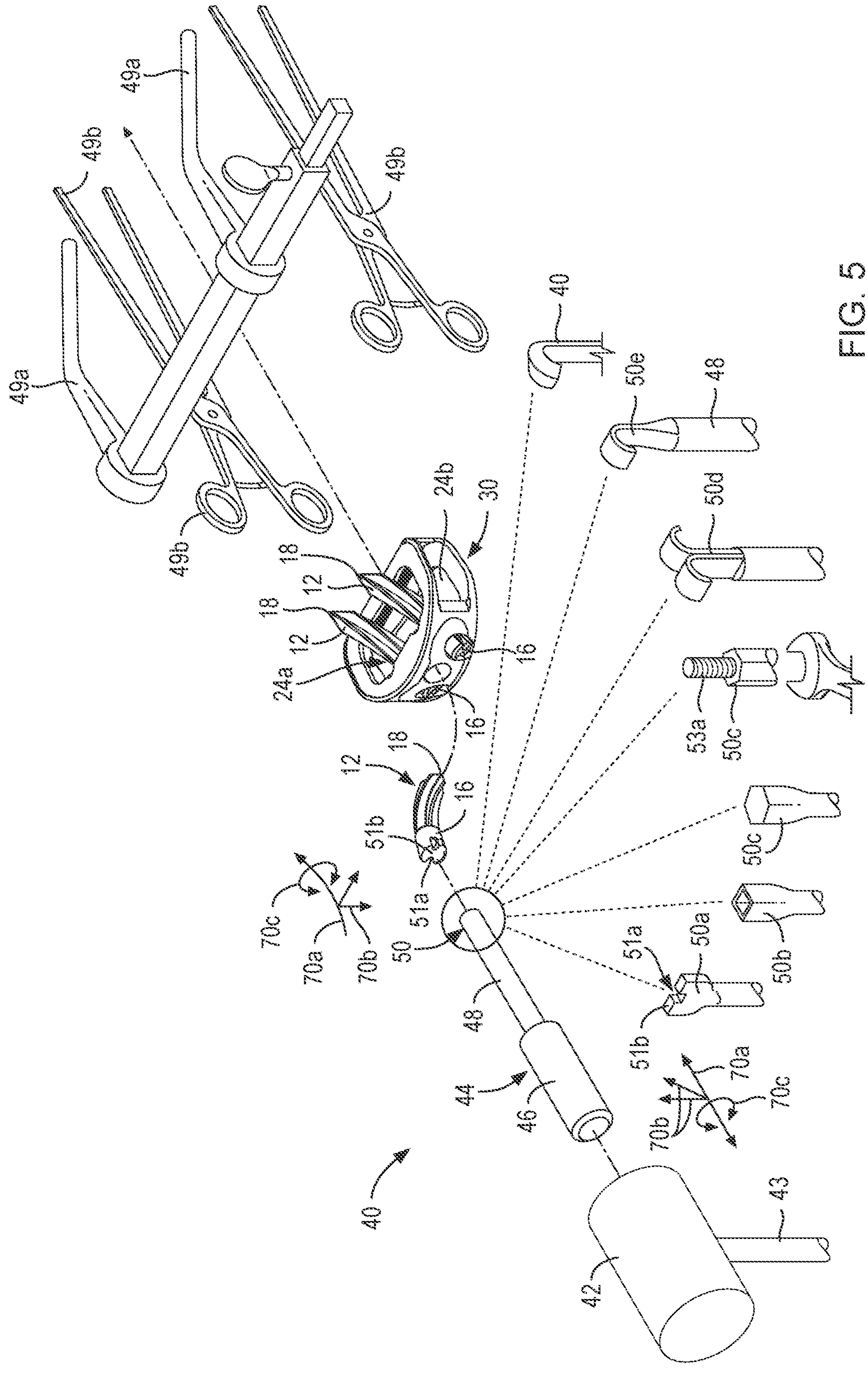
FIG. 5 is a perspective, exploded view of insertion tools, driving tools, anchors, optional frame, and distractors for installation of anchors.

An anchor 12 may be used in multiples with or without a frame 30 (see, e.g., FIG. 5). An anchor 12 may be of a pointed type 12*a* or of a hollow type 12*b*, also referred to as a cored type 12*b*. The helical splines 20 of the anchors 12, combined with an arcuate center line 17 (which is therefore not really a line 17 but a curve 17 or arc 17) are configured to twist and spiral along an axis not necessarily within the actual material of an anchor 12.

For example, in certain illustrated embodiment, bones 14 are exemplified by a sacrum 14*a* and an ilium 14*b*. These bones 14 may be referred to generally as bones 14 or by the trailing letters as 14*a*, 14*b*, designating specific instances 14*a*, 14*b* of particular items within the classification or type, here identified by the number 14 for bones 14. Herein, a reference numeral will refer to a type or class of items, while that same reference numeral with a trailing letter refers to a particular instance or configuration thereof.

The bones 14*a*, 14*b* may meet at a joint 15 or bone interface 15. In certain illustrated embodiments, that joint 15 is known as the sacroiliac joint 15. The joint 15 itself is actually formed of flexible, cartilaginous material. With age, deterioration, disease, inflammation, or the like, a particular joint 15 may become damaged, partially destroyed, and otherwise subject to excessive motion between the two individual bones 14*a*, 14*b* interfacing at the joint 15. Accordingly, a "fixation" (growing rigidly together) as that term is understood in orthopedic surgery, may be required. When the flexible joint 15 becomes too flexible, movement may cause abrasion and other damage between the bones 14*a*, 14*b*. They may be fused to rigidize and literally grow together across the joint 15. The joint 15 may be scraped to promote active bone healing and growth, and to remove ineffective cartilage and its debris remaining in the joint 15.

In a sacroiliac joint 15 as illustrated, anchors 12 may be inserted in a medial direction 11*b* through the ilium 14*b* into the sacrum 14*a* stopped only by the head 16 of the anchor 12 at the cortical type bone 14 near the outer surface of the bones 14*a*, 14*b*. A center line 17 of each anchor 12 is arcuate in shape in certain embodiments, straight in others. It may be or lie within a single plane, or may itself be helical in shape having a curvature circumferentially as well as radial along its length. Such an embodiment would reflect an extremely long pitch (several lengths of the anchor 12 per 360 degrees of revolution or progression of a spline 20 proceeding therealong and therearound). A very long-pitch, centerless screw (or any thread external to a central portion) may be thought of as a coil or wedge in operation. It does not necessarily have to include any actual matter along its center line, yet spirals about a central axis whether that axis is straight, curved, or helical.

Each anchor 12 regardless of its particular type 12*a*, 12*b* will typically have a point 18 or a leading edge 18 as its point, respectively. A pointed anchor 12*a* may have all splines coming together to form a specific point 18. Meanwhile, a hollow (cored) anchor 12*b*, having a tubular shape inside the splines 20, thereby leaves either a sharpened cutting edge 18 as a leading edge 18 to promote its progress through bone, or a hollow core to follow a K-wire as explained below. A pilot hole may be drilled for starting an anchor 12 and typically need only extend a short distance (typically about three diameters). Inasmuch as the helical splines 20 extend away from the center line 17 (curve 17), each anchor 12 rotates into position following its point 18 or leading edge 18 and the path dictated by the splines 20.

The splines 20 extend radially, and progress axially as well as angling circumferentially about the center line 17 of an anchor 12. In the pointed embodiment 12*a*, virtually the entire anchor 12*a* is formed of splines 20 extending radially and axially from and along, respectively, the center line 17. In contrast, the hollow anchor 12*b* has splines extending away from a lumen 22 or channel 22 defined by a wall 23 spaced from and traversing along the arcuate center line 17. From that wall 23 around the lumen 22, the splines 20 extend radially. Splines 20 have at least one of three possible mechanisms (texture, porosity, apertures) for encouraging securement thereto by the surrounding bone material.

For example, the lumen 22 may actually be accessible by elongated, somewhat rounded, oblong apertures 60. For example, apertures 60*a* through the splines 20 may permit bone grow-through individual splines 20. Likewise, apertures 60*b* through the wall 23 may permit bone growth inside and through the lumen 22 and connecting through those apertures 60*b* to bone growth between adjacent splines 20.

In addition, the splines 20, the wall 23, or both may be formed of a porous material (e.g., sintered metal) provided with a rough texture. Sintering provides particles of a metal that are partially melted at their interfaces in order to provide an atomic bond between adjacent particles, while still leaving small, often microscopic interstices therebetween. Accordingly, fluids, gases, and cellular structures inherent in bone 14 may actually grow into, through, or both, with respect to such splines 60*a* or walls 60*b*. Bone will typically grow-through the porosity itself as well as through any larger apertures 60. Thus, one may think of a grow-through-aperture 60 (GTA 60) as a comparatively larger aperture 60, although a porosity of much smaller effective diameter (defined as 4×area÷perimeter) through the solid material itself may also exist.

The texturing on any given component such as a spline 20 or wall 23 may provide resistance against shear. That is, a texturing provides concavities and convexities at the surface itself of a solid, thereby resisting the physical shearing that might otherwise occur between a hard, slick, slippery, smooth, and non-bonded surface of a solid with respect to adjacent material of a bone 14.

Figure 2:
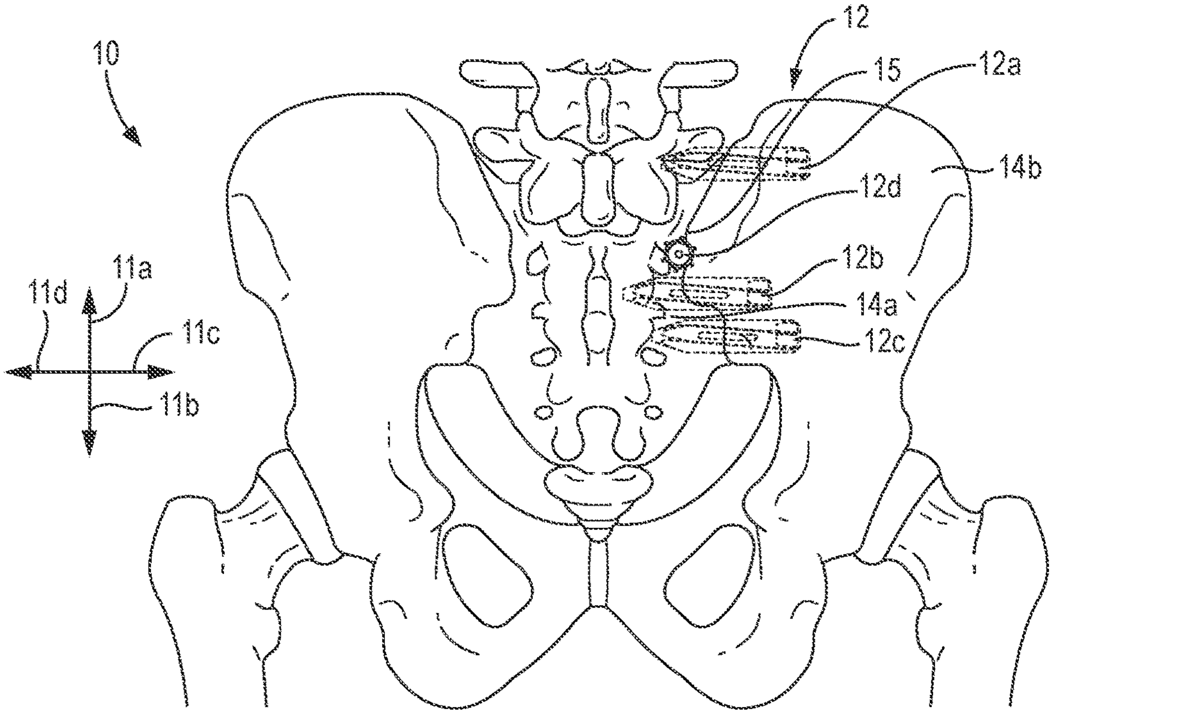
FIG. 2 is a posterior elevation view of a skeleton showing the sacrum, ilium, and the sacroiliac joint on both the right and left laterals (sides)
Figure 3:
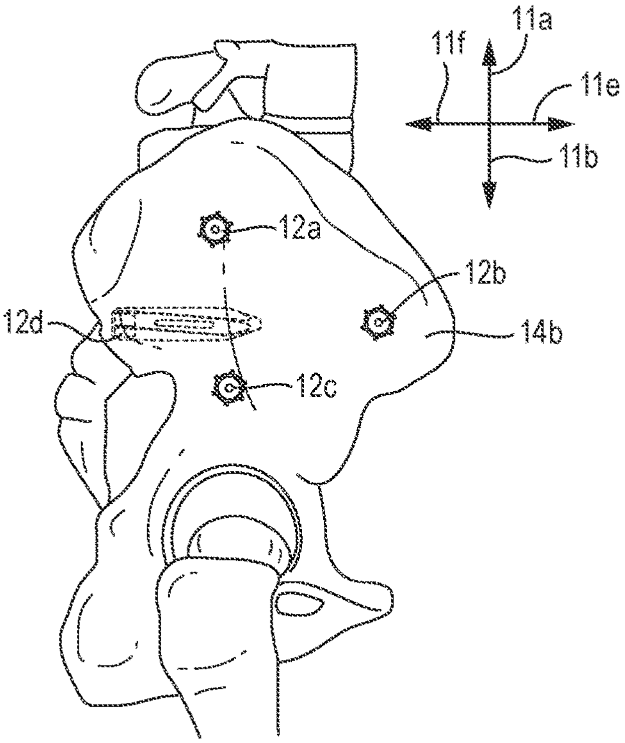
FIG. 3 is a right (lateral; viewing toward the medial direction) elevation view thereof illustrating the locations of the anchors.
Figure 4:
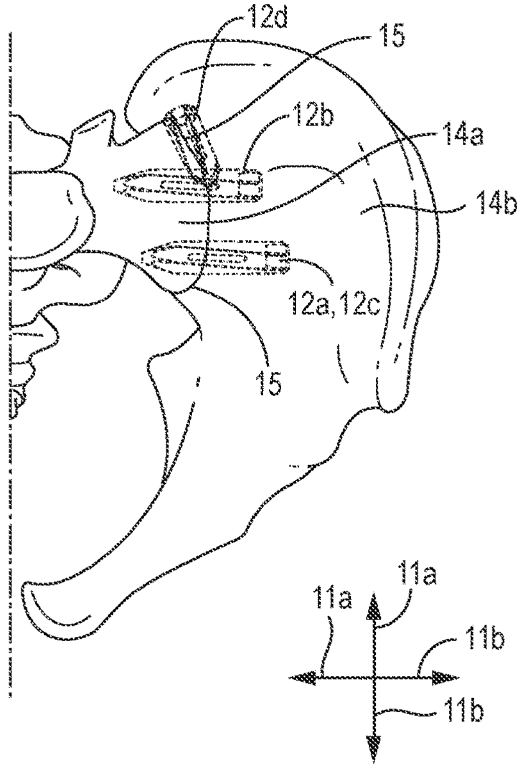
FIG. 4 is a top plan (superior) view thereof, showing only half the symmetrical structure.

Referring to FIGS. 2 through 4, an alternative embodiment of anchoring is illustrated. For example, in FIG. 2 is shown an ilium bone 14*b*. Also shown is a sacrum 14*a*. The demarcation between them is identified as a joint 15 or interface 15 between the two bones 14 identified as sacrum 14*a* and ilium 14*b*. The interface 15 or joint 15 is referred to as the sacroiliac joint 15. In this illustration are shown the several anchors 12.

The individual anchors 12*a*, 12*b*, 12*c*, 12*d* are instantiations of anchors 12, generally. In the illustrated embodiment of an installation of a plurality of anchors, various options are illustrated. For example, the anchor 12*a* is positioned high (superior) and posterior from the main hip joint. It may be located by identifying the posterior superior iliac spine (PSIS) which provides not only a navigation aid, but a positive location for positioning an anchor 12*a* that crosses the SI joint 15.

In order to provide resistance to relative rotation in anything like a vertical plane defining a joint between the sacrum 14*a* and the ilium 14*b*, additional anchors 12*b*, 12*c*, meaning either one or both, may provide restrictions against rotation about the anchor 12*a* by either of the bones 14*a*, 14*b* being anchored together by the anchor 12*a*. In certain alternative embodiments, one or more anchors 12*d* may be placed actually within the joint 15, thereby distracting the ligaments holding the sacrum 14*a* and ilium 14*b* together, inducing tension in the connecting ligaments and providing compressive pressure against each of the bones 14*a*, 14*b*. These anchors may be discussed in further detail hereinbelow.

Referring to FIG. 5, while continuing to refer generally to all figures, an apparatus 40 and method 40 are illustrated. That is, one may think of the illustration of FIG. 5 as representing both a method 40 of insertion and retraction as well as a set of hardware 40 for so doing.

A surgeon may use a mallet 42 to drive an anchor 12 into bone 14 with or without a frame 30. The mallet 42 provides an impact loading (momentum, impulse, time and force). Impact is a comparatively short event. The mallet 42 transfers momentum of its motion and mass into a handle 46, a cutting edge 18 or leading edge 18, such as a point 18. It will cut into both cortical bone and cancellous bone, subject to circumferential loading on the surfaces of the splines 20.

Momentum has "units" of mass times velocity. Impulse has units of force times time. Energy has units of mass times the square of velocity. The mallet 42 transfers energy and momentum into the handle 46 upon striking. The handle 43 is held by a surgeon to position and optionally to provide a certain rotational (circumferential) force urging the handle 46. The tool 44 will typically be rigidly secure between the handle 46 and shaft 48. The shaft 48 extends from inside the handle 46 to a point 50 that operates as an interface 50 with the head 16 of the anchor 12. The splines 20 are oriented to pass circumferentially 70*c* simultaneously. They present a much larger surface area (the sides or surfaces of the splines 20). That spline surface area will tend to urge the point 18 (regardless of whether actually pointed or hollow in the direction of the helical path of the splines 20.

The front or leading edge of each spline 20 must effectively cut through bone, but presents comparatively much less surface area. Accordingly, even cancellous bone will tend to rotate the anchor 12 by moving the splines 20 circumferentially as they move axially along their direction of travel.

A surgeon may apply a moderate force in a circumferential direction 70*c* around the handle 46, in the same direction that the splines 20 angle or drift as they progress from the head 16 toward the point 18. This will assist the slow rotation into local bone that may otherwise tend to absorb more momentum from the splines 20 in rotating the splines 20 moving along their trajectory.

Urging circumferential 70*c* rotation of the handle 46 is not required, but may result in less trauma to the bone 14 responsible to provide circumferential force rotating the anchor 12 along its path. Of course, the point 18, terminating at the end of the arc that represents the center line 17 (center curve 17) through the anchor 12, will tend to arc along that path. Whether circular or spiral in and of itself, the path is followed by the splines 20. Possible rotational 70*c* urging of the handle 46 by a surgeon may help.

Again, a frame 30, of any suitable shape for the space to be accommodated, may be used or not. In certain embodiments, the distractors 49*a*, 49*b* may be used to move tendon, muscles, or other tissue layers from an area into which a frame 30 is to be placed. Distractors are well known in the surgical art and need not be described in detail here. Suffice it to say that they operate in an opposite direction from forceps to spread tissues apart clearing space for a procedure to take place. Such a procedure inserting a frame 30 past tissues into a joint 15 between bones 14. Thus, the illustration of FIG. 5 shows various options, not all of which would be extant in a particular procedure.

The points 50 or interfaces 50 may be made in various configurations. For example, the point 50*a* has a slot 51*a* for receiving a crossbar 52 flanked on each side by a key 51*b* (slot 51*a*, key 51*b*, crossbar 52*a*, and the relief 52*b* in the illustrated embodiment of a head 16). For installation or insertion of an anchor 12, the point 50*a* may be suitable. In other embodiments, a square point 50*b* may be used to fit into the head 16. Alternatively, a hexagonal or other commercially available point 50*c* may be relied upon. The function of each of the heads 50 is to apply the impact load from the mallet 42 through the tool 44 and into anchor 12 along its axial direction 70*a* and, optionally apply a slight torque circumferentially 70*c*.

The engagement by a key 51*b* in a key way 52*b* or relief 52*b* may engage to provide a certain circumferential 70*c* torque. Torque is a force at a distance and therefore has units of force times distance. Axial force plus torque are suitable for progressing the anchor 12 both axially 70*a* along the arc of the center line 17 (center curve 17) and circumferentially 70*c* along the helical path described by the splines 20.

The points 50*d*, 50*e* may be used for insertion, but may provide additional features including a threaded stud 53*a* and a hook 53*b*. The threaded stud 53*a* may actually rotate with respect to the hexagonal point 50*c* in the device 50*d*, thereby permitting engagement of the female thread inside the head 16, for extraction. The hexagonal head 50*c* may penetrate into the head 16, after which turning a knurled handle, a T-handle, or another mechanism allows the threaded stud 53*a* to advance forward with respect thereto out of the hexagonal head 50*c*.

A polygonal (e.g., hexagonal) head 50*c* may provide secure engagement for rotation in a circumferential direction 70*c*. The threaded stud 53*a* provides secure axial 70*a* engagement with the head 16 in order to draw back along the center line 17 (center curve 17). The handle 46 may be rotated in an opposite circumferential direction 70*c* from that of insertion. Accordingly, the anchor 12 may be removed by pulling and rotating. This will be on the same trajectory on which it passes into bone 14 to which it anchors. The significance of the threaded stud 53*a* and the hooks 5*d*, 50*e* is that axial tension is not employed during the insertion process. Insertion needs only force or impact applied in an axial direction 70*a*, although some torque may assist.

Removal or loosening of the anchor 12 by the bone 14 does not occur readily because the axis 17 is curved not straight and the splines 20 are not aligned with it. That curve 17 has been modified in a helical path driven or guided by the splines 20. Accordingly, a force near the head 16 trying to force apart adjacent bones 14*a*, 14*b* is resisted by every spline 20 at its angle. That angle is not aligned with the axial direction 70*a* at the head 16 itself. Rather, along the entire length of the splines 20 the direction of force is continually changing.

The orientation of each spline 20 surface changes along its entire length to secure the splines 20 and thereby the entire anchor 12 in bone 14, even cancellous bone. Pitch is pitch. Long pitch is a pitch longer than a length, where length is more than twice maximum diameter. Very long pitch or extra-long pitch means pitch is several lengths, typically greater than two and more typically greater than five, with the same or lower ratio of diameter to length. One will note that due to the extra-long (multiple anchor 12 lengths) pitch, the mallet 42 and tool 44 may drive the anchor 12 into the bone 14. After that, the splines 20 provide a comparatively large surface area engaged at a comparatively modest force exactly the opposite effect as a conventional screw which tends to shear any cancellous bone into which it is anchored.

In fact, many conventional screws operate more like a sheet metal screw. A sheet metal screw passes through a single thin layer that is typically considerably less than one inch in thickness. One pitch is the difference in length between the crest of one thread and an adjacent thread. Not only do the splines 20 in accordance with the invention put less pressure on the cancellous bone, that pressure is distributed over a substantially larger area. There is not a location where the shear of a few threads can accumulate in close proximity to one another and at the exact same diameter as one another, in that nearly the same axially 70*a* location can be pulled through cancellous bones. Thus the coring out by simply stripping the threads cut into the cancellous bone is avoided.

Figure 6A:
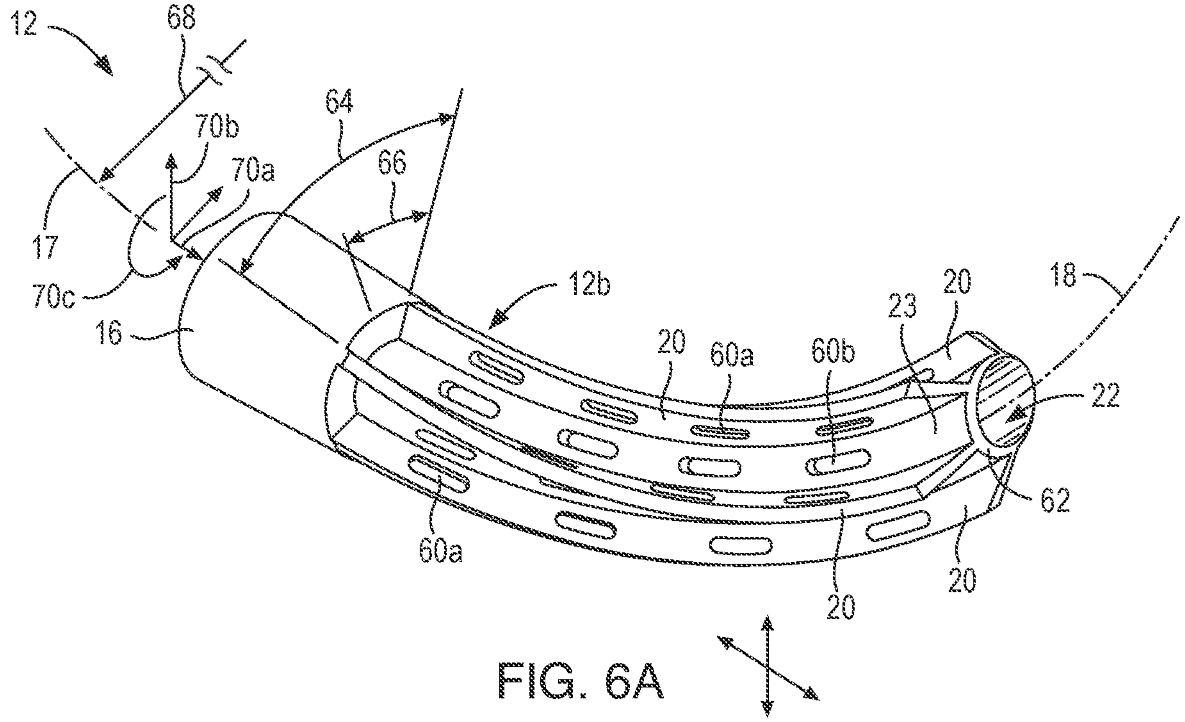
FIG. 6A is a perspective view of one embodiment of an anchor viewed from a distal end.
Figure 6B:
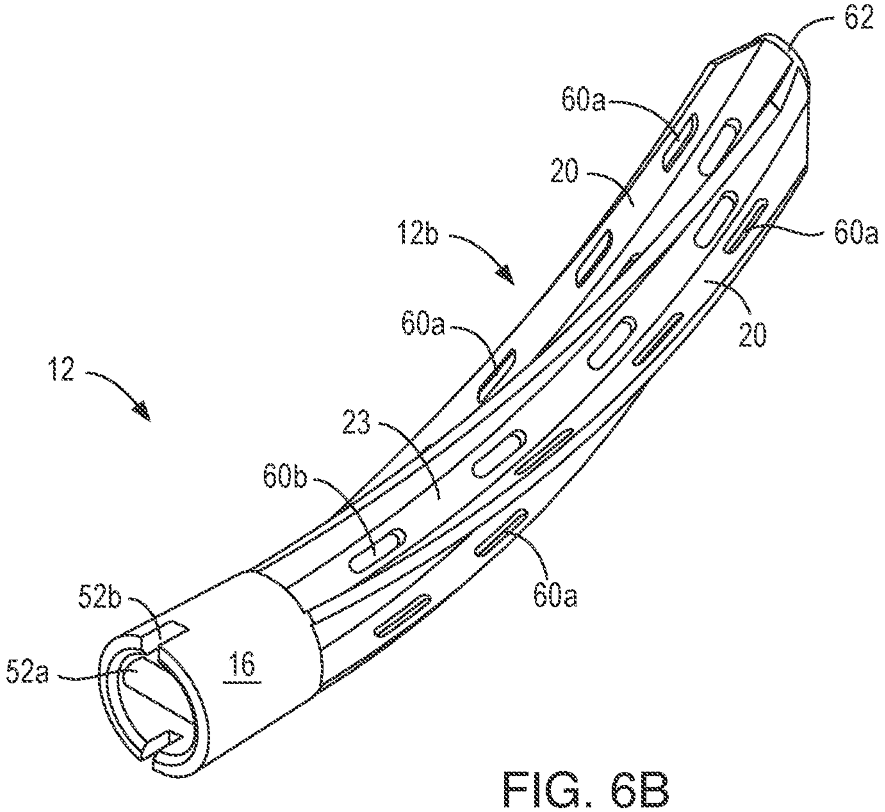
FIG. 6B is a perspective view from a proximal end of the cored type of splined anchor in one embodiment in accordance with the invention.
Figure 6C:
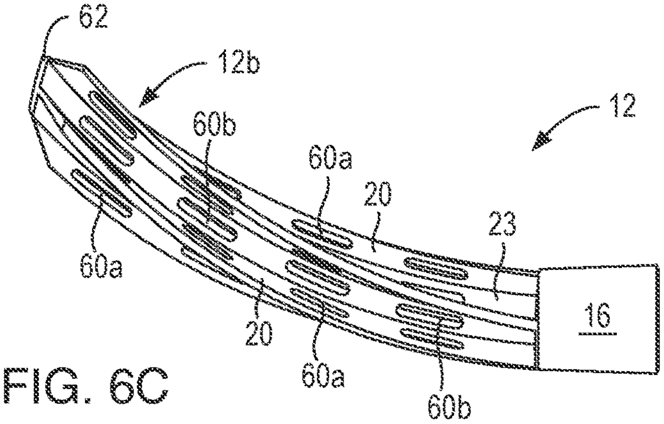
FIG. 6C is a proximal end view thereof.
Figure 6D:
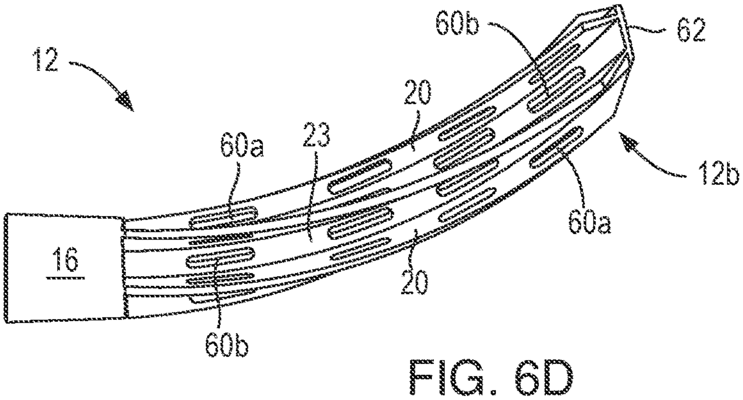
FIG. 6D is a distal end view thereof.
Figure 6E:
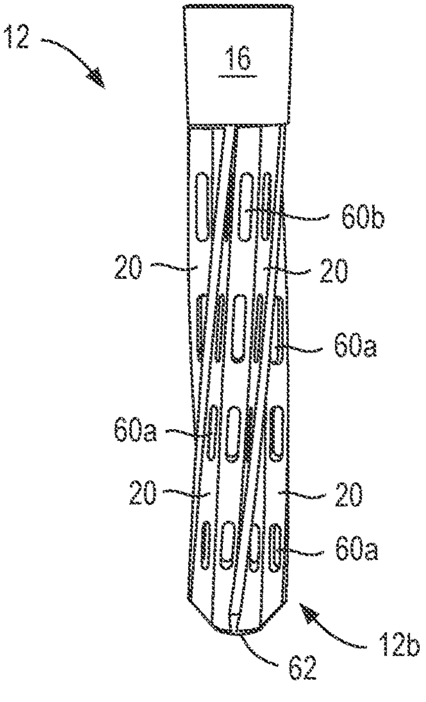
FIG. 6E is a side elevation view taken in a plane resulting in a straight envelope (outer boundary) and center curve.
Figure 6F:
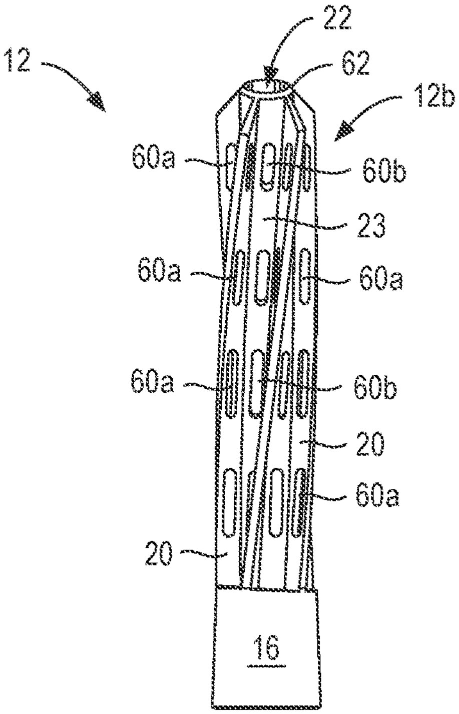
FIG. 6F is a side elevation view thereof taken in the plane in which the anchor central axis lies within a plane containing the curve.
Figure 6G:
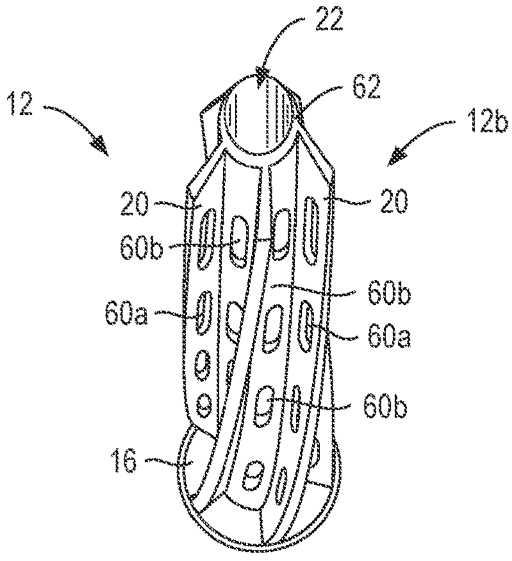
FIG. 6G is a cross-sectional view along a central axis near a distal end thereof.
Figure 6H:
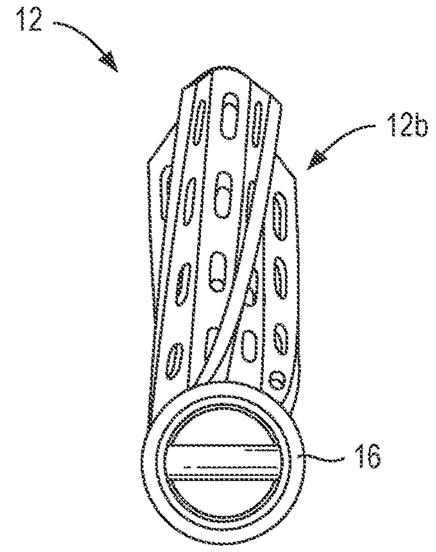
FIG. 6H is a cross-sectional, end view thereof near a proximal end thereof.

Similarly, the hook type point 50*e*, similarly to the stud type point 50*d*, may engage the head 16, this time by a crossbar 52*a*. Meanwhile, the shaft 48 fits into the head 16 of the anchor 12. For example, the hook point 54*b* may pass into the head 16, past a crossbar (as in FIG. 6H) then may be drawn backward in the axial direction 70*a*. It may thus engage the anchor 12 to urge rotation in a circumferential direction 70*c*, as well as drawing backward in an axial direction 70*a*.

Referring to FIGS. 6A through 6G, as well as FIGS. 7A-7H and 7J-7K (again not using I, L, or O, in order to avoid confusion), an anchor 12 in accordance with the invention may have a pointed configuration 12*a* or a hollow (tube-like core, or coring) configuration 12*b*. In the illustrated embodiments, one will see that the proximal end is formed into a head 16 for engaging a tool 44 for insertion or installation.

The tool 44 may have any of the engagement mechanisms 50*a* through 50*e* for driving, drawing, or both against the head 16. It may urge the point 18 or cutting edge 18 axially along the center curve 17 or center line 17. Progress along the center curve 17 necessarily drives the distal end of the anchor 12 at the leading edge 18 or cutting edge 18 (also called the point 18) along the axial direction 70*a*, where directions 70 are all with respect to the axis 17 or center line 17 through the anchor 12 along a curve 17.

Like the frames 30, the anchors 12 may be formed of a sintered material providing a porosity that can be penetrated in a straightforward manner by cellular material within a bone 14. Following insertion of the anchor 12, with the leading edge 18 or point 18 advancing first into the bone, and typically terminating when the head 16 abuts the cortical bone 14 or as shoulder countersunk therein. That is, the head 16 may be countersunk into cortical bone 14. There is substantial benefit to leaving the head 16 outside the cortical bone 14 material in order that the splines 20 may be stabilized by the cortical bone 14, and so that the head 16 may secure one portion of bone 14 to another.

To that end, a grow-through-aperture 60 or GTA 60 may be provided in any suitable portion of an anchor 12. For example, in the illustrated embodiments, a GTA 60*a* provides an opening 60*a* through a spline 20. It may be dressed or shaped to promote engagement with bone growth therethrough. Similarly, the wall 23 of the spline 20, surrounding the lumen 22 or channel 22, may likewise be perforated with GTA's 60*b* at some suitable length and width, spaced apart at an effective, intermediate spacing therebetween.

One will note that the helical trajectory of an anchor 12 upon entry into bone 14 is guided by the splines 20, which may in turn be guided or not by apertures 32 in the posterior wall 36*a* of a frame 30. Regardless, a suitable amount of urging in a circumferential direction 70*c* while driving or malleting an anchor 12 into place, the point 18 and splines 20 will move the distal end in accordance with the forces applied in a circumferential direction 70*c* by the splines 20 themselves. Thus, a combination of the splines 20 moving against already penetrated cancellous bone 14, as well as the outer cortical bone 14, will urge the rotation about the center curve 17, even as the arcuate shape of that center curve 17 within the anchor 12 imposes its own arcuate direction on those helical splines 20. That is, moving forward, the arcuate shape of the center curve 17 and consequently the anchor 12 will tend to move in an arc from a point of insertion. Meanwhile, the splines 20 and optional urging on the handle 46 in a circumferential direction 70*c* will also move that point 18 on a helical path combining the arcuate shape along the center curve 17, and helical shape (and resulting orientation) of the several splines 20.

To a certain extent, the angle 64 between adjacent splines 20 may be selected according to engineering principles. Likewise, the overall radial 70*b* dimension or height in a radial direction 70*b* of each spline 20 may be balanced against the diameter across the lumen 22. For example, the embodiments of FIGS. 7A through 7H and 7J through 7K, include no lumen 22 and no wall or core (e.g., cylindrical or circular tube-like structure) from which the splines 20 extend. However, in certain embodiments, a comparatively large fraction of the overall dimension across an anchor 12 in a radial direction 70*b* may be balanced between the diameter of the lumen wall 23, against the altitude or radial 70*b* extension of those splines 20 away from that lumen wall 23.

In practice, the curvature of the path of leading edge 18 or point 18 is a combination of the center line 17 or center curve 17 and the helical disposition of the splines 20. This results in the adjacent bones 14*a*, 14*b* across a joint 15 being held firmly. The force direction across the joint (perpendicular to) a plane of the joint 15 is almost never aligned with the majority of area of the splines 20, especially following installation.

Figure 7A:
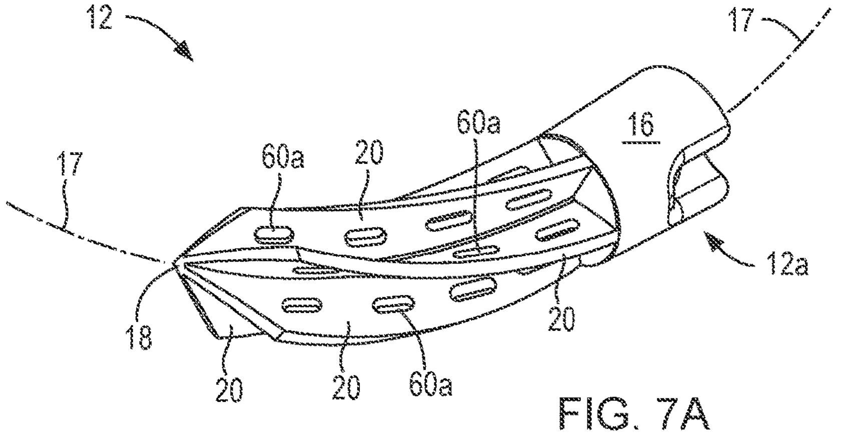
FIG. 7A is a perspective view from a distal end of an alternative embodiment of an anchor in accordance with the invention.
Figure 7B:
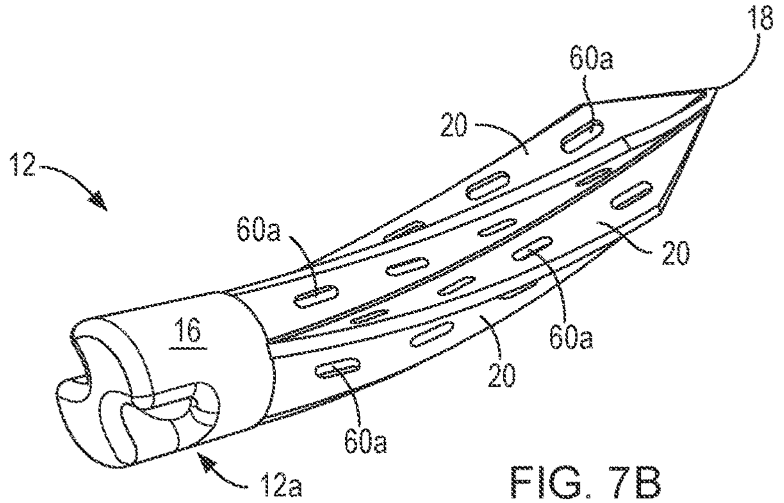
FIG. 7B is a perspective view from a proximal end thereof.
Figure 7C:
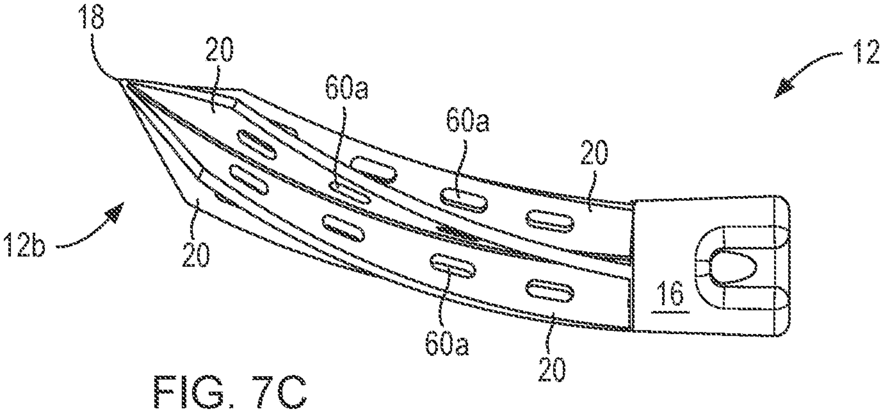
FIG. 7C is an end view thereof from a distal end.
Figure 7D:
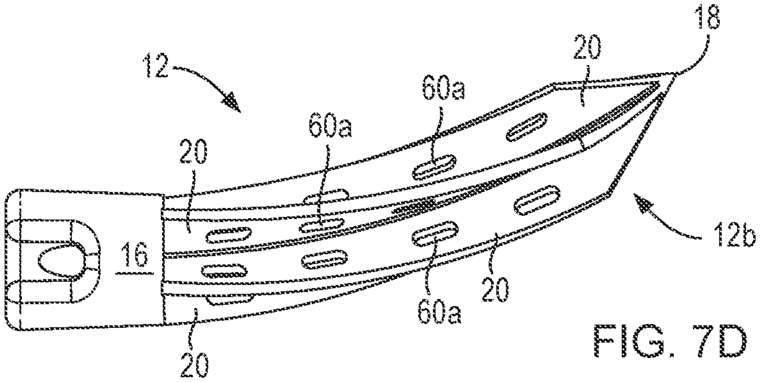
FIG. 7D is an end view thereof from a proximal end.
Figure 7E:
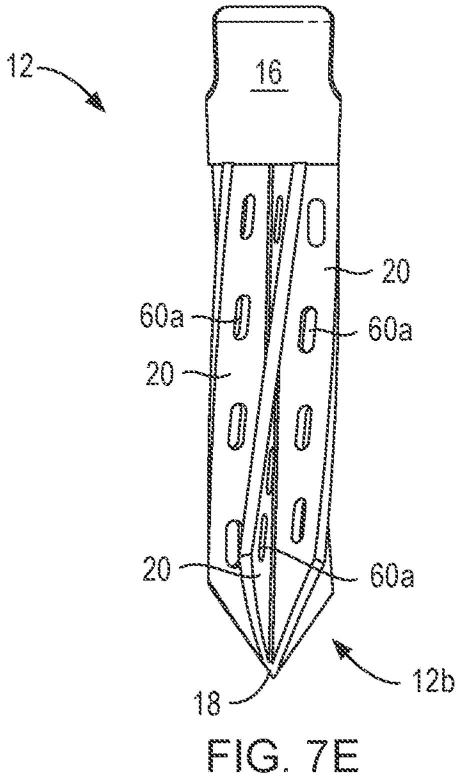
FIG. 7E is a side elevation view taken in a plane containing the curvature of the curved central axis through the anchor.
Figure 7F:
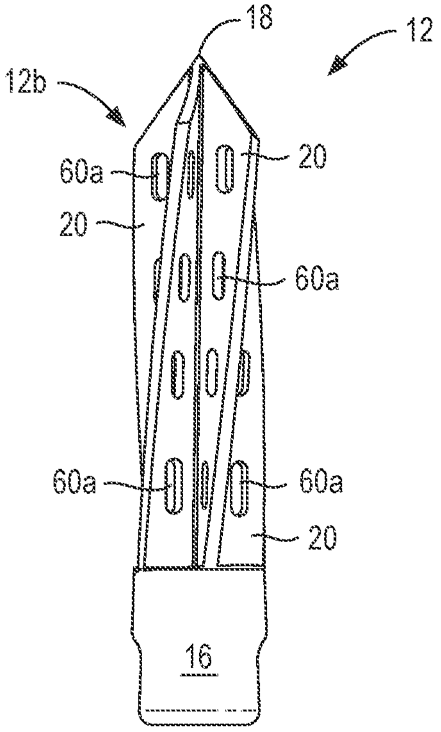
FIG. 7F is a side elevation view in a plane perpendicular to the curvature of the curved central axis.
Figure 7G:
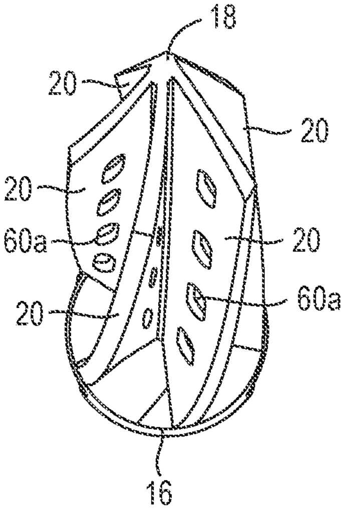
FIG. 7G is a cross-sectional view thereof taken near the distal end.
Figure 7H:
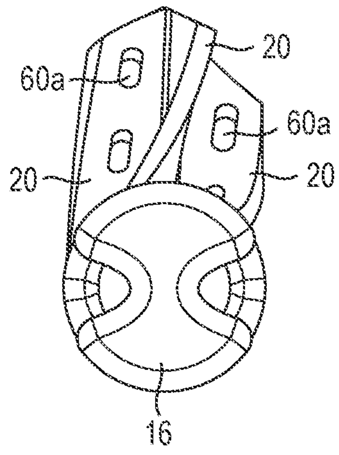
FIG. 7H is a cross-sectional view thereof taken at the proximal end thereof.
Figure 7J:
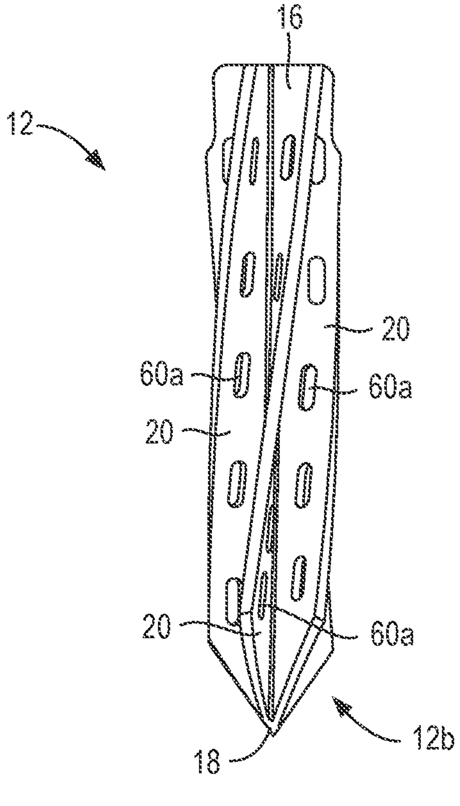
FIG. 7J is a side elevation view of an alternative embodiment of an anchor lacking a solid head with a circular or other cross-section, and therefore lacking a "bulkhead" at the proximal end of the splines to act as a stop in a frame or in cortical bone, and, being taken in a plane containing the curvature of the curved central axis through the anchor, corresponds to the view of FIG. 7E of the "headed" embodiment.
Figure 7K:
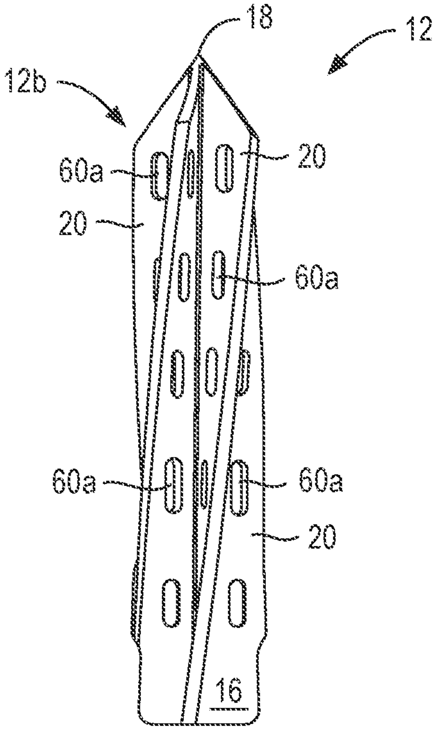
FIG. 7K is a side, elevation view thereof in a plane perpendicular to the initiation of a spline at the head with the point upward.

Referring to FIGS. 7J and 7K, almost all of the foregoing information with respect to FIGS. 7A-7H may be applied in a more-or-less "headless" variety of anchor 12. In the illustrated embodiment, a tool may simply fit the splines 20 (in any embodiment of spline 20 discussed hereinabove) at a proximal end thereof. The tool may serve as the only "stop" for insertion of the anchor 12. In fact, a tool may be contemplated that would not present enough cross-sectional area perpendicular to the direction of motion to even operate as a stop.

For example, a tool may fit between the splines 20 like pieces of a pie divided by the splines. Alternatively, a tool may simply engage a few splines with thin clips leaving the space largely open between splines. All the features and function of this description of FIGS. 7J and 7K may be properly applied to almost all hollowed anchors 12*b* as well as anchors 12*a* by suitable engineering modifications. Therefore an insertion tool may fit into the central aperture 22 at the proximal or "head 16" end, even without a solid head 16 other than what the splines 20 and wall 23 provide. Alternatively, note that trimming the outer diameter of the splines 20 may provide space to fit an insertion tool over the reduced diameter of splines, leaving a completely hollow center in the insertion tool.

In other embodiments, a distal end of an insertion tool may fit inside the aperture 22, with small fingers or simple interfering stubs extending outside the wall 23 and aperture 22. Those may engage splines to support rotational forces without presenting substantial resistance against the insertion tool following the anchor 20 as the anchor moves a distance longer than its length into or across a joint. Even the insertion tool may be cored (hollow), having a mere rim fitting inside and outside the aperture 22, and having slots to receive splines 20. Such a tool presents little more resistance to movement forward, permitting insertion along a path much longer than the anchor 20 itself. Thus longitudinal positioning of an anchor 20 need not be limited by a head 16 at a proximal end of the anchor 20.

Thus, for example, certain SI joint fusions relying on an anchor 12 passing somewhat parallel to the adjacent faces of the sacrum and the ilium may rely on an insertion path longer than the anchor 12 itself. Neither the cortical bone nor the tool need stop the anchor, lacking a "bulkhead-like" face to stop forward progress of the distal (point 18) end.

In all of the foregoing discussion of surface roughness or "texturing," one should remember that shear forces along a slick, smooth, hard surface of a spline are going to be comparatively weak (compared to a textured surface having mechanical engagement of interfering projections "sticking out" from the nominal surface). On the contrary, just as apertures 60 engage tissues for through growth, texture provides concavities and convexities for "on growth." However, the surface shear forces (slip of any bone tissue with respect to a hard, artificial surface of an anchor 12) are augmented by local compressive and tensile forces on the bone material, supported by mechanical tension, compression, and shear forces in the texturing features themselves. The presence of texturing provides immediate "purchase" or grip. Nevertheless, the adhesion and filling in by "on-growth" tissues engages the structure of the bone and projects or transfers true shear stress away from the anchor 12 and out into the tissues farther away but mechanical bound to the tissues grown onto the concavities and convexities of the texturing features.

Thus, in general, it is contemplated in a system and method in accordance with the invention that sintering, sputtering, casting, forging, printing, or other manufacturing techniques may be relied upon to provide not only through-apertures of any type (through tortuous paths of sintered grains of metal, for example, or formed as large open apertures 60 in splines), but surface texturing along any surface (inside, outside, etc.) of an anchor. The healing by macrophages in the first days after a surgery (and implant) will thus provide additional resistance to pull out, in addition to such compressive loading provided by the nature of the helical splines radiating outward from an arcuate "centerline" of an anchor 12.

In addition to tensioning of the anchor 12 providing compression in the tissue, the anchor provides a friction lock and a fast developing shear-engagement lock of the anchor 12 in place. That is, the tension in the anchor 12 due to its committing to a curvature of its centerline, and then being forced to rotate along the path of its helical splines, results in a compression of tissues behind (considering insertion path direction to be forward) the anchoring splines 20. Meanwhile, those splines 20, or rather their texturing will shear and smear tissues forward, which then engage immediately by friction against pull out. Healing then immediately begins to engage and lock in all that texturing, splines, and (apertures of every type) by intimate contact and growth filling concavities.

Figure 8A:
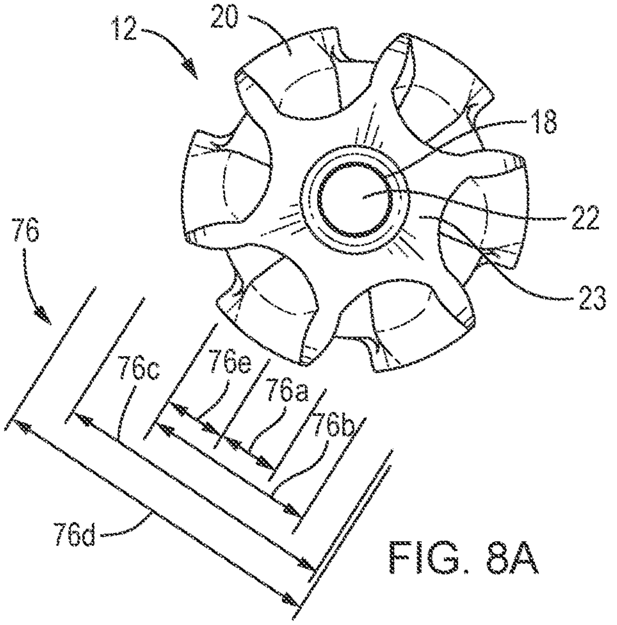
FIG. 8A is an end elevation view of the point or leading edge end of an anchor in accordance with the invention.
Figure 8B:
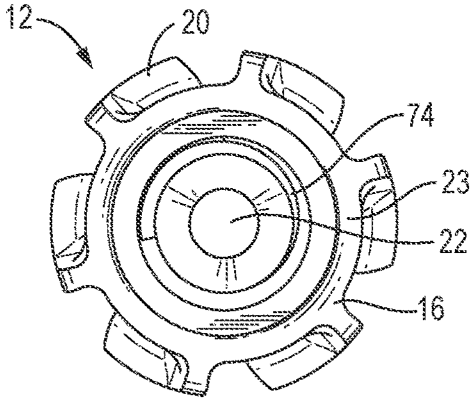
FIG. 8B is an end elevation view of the head end thereof.
Figure 8C:
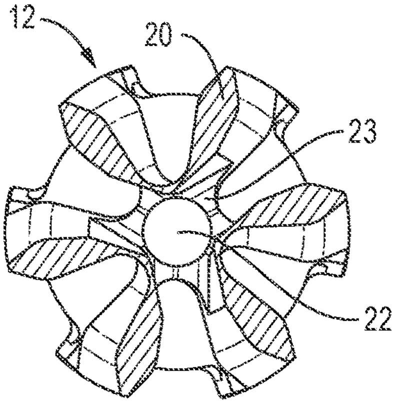
FIG. 8C is a cross sectional view thereof midway along the length of the anchor.

Referring to FIGS. 8A through 8C, one will see end views of an alternative embodiment of an anchor, this having a hollow core or hollow tube structure from which extend the individual splines 20. The core 23 which may be thought of as a wall 23 surrounding a channel 22 or lumen 22 constitutes a tubular structure from which the splines 20 extend radially from a center line 17 and extend axially (longitudinally) and circumferentially along an outer "surface" of the wall 23 or core 23. In FIG. 8A is seen the point end or leading end of the anchor 12 that will effectively be first to penetrate either the bones 14*a*, 14*b* or the joint 15. If the joint 15 is penetrated along its own direction (effectively parallel, although the joint 15 is not planar nor flat) the splines 20 will still cut into and fix themselves within the cortical bone of the sacrum 14*a* and ilium 14*b*. However, when an anchor 12 is used to penetrate across the joint 15 as illustrated by the anchors 12*a*, 12*b*, 12*c*, then the anchor 12 will be piloted in by drilling, broaching, and so forth as needed to reduce the trauma caused by penetration of the anchor 12 and particularly its splines 20.

One will note that the illustration of FIG. 8B shows the head end or base end of the anchor 12. In this view, the engagement 74 is shown internally to the wall 23 or core 23 from which the splines 20 extend. Thus, the head 16 stands opposite to the leading end 18 or leading edge 18, which may also be considered a point 18, although no actual point exists at the center line thereof.

In FIG. 8A, a dimension 76*a* is matched by a symmetrical dimension 76*e*. Meanwhile, the dimension 76*b* provides the distance between two adjacent splines 20 as measured at any point, and here shown as measured at the base or head end. Meanwhile, the dimensions 76*c* represents the outermost diameter of the core 23 or wall 73 from which the splines 20 extend. The dimension 76*d* represents the overall outer diameter of the entire anchor 12 at the outermost diameter of the splines 20. The lumen 22 in this illustrated embodiment is sized to fit around and slide along a K-wire guide as described hereinbelow.

Thus, the cross section taken between the two ends, the point end 18 and the head end 16, shows the effective cross ends of the material in the splines 29, themselves, and the wall 23.

Figure 9A:
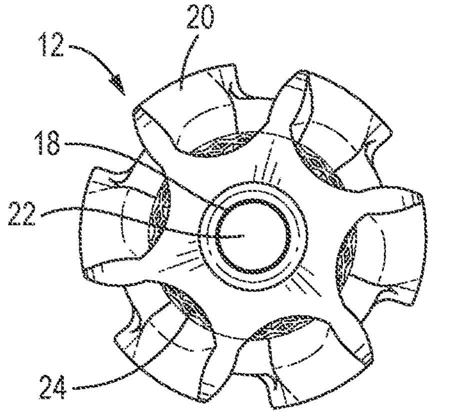
FIG. 9A is an end elevation view of the point or leading edge end of an anchor in accordance with the invention.
Figure 9B:
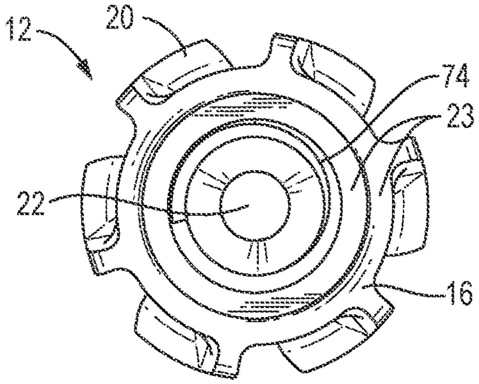
FIG. 9B is an end elevation view of the head end thereof.
Figure 9C:
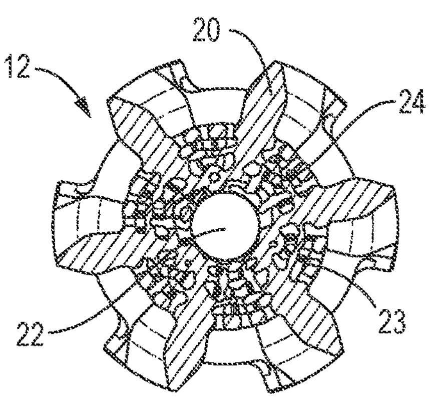
FIG. 9C is a cross sectional view thereof midway along the length of the anchor, illustrating the porosity of the core of the anchor from which the splines extend away.

Referring to FIGS. 9A through 9C, an alternative embodiment providing grow-through areas 24 formed in a porous wall 23 or core 23. In these illustrations, the point end 18 operates exactly as the point end 18 of FIG. 8A. Similarly, the engagement at the head end 16 also may operate in exactly the same way as that of FIG. 8B. However, the embodiment of FIGS. 8A-8C may be formed of any material, including a non-reactive metal, a polymer, a filled polymer, or actual bone. A small porosity or lattice work 24 of apertures 24 as grow-through areas 24 are largely impractical if the anchor 12 is machined from actual bone capable of promoting growth through and around by the subject or patient.

Figure 10A:
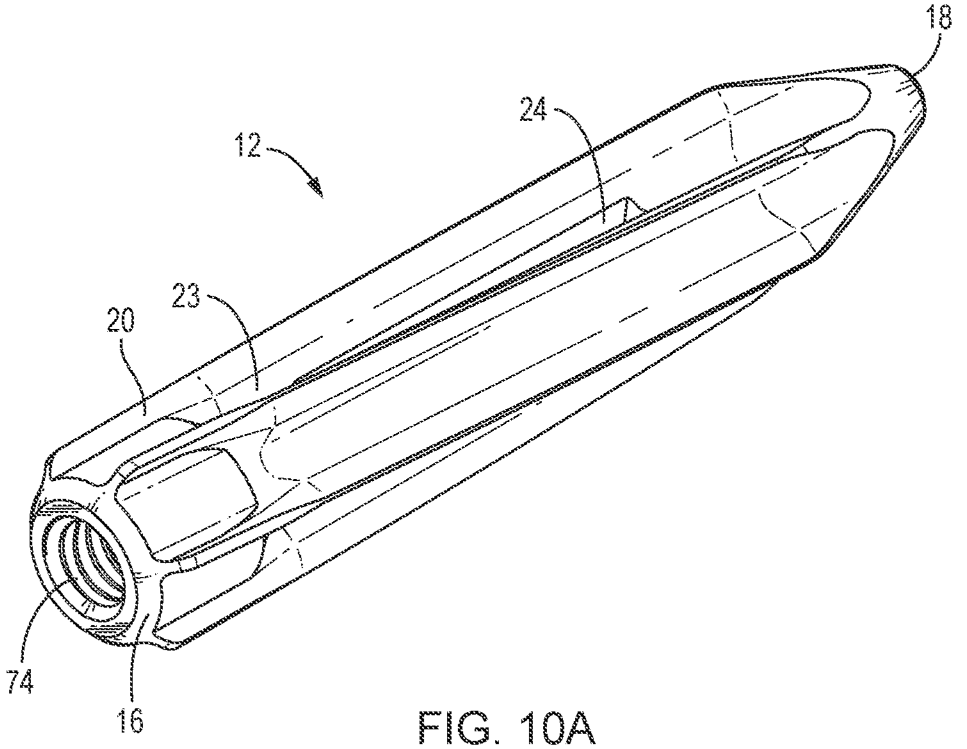
FIG. 10A is a perspective view of the embodiment of FIGS. 8A through 8C.
Figure 10B:
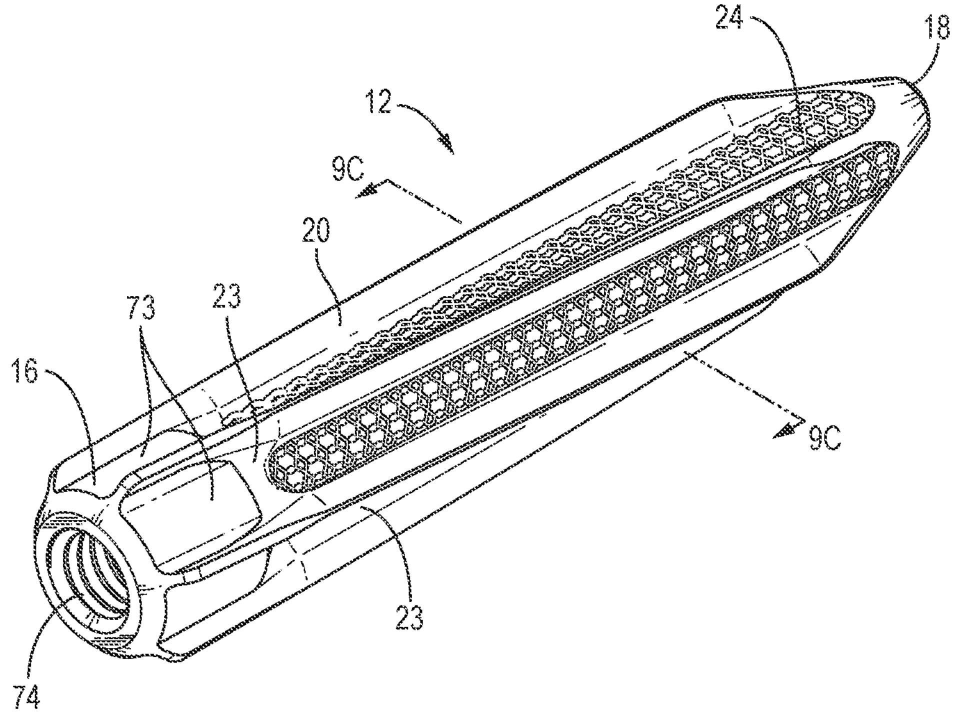
FIG. 10B is a perspective view of the anchor of FIGS. 9A through 9C, illustrating a lattice-like porosity.

Referring to FIGS. 10A and 10B, one may see that in the former embodiment, a single large aperture 24 forms effectively a window 24 as a grow-through area 24. It has been found that such large windows 24 may affect the dimensional stability and the structural strength of an anchor 12. Accordingly, such windows 24 as illustrated in FIG. 10A should be kept to a length that provides for support between adjacent portions of the wall 23 between splines 20. Engagement 74, here shown as threads 74, may be fabricated in a process such as centering, casting, molding, forging, or 3-D printing, even as metals, polymers, filled polymers, structurally reinforced polymers, and the like.

Comparing now the embodiment of FIG. 10B of that of 10A, a lattice work 24 of apertures 24 held together by the same material as the remainder of the wall 23 or core 23 supporting the splines 20 is illustrated. This lattice work 24 of apertures 24 may be formed in any suitable manner, including centered solid pieces that have a porosity through them, or specific patterns of lattice work providing apertures of a regular size or multiple sizes. One may note that the head 16 may include a transition 73 that thickens the wall 23 toward the head end 16 in order to support and provide clearance sufficient to form threads 74 as an engagement mechanics 74 to connect the anchor 12 to suitable tools for insertion.

Referring to FIGS. 11 through 15, various lengths of anchors 12 are illustrated. In general, it is proper to speak of an aspect ratio when discussing the relative dimensions of any physical object. Accordingly, each of the illustrated anchors 12 includes a length, an outermost diameter around the outside of all splines 20 and outside diameter of the wall 23 or core 23 as well as an inside diameter of the wall 23 constituting the diameter of the lumen 22 or channel 22.

An aspect ratio is simply the ratio of two dimensions. Accordingly, since an aspect ratio is one distance divided by another distance the aspect ratio has no units, that is, no dimensional name. An aspect ratio is a "dimensionless" number as well understood in the engineering arts and the technical arts of manufacturing and fabrication. In the illustrated embodiments, each of the anchors 12 includes or may be characterized by aspect ratios.

For example, the diameter of the lumen 22 compared to the diameter or outer diameter of the wall 23 is an aspect ratio of two diameters. Similarly, the diameter of the lumen 22 or the diameter of the wall 23 may be divided by the outer diameter around the splines 20 to determine yet another aspect ratio of comparative diameters. Similarly, lengths may be compared. For example, any of the foregoing diameters may be compared to the length of a particular anchor 12 thus defining an aspect ratio of diameter to length.

One will note that the aspect ratios may be reversed, such that length is divided by a particular diameter. One use of aspect ratios is to characterize a distance or a proportionality between dimensions of an object in the abstract, rather than specifying any particular set of measurements. In the physical arts of engineering, manufacturing, fabrication, and the like, these aspect ratios may be very useful. Moreover, performance is often related to aspect ratios, "dimensionless" numbers characterizing an object. It is typically beneficial to define or characterize an object by an aspect ratio that effectively equals a smaller dimension divided by a larger dimension. In this way, the aspect ratio will vary between zero and one. It cannot exceed one where the longest dimension in the object is the deviser.

Figure 15:
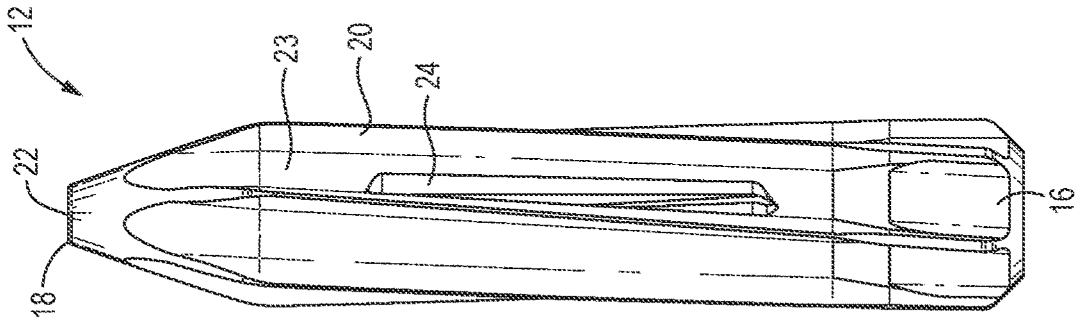
FIG. 15 is a perspective view of the anchor of FIGS. 13 and 14, further rotated to provide another view of the window or aperture providing a grow-through region, remembering that texturing and apertures may be made through the wall of the core as well as selectively through the splines.
Figure 14:
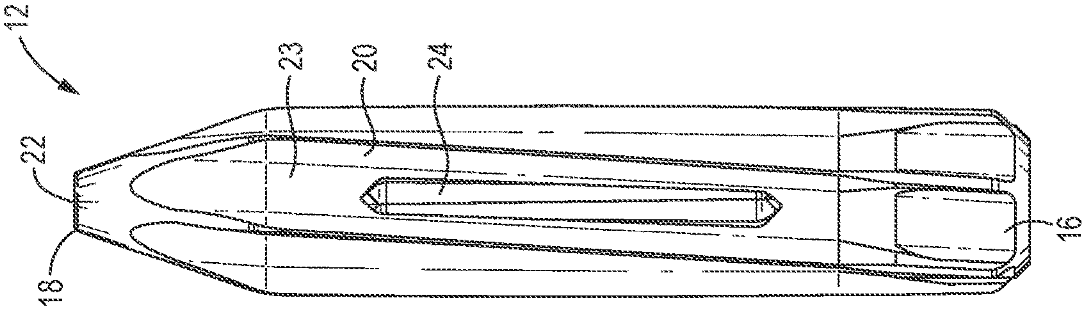
FIG. 14 is a perspective view of the anchor of FIG. 13, rotated to show the window or aperture more clearly, although at this scale, or even at this larger scale, the lattice work cannot be effectively shown and one must rely on the example of FIG. 10B.
Figure 13:
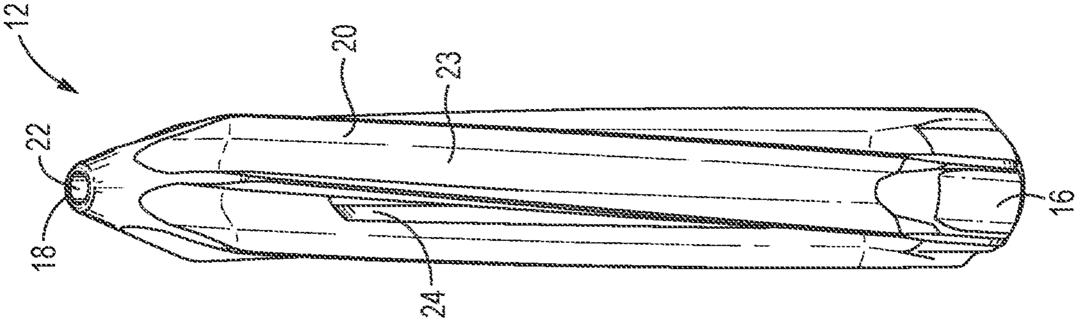
FIG. 13 is a yet longer version thereof illustrating an aperture that may be entirely open or may typically and more mechanically stably provided with a lattice work or array of apertures through the core.
Figure 12:
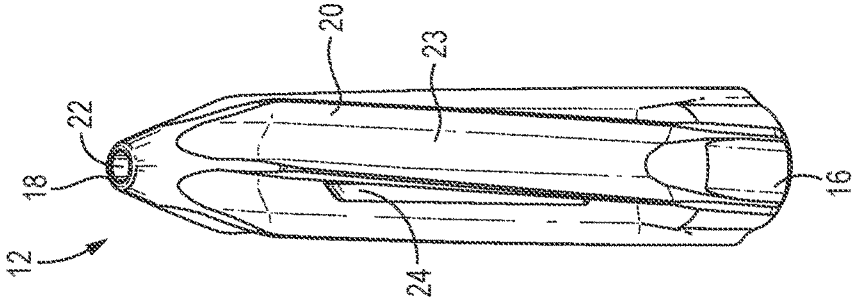
FIG. 12 is a perspective view of a longer version thereof, where longer means more diameters or effective diameters in length.
Figure 11:
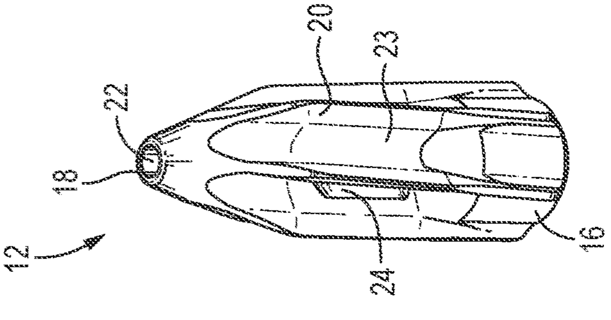
FIG. 11 is a perspective view of one embodiment of an anchor in accordance with the invention, illustrating apertures for grow-through space whether or not apertures of the same order of magnitude as the effective diameter of the anchor, a lattice work or general porosity is used.

In FIGS. 11 through 15, one will note that the aspect ratio of all diameters with respect to lengths is considerably larger in FIG. 11, is less in FIG. 12, and is less still in FIGS. 13 through 15. It is typically required to consider the anatomical distances or dimensions into, through, between, and the like with respect to bones 14 that are to be fused or fixed. Fusion typically occurs after a surgery, when the bones have been fixed by an anchor 12 in order that bone growth may occur around the anchor 12 in order to permanently fuse the two bones 14 together. Specifically, in the illustrated embodiments hereafter, where the bones 14 are a sacrum 14*a* and ilium 14*b*, dimensions and aspect ratios may have significance to the successful selection and implantation of an anchor 12.

One will also note that certain embodiments illustrate apertures 24 or grow-through areas 24. For the sake of clarity, the lattice work 24 or porosity 24 is not illustrated in any of the FIGS. 11 through 15. This is not because they will not include those lattices 24 as illustrated in 10B, but because such cannot be illustrated in this scale of the instant presentation. Thus, the illustrations of FIGS. 13 through 15 represent the same physical object, including some walls 23 that have no grow-through apertures 24, and other walls 23 that do include such. Accordingly, FIGS. 13 through 15 illustrate a single embodiment rotated to provide illustrations of the growth apertures 24 at different angles of rotation of the anchors 12 about their central axes (center line extending longitudinally through the center of the lumen 22).

It has been found that support of the wall 23 or core 23 of an anchor 12 militates in favor of a lattice work 24 rather than comparatively larger (of the same order of magnitude as the distance circumferentially between splines), are less mechanically stable. Collapse, twisting closed, and the like may be problematic, depending on other dimensions. It has been found that grow-through areas 24 of the type illustrated in FIG. 10B provides sufficient structural integrity to support the loads required to maintain the dimensional stability of the entire wall 23, the splines 20, and so forth.

Figure 16:
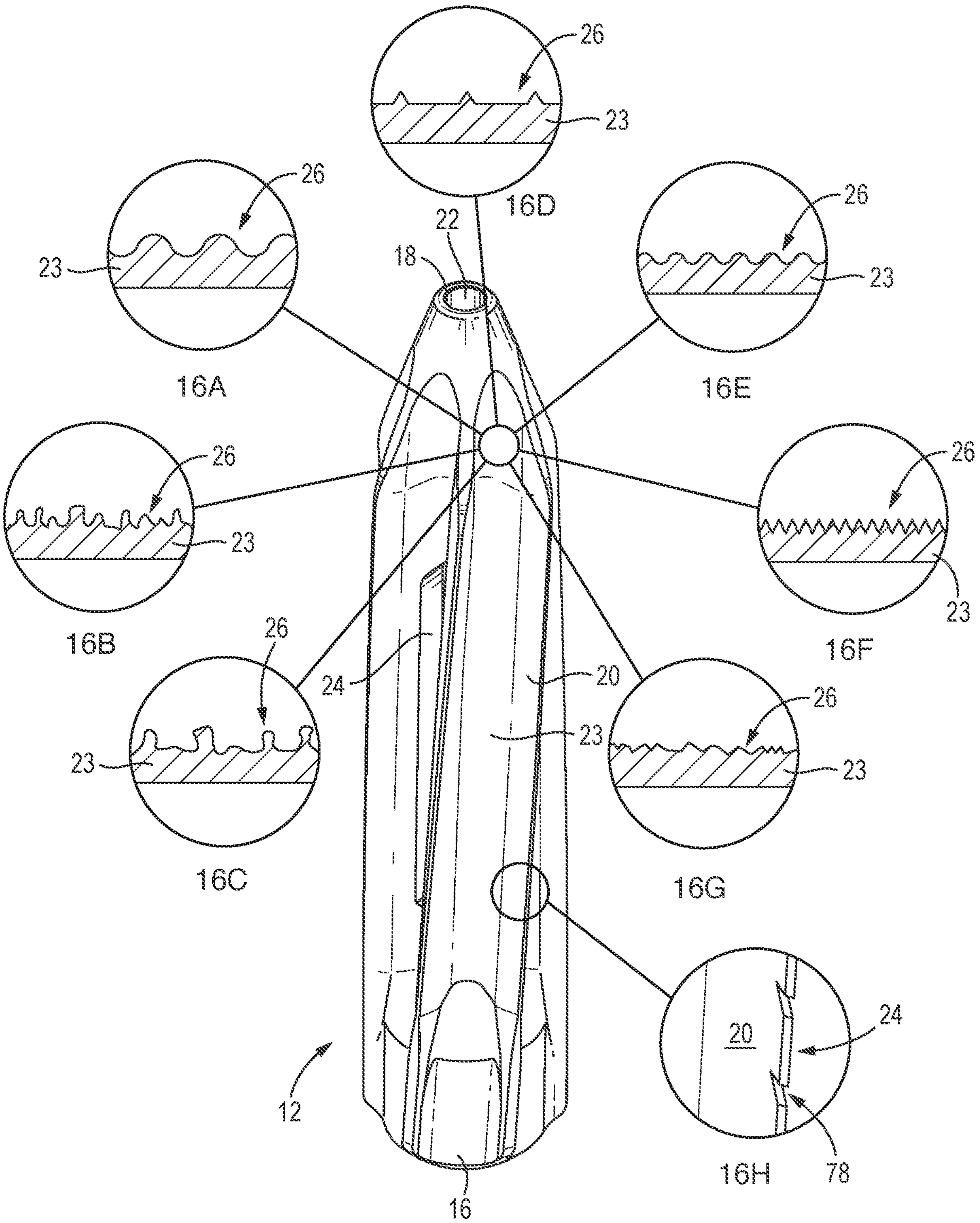
FIGS. 16, including internal

Referring to FIG. 16 and included FIGS. 16A-16H or images 16A-16H, while continuing to refer generally to all figures, one embodiment of a growth engagement mechanism 26 or surface treatment surface 26, also referred as texturing 26 is to provide various surface roughness 26 to which bone growth may adhere. Simply growing cortical bone into concavities represented by a particular texturing 26 is effective to resist any shearing of bone growth along the surface directions (in two dimensions, of the walls 23).

For example, FIG. 16 includes several insets 16A through 16H. For example, the image 16A suggests a somewhat scalloped appearance. This provides both convex and concave surfaces. It may be created on any surface, whether the surface of the wall 23 or the surface of the individual splines 20. It may typically be provided by etching, additive manufacture (3-D printing), or the like. It may typically be regular, and thereby be provided in mass production.

The image 16B shows a surface roughness that is quite irregular. In this embodiment, the edges tend to still be rounded, but the heights, the widths, and so forth (all dimensions) of the surface roughness 26 or texturing 26 are random. This is typically provided by a manufacturing technique known as sputtering. That is, random globules of molten metal may be attached to a base metal by a throwing by "sputtering" in which the material for texturing 26 is thrown as a liquid toward a heated surface and will secure, after splashing, and cooling. Likewise, such surface texturing may also be provided by sintering. Sintering is a process whereby a granular material may be packed into a mold, as distinct particles. The particles may then be heated until they partially melt, sufficiently to adhere to one another, but yet leaving porosity therebetween.

The image 16C is an alternative embodiment in which larger spaces or gaps may be left along the surface of a wall 23 by one of the foregoing methods, such as centering or sputtering. Typically, these processes result in a somewhat random distribution of texturing 26 of random dimensions.

Referring to FIG. 16, and its included FIGS. 16A-16H or images 16A-16H, and image 16D in particular, this inset illustrates a surface texturing somewhat sharply pointed, suitable for creation by machining, molding, casting, forging, or the like. One benefit of such a mechanism is uniformity. Nevertheless, other manufacturing methods may provide randomness which has its own benefits, such as a random growth and therefore somewhat self-securing bone growth around the various, randomly sized, and randomly distributed texturing 26.

The image for 16E illustrates a smaller dimensionality, similar to the texturing 26 of the image 16A. Similarly, FIG. 16F illustrates a more dense texturing 26 of a similar type to FIG. 16D. FIG. 16G, another somewhat reduced in height but random texturing. This relates very much to the same processes that may be employed for FIGS. 16B and 16C. However, images 16B and 16C indicate undercuts wherein bone growth on a surface 23 or wall 23 may actually have undercuts that are filled in with bone growth causing adherence to the wall 23 and further eliminating or reducing the probability that the bone growth can later be drawn away from the anchor 12.

One may note that the anchor 12 in general, does not necessary need an undercut texturing 26. This is because being surrounded by bone, typically cortical bone, the anchor 12 becomes encased and completely circumnavigated or circumscribed by the bone growth. Thus, any texturing 26 whatsoever becomes sufficient to prevent dislodgement or movement of the anchor 12 with respect to the subsequently grown bone growth.

Referring to image 16H or FIG. 16H in FIG. 16, a barb 78 may be formed as a means of texturing 26 on a spline 20. For example, barbs 78 as a form of texturing 26 on an edge of a spline 20 may provide immediate "purchase" or engagement with the native bone into which an anchor 12 has been installed or penetrated.

For example, the splines 20 will typically have an "interference fit" as that term is used in the engineering, manufacturing, assembly, fabrication, and other technical arts. An interference fit means that the dimension of an outer or receiving cavity, surface, slot, path, or the like is less than the outermost dimensions of the item (e.g., a spline 20 or core 23 of an anchor 12), thus not an actual fit with a tolerance for clearance. Instead, one or both of the materials must provide a certain amount of "give."

By the word give, is meant that either elastically, plastically, or by abrasion, one of the surfaces must displace in order to make the fit. Again, abrasion means wear, while elastically means still capable of full recovery of dimensions when any distorting force is removed. Plastically means that the material has "yielded." Yielding means that the molecular structure or atomic structure of a material has permanently shifted, never to return to its former position. The term 'yielding' is a term of art that should be understood by any technician in mechanical or manufacturing arts.

Barbs 78 tend to move along a path during insertion or installation of an anchor 12 but will not return out of that path with the same amount of force applied. This is because the barbs 78 are slanted to glide forward in response to force axially applied to an anchor 12, but will immediately dig in to the surrounding material upon application of a force in an opposite direction. Thus, such anchors 12 with splines 20 having barbs 78 become immediately fixative and will not remove or move opposite to their direction of insertion with the same amount of applied force required to insert them. Barbs 78 may be used in other embodiments of surface texturing, but creating undercuts such as barbs 78 is difficult and therefore may limit the utility or availability of barbs 78 generally.

One will note various mechanisms combine to stabilize anchors 12. Texturing 26 may be applied to any particular surface. Those surfaces may be corrugated, shaped, convex, concave, undercut, through holes, blind holes, heavily (deeply) textured, roughened surfaces, regions perforated with grow-through areas 60 (GTA 60), splining, helical splining with very long pitch, and so forth.

Figure 17:
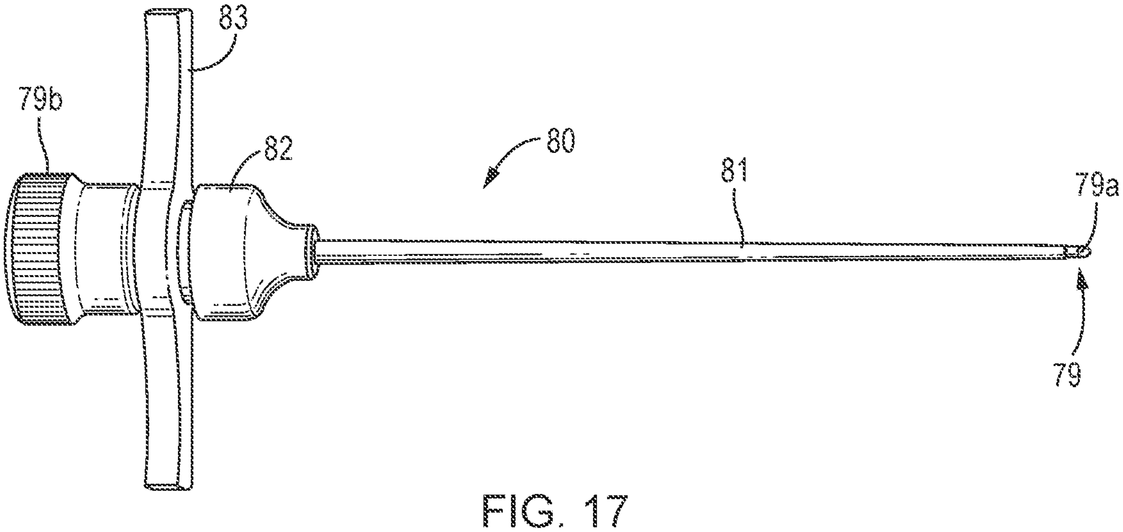
FIG. 17 is a perspective view of a Jamshidi needle for use in a non-conventional manner in a process in accordance with the invention.

Referring to FIG. 17, a trocar 79 includes a point 79*a* fixed to a handle 79*b* acting as an extractor 79*b*. This trocar 79 is placed inside a Jamshidi needle 80. The actual penetrator 81 or needle 81 is typically used to connect to a syringe in place of the handle 79*b* or interfacing therewith in order to draw a biopsy from tissue, bone marrow, or the like. Thus, a Jamshidi needle 80 is typically implemented by using the handle 83 to which a mount 82 secures the needle 81 or the needle portion 81 of a Jamshidi needle 80.

In accordance with the invention, a trocar 79 extends beyond the needle portion 81 to be the vanguard or phalanx of the Jamshidi needle 80. Thus, in this configuration, the Jamshidi needle 80 does not draw a biopsy, but simply forms an initial penetration for entry of the K-wire 84 of FIG. 18A. Upon withdrawal of the trocar 79 by means of drawing back the handle 79*b*, the main penetrator 81 is left hollow and open to receive a length of K-wire 84. The point 86 moves down through the penetrator 81, anchoring into bone by applying force or impact on the base end 88. The K-wire 84 is used in the role of a guide for subsequent instrumentation. Once the K-wire 84 has been anchored at its point 86 into bone, the Jamshidi needle 80 may be withdrawn.

Figure 18A:
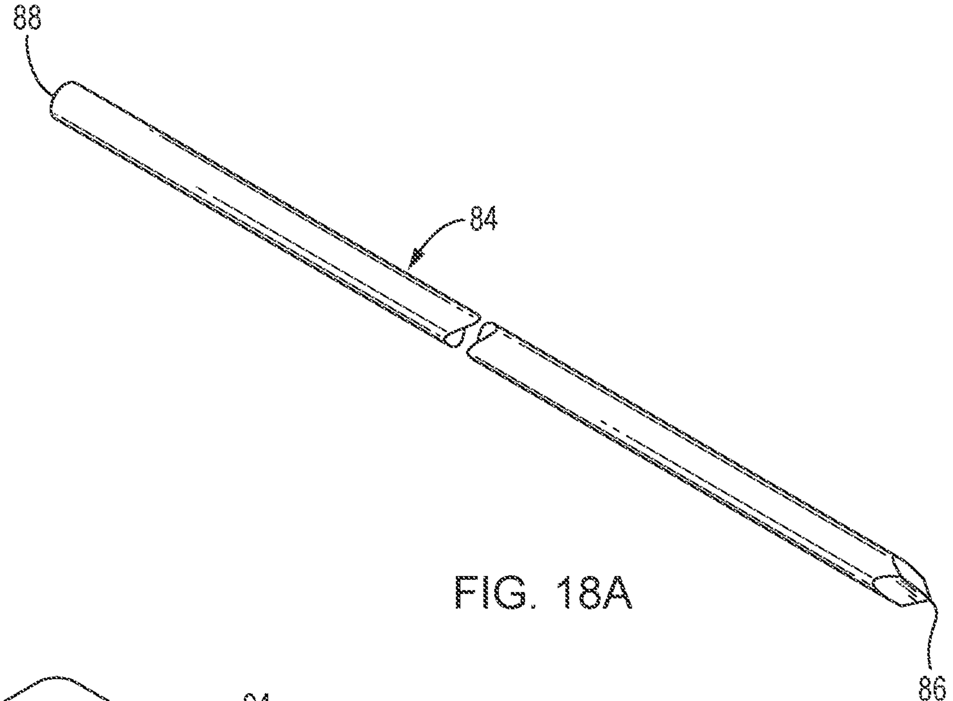
FIG. 18A is a perspective of one embodiment of a K-wire to be used as a guide in certain embodiments of a procedure in accordance with the invention.
Figure 18B:
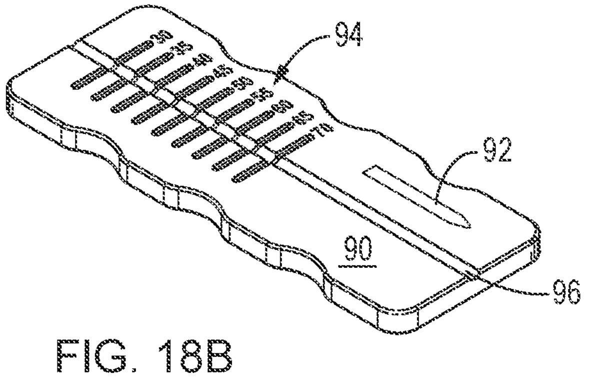
FIG. 18B is a perspective view of one embodiment of a distance gauge for use in combination with the K-wire of FIG. 18A.

Referring to FIGS. 18A and 18B, the K-wire 84 will be selected to have a certain, known length. The diameter of the K-wire 84 will fit not only inside the penetrator 81 of the Jamshidi needle 80, but also in the lumen 22 of an anchor 12. The gauge 90 is oriented according to the indicator 92 identifying the direction of the K-wire 84. Thus, the graduations 94 on the gauge 90 allow a user, such as a surgeon, to measure the length of a K-wire 84 remaining exterior to a surgical site.

By laying the groove 96 or bed 96 of the gauge 90 against the K-wire 84, one effectively lays the K-wire 84 into the bed 96 leaving the blunt end 88 or base end 88 of the K-wire 84 lying at some point along the gauge 94. By reading the measurement of the gauge 90, one may then determine how much of the K-wire length is still outside the surgical subject, and how much has been inserted within. This provides an indication of the exact location along the path of the K-wire 84 and originally the Jamshidi needle 80 from the surface of the subject or skin of the subject. At this point, the gauge 90 may be set aside and the K-wire 84 may be relied upon as a guide 84 in subsequent procedural steps.

Figure 19A:
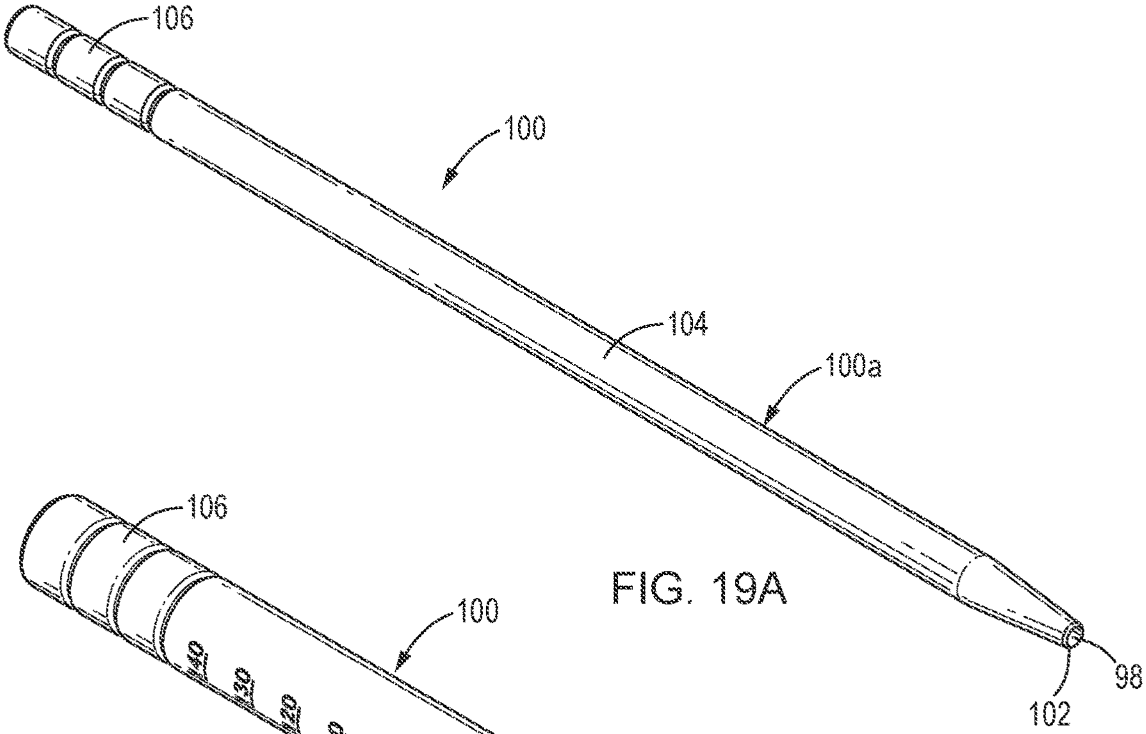
Figure 19B:
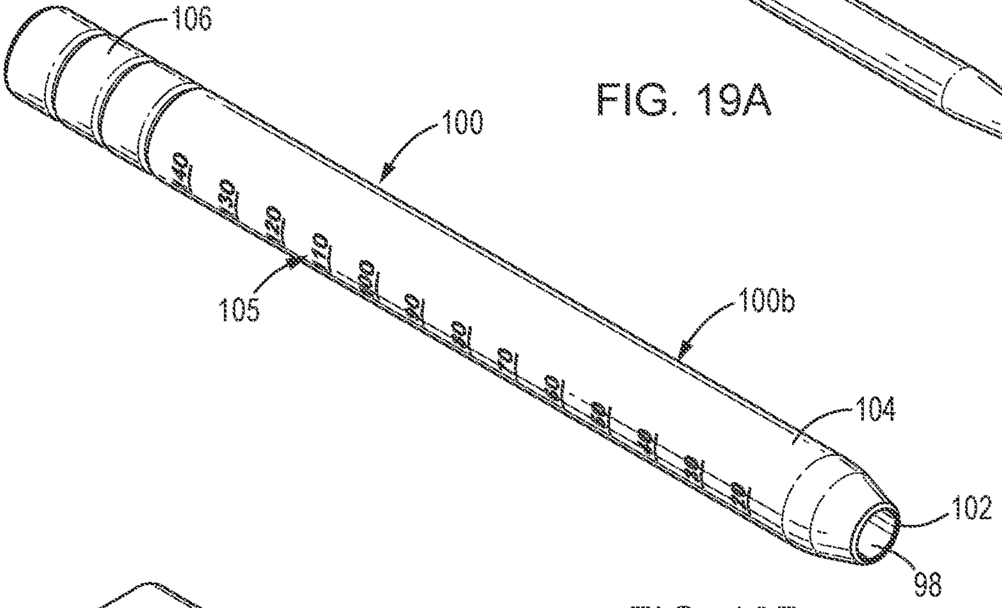
FIG. 19B is a larger dilator, configured to fit over the dilator of FIG. 19A in order to further enlarge an access opening through tissues in order to access bones to be anchored together.
Figure 19C:
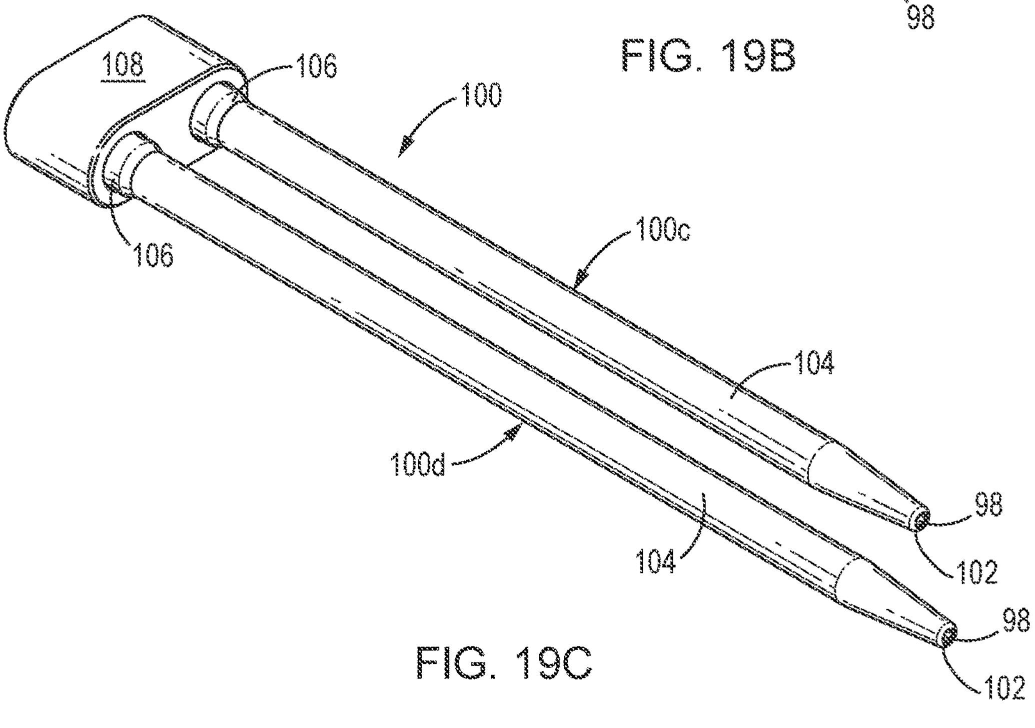
FIG. 19C is a twin or parallel pair of dilators, fixed together such that the longer dilator may replace literally a small dilator such as that of FIG. 19A in order to maintain parallel another dilator in close proximity and in perfect parallel relation thereto in certain embodiments of procedures in accordance with the invention.

Referring to FIGS. 19A through 19C, various dilators 100 are illustrated. In FIG. 19A, the dilator 100 includes a lumen 98 or channel 98 fitted to slide along the K-wire 84. A leading edge 102 or point 102 fits closely around the K-wire 84, thus urging the soft tissue outward toward the main or outer diameter of the dilator 100*a*. The dilator 100*a* is considered a small (relatively speaking with respect to the larger or large) dilator 100*b* of FIG. 19B. As the barrel 104 of the small dilator 100 is urged axially along its length toward the point 102, or following the point 102, the dilator 100*a* will cause stretching and a certain amount of trauma to the surrounding soft tissue.

However, as tissue stretches around the circumference and outer diameter of the small dilator 100*a*, although there may be trauma, incisions will not be required to cut through the tissue, unnecessarily severing neighboring tissue. Eventually, any tooling, mallet, or other device used on the shank 106 to drive the small dilator 100 forward will be removed and a large dilator 100*b* will be slipped over the shank 106 of the small dilator 100*a*. At this point, by force, pressure, or impact, the shank 106 of the large dilator 100*b* will be urged along the path now defined by the outer diameter of the small dilator 100*a*. Again, gauge marks 105 on the barrel 104 of the large dilator 100*b* provide a direct reading of the depth of penetration by the large dilator 100*b*. More is explained hereinbelow regarding the use and structure of the large dilator 100*b*.

Referring to FIG. 19C, in certain embodiments, it may be desired to place two anchors 12 exactly parallel to one another. This may be done with two anchors 12 placed parallel within a joint 15 or across a joint 15. Typically, it is preferable to place parallel anchors 12 within a joint 15, ostensibly parallel to the cortical surfaces of the bones 14 making up the joint 15 or joined by the joint 15. In such a circumstance, the foregoing procedure regarding an installation of a small dilator 100*a* may be done, but the small dilator 100*a* may then be immediately removed, while a small dilator 100*c* is passed down along the K-wire 84 and the path previously formed by the small dilator 100*a*.

Thus, another small dilator 100*d* fixed through a mount 108 securing the shanks 106 of both the small dilator 100*c* and the small dilator 100*d* will require that the small dilator 100*c* penetrate parallel to the small dilator 100*c*, which is following the path already dilated by the small dilator 100*a* that was subsequently removed. It may be that a second K-wire 84 may be passed down through the second dilator 100*d*, but this need not be necessary. In some respects, a K-wire 84 may be used as a trocar 79 inside the lumen 98 of the small dilator 100*d* in order to assist the small dilator 100*d* in penetrating tissues that were not addressed by the Jamshidi needle 80.

It is a principal function of the twin dilator 100 of FIG. 19C to provide a second, and parallel, path. Those parallel paths may both be provided with K-wire 84 as guides 84. Eventually, the small dilators 100*c*, 100*d* may be withdrawn and replaced with small dilators 100*a* down both paths, down two K-wires 84, one in each path, and thereafter the use of a large dilator 100*b* over each may be accomplished. Nevertheless, use of dilators 100 becomes a function of the size of the path required in order to pass an anchor 12 into a securement site between two bones 14.

Figure 20:
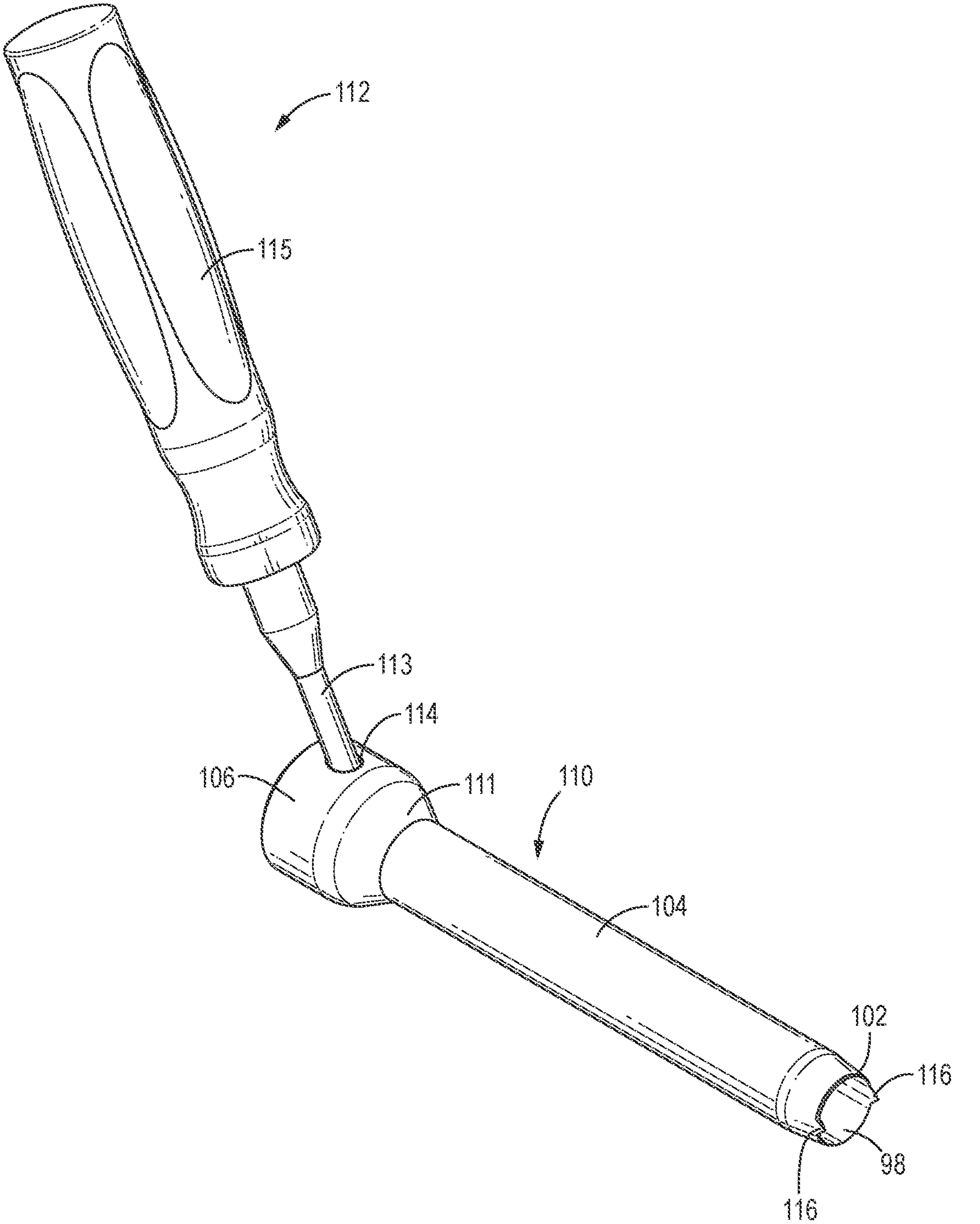
FIG. 20 is a perspective view of one embodiment of an access portal, which acts somewhat as the larger dilator of FIG. 19B, but has a substantially thinner wall, and has not the principal purpose of dilating, but rather forming a portal by guiding down the larger dilator and anchoring against rotation in one of the bones to be affixed to another bone, and also showing a tool for use in applying longitudinal forces, as well as rotational forces in order to properly install the access portal before withdrawing the dilators therewithin.

Referring to FIG. 20, a working portal 110 is typically a barrel 104 like those of FIGS. 19A through 19C, but substantially thinner in its wall thickness. The function of the working portal 110 is not to further dilate a path for insertion of an anchor 12 but rather provide a stable passageway 98 or channel 98 through which to pass surgical instruments. To that end, the leading edge 102 of the working portal barrel 104 is suitable for sliding along the outer diameter of the barrel 104 of the large dilator 100*b* of FIG. 19B. Accordingly, a head 111 or mount 111 serves to strengthen and support and connect the barrel 104 of the working portal 110. Thus, the lug 106 or shank 106 of the working portal 110 is provided with one or more apertures 114 suitable for receiving a shaft 113 applying force from a handle 115 or grip 115.

Thus, as the working portal 110 is moved axially along the length of the large dilator 100*b*, the handle 115 or grip 115 applies axial and circumferential force to the shank 106 or lug 106 of the working portal 110. Points 116 are typically engineered to penetrate into cortical bone in order to secure or fix the working portal 110 to the bone that is the subject of the installation or insertion of an implant 12, also called an anchor 12.

Upon contacting bone 14 of some type, according to the specific surgery, a working portal 110 may advance under a mallet providing an impact load on the shank 106 of the working portal 110 to fix the points 110 and into local bone 14 thereby stabilizing the working portal 110 in all dimensions of consequence. Axially, it abuts the bone 14. Radially, it is held by tissue, as well as by the points 116 against lateral motion in any radial direction. Similarly, the points 116 secure the barrel 114 of the working portal 110 against rotation with respect to the bone 14.

At this point in a procedure in accordance with the invention, the user, medical professional, is prepared to pass various tools 120, 130, 134, 140, and so forth into the working portal 110, and along the guide 84 that is the K-wire 84 still embedded in bone 14 at the center of the working portal 110.

Figures 21, 22:
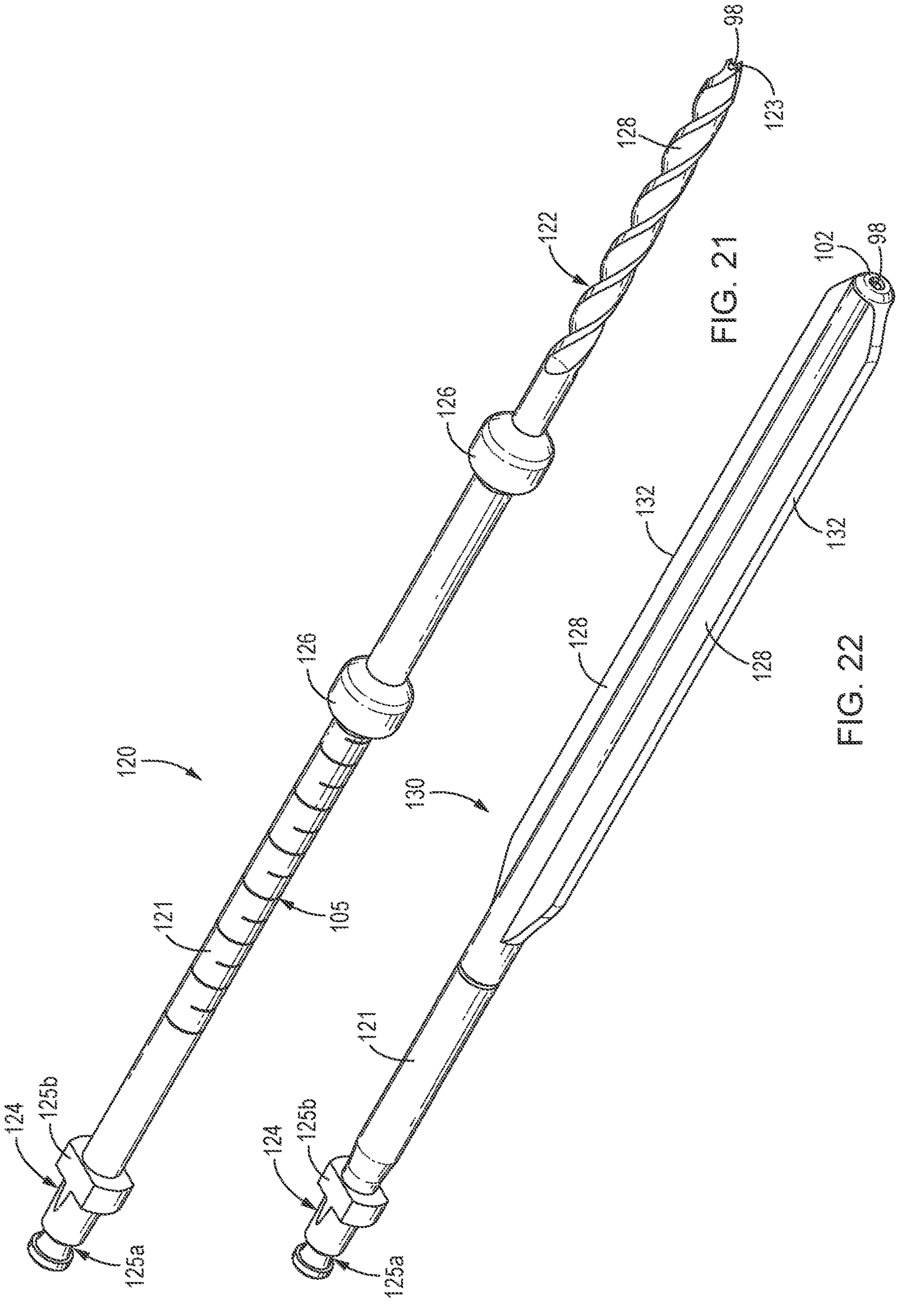
FIG. 21 is one embodiment of a drill for drilling a pilot hole in bone, thus reducing the trauma of penetration of the bone, this particular tool also having gauge markings for determining depth of penetration, as well as riders that maintain the drill bit centered within the access portal during operation.
FIG. 22 is one embodiment of a suitable reamer, this being a paddle-type of reamer typically used in a "parallel incursion into a sacroiliac joint, effectively parallel to both the cortical surfaces, and capable of cleaning out cartilage and any other soft tissue that will impede the proper functioning of an anchor.

Referring to FIGS. 21 and 22, a drill 120 is mounted to a shaft 121. The shaft 121 may be provided with gauging marks 105 thus providing immediate feedback as to the depth at which the drill bit 122 has penetrated. Again, the drill 120 includes a point 123 having a lumen 98 or channel 98 guiding along the K-wire 84. In the illustrated embodiment, a shank 124 may connect to a hand operated brace such as is used in a brace-and-bit combination. Alternatively, the shank 124 of the drill 120 may connect to a motorized unit for rotating the bit 122.

In the illustrated embodiment, the shank 124 is provided with a securement 125, here embodied as a groove such as may be used for a quick-connect mechanism for securing the drill 120 in an axial direction to a driver mechanism, well known and not shown. Meanwhile, a flat 125*b* may provide for engagement by a driver thereby assuring rotary motion by the driver. Thus, the engagement mechanism 125*a* or securement 125*a* acts to secure the drill 120 axially, while the flat 125*b* acts to provide rotary motion driven by a drive mechanism. The drive mechanism is not shown because such are available in the art as hand cranks, electrical motors, and the like.

Of note, are riders 126 on the shaft 121 of the drill 120. These riders 126 act as carriers 126 to center the drill bit 122 within the working portal 110. Meanwhile, the lumen 98 passing axially through the center of the bit 122 and shaft 121 also guides down a K-wire 84 in place for that purpose. The flutes 128 on the bit 122 are designed to cut and carry back any materials drilled out by the bit 122.

Likewise, the drill 120 may be withdrawn from a path, in order that saline or typical flush solution may be injected or introduced to irrigate the opening made by the drill bit 122 and wash away any resulting debris. One will note that the drill bit 122 is sufficiently long that it may drill through both bones in any crossing implementation and may drill along a cartilaginous joint in a parallel implementation. Thus, the flutes 128 may cut into soft tissue, marrow, cartilage, as well as cortical bone as required to establish the path that will eventually be followed by insertion of an anchor 12.

Referring to FIG. 22, in certain situations, a reamer 130 may be used. Inasmuch as cortical bone is comparatively brittle, meaning that it will typically fracture, chip, cut, abrade, or otherwise remove in response to a hard instrument like the flutes 128 of a drill bit 122, softer tissues may not. Accordingly, it may be required to remove a drill 120 and insert the guiding K-wire 84 into the lumen 98 of a reamer 130. Again, the reamer 130 has flutes 128 that include cutting edges 132. The shaft 121 operates as other shafts 121, passing down into the working portal 110, and rotating about the K-wire 84 down the center lumen 98 of the tool 130. The shank 124 may operate similarly to that of the drill 120 in FIG. 21.

The reamer 130 in the illustrated embodiment is sometimes referred to as a paddle reamer 130. It may have two, three, or more flutes 128 extending from it. Its function is to rotate to thereby clean out cartilaginous material soft tissue that may otherwise impede insertion of an anchor 12. Also, the reamer 130 may also tend to scrape against cortical bone in a parallel insertion configuration in order to provide "bleeding bone" for enabling bone growth around an inserted anchor 12 thus permanently fixing the anchor 12 and creating a solid, fixed relationship between the two bones 14*a*, 14*b* being anchored together.

Figure 23:
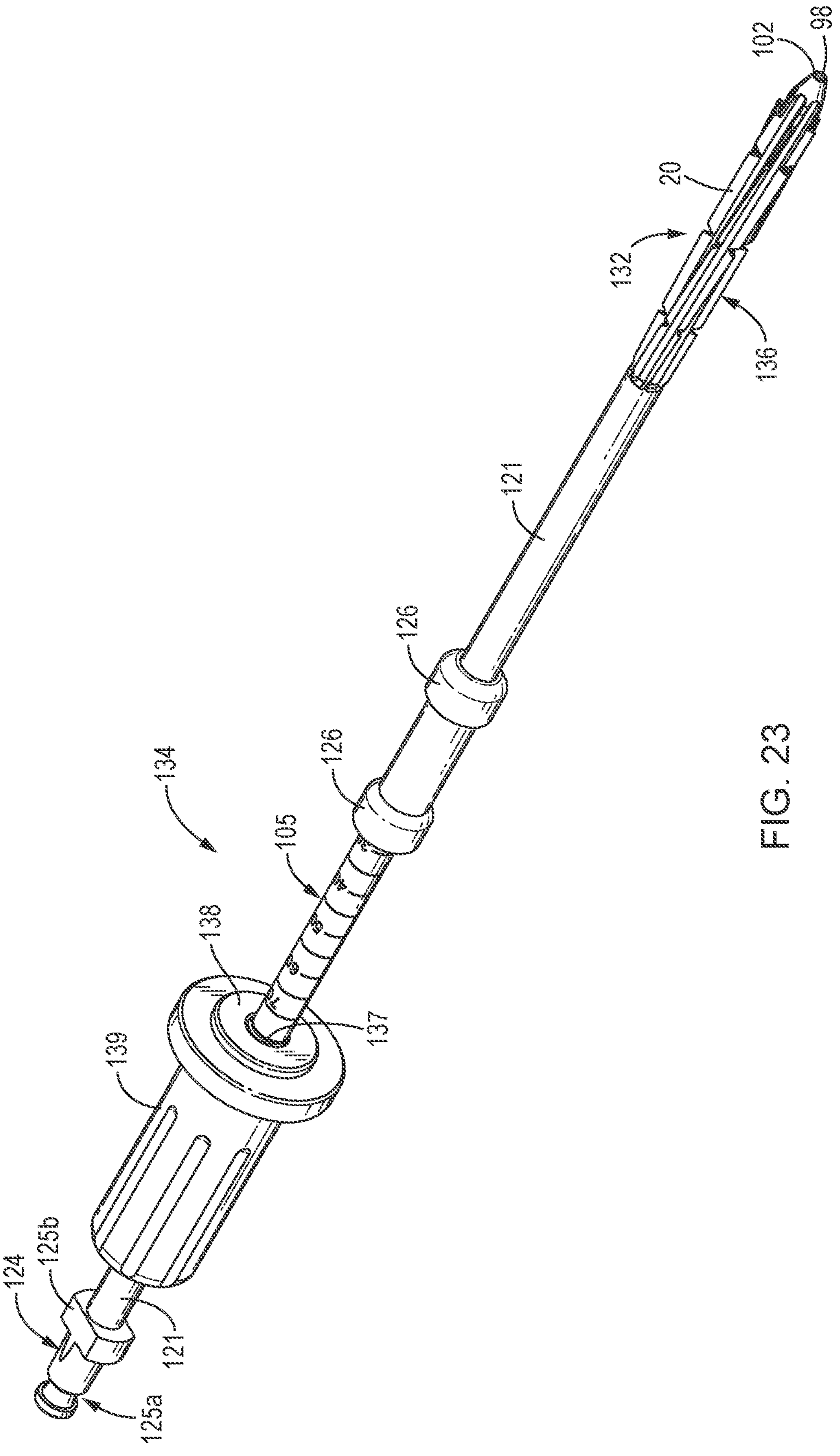
FIG. 23 is a perspective view of one embodiment of a broach, showing not only the operable, cutting edges of the broach (which are sub-sized to be less than the dimensions of the anchor itself) along with riders for centering the broach in the access portal, as well as gauge markings, and a gauge mechanism, which may be set according to the gauge markings, or which may include a "rifling" race for receiving a rifling-type armature or central mandrel to assure the proper ratio of advance to rotation of the broach as it prepares a path for an anchor in accordance with the invention.

Referring to FIG. 23, a broach 134 may not always be required, but may relieve somewhat a desired interference fit between an anchor 12 and the bones 14*a*, 14*b* into which it is placed. In the illustrated embodiment, the broach 134 may include a shaft 121 and riders 126 for maintaining the shaft 121 centered within the working portal 110. Likewise, a head end 136 or head 136 opposite the shank 124 will serve as a cutting tool to cut paths for the splines 20. That is, the head 136 of the broach 134 included splines 20 that will effectively cut spaces for the splines 20 of the anchor 12. In the illustrated embodiment, cutting surfaces 132 are provided. However, these are not rotary cutting surfaces, but rather cut in order to provide entry for the broach head 138 to expand the space available in the hole or aperture drilled by the bit 122.

One will note that the angle or the circumferential progression of the splines 20 on the head 136 exactly match those of an anchor 12. Accordingly, the splines 20 of the head 136 may initially penetrate the diameter of the hole left by the bit 122 passing into or through bone 14. The broach may be instantiated in multiple versions, each broaching slightly more material out of the cortical bone 14. Alternatively, the various diameters of the head 136 may increase such that the cutting edges 132 and the head 138 may cut initially at one diameter, then subsequently at larger diameters until approaching, but typically not meeting the outer diameter of an anchor 12.

Meanwhile, the thickness of each spline 20 in the head 136 is best served by being slightly less than a thickness of a spline 20 in an anchor 12. In this way, an anchor 12 is inserted against the frictional clamping force of the interference fit in which the pathway formed by the broach head 136 is slightly undersized to fit the radial dimensions and circumferential dimensions of the anchor 12 and its splines 20.

Threads 137, along the shaft 121 may provide for adjustment by a grip 139 that acts as a contact surface 138 preventing further axial movement of the shaft 121 and broach 134 into the access portal 110 or working portal 110. Of course the riders 126 maintain centering, as does the K-wire 84 in the lumen 98 of the broach 134. Gauge marks 105 provide an immediate feedback as to the positioning of the contact surface 138 that will eventually contact the shank 106 of the working portal 110, limiting the penetration of the broach 134 and head 136 into the surgical path.

In certain embodiments, the handle 139 may be engaged with an internal spiraling path that instead rotates and advances the shaft 121 at exactly the rate required by the splines 20 of the broach head 136. The broach 134 may typically be operated by a hand tool secured to the shank 124. Thus, a user can work the broach 134, much as a rasp in order to provide forward axial force on the head 136, as well as urging a rotational force along the direction of the splines 20 in order to cut through the bone 14 in a path suitable for receiving the anchor 12 later. Following broaching, the broach 134 is removed, and the path or cavity may be flushed to remove any debris, in preparation for insertion of an anchor 12.

Figure 24:
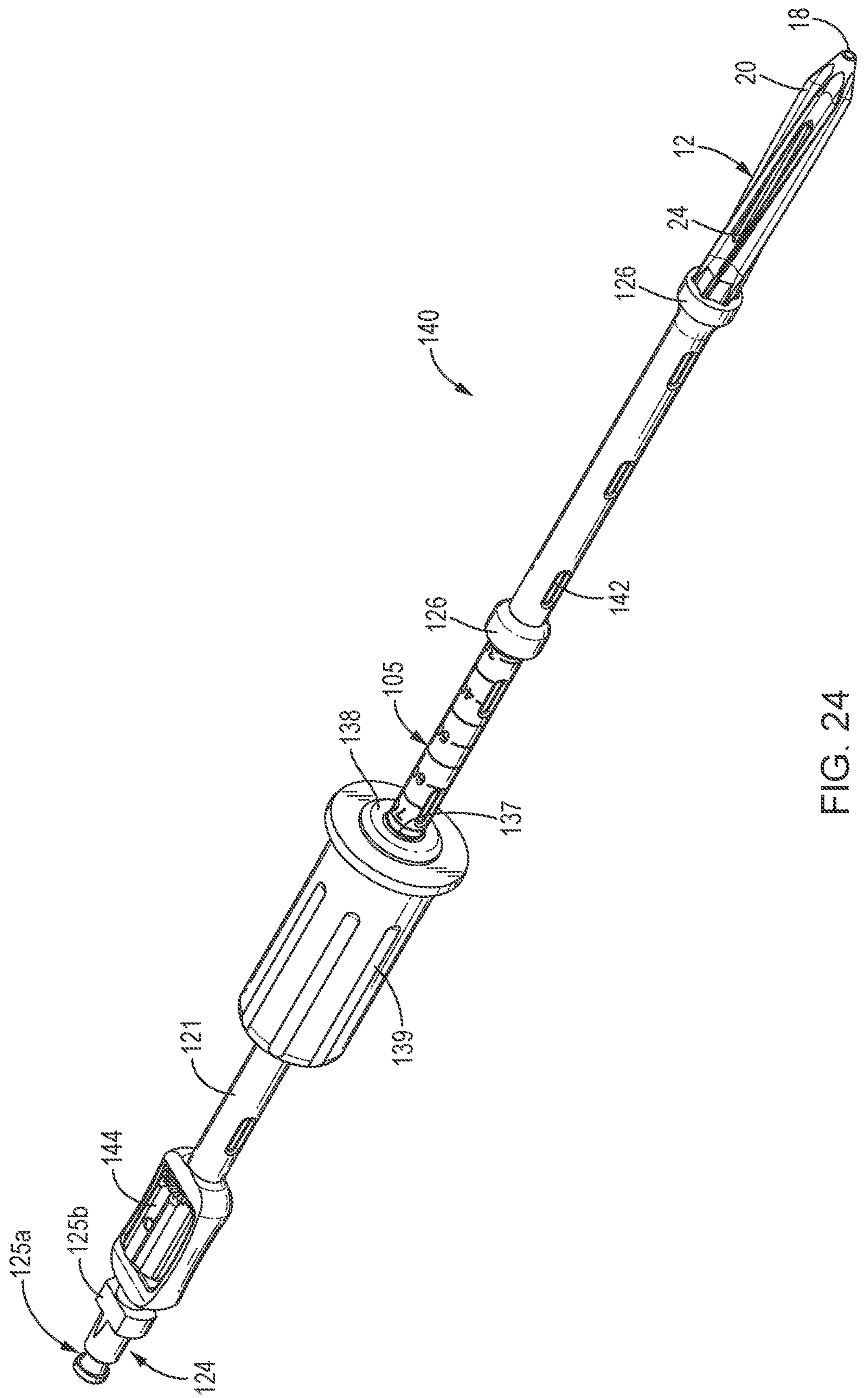
FIG. 24 is a perspective view of an insertion tool loaded with an anchor, also illustrating riders to center the anchor within the access portal, and also illustrating gauge markings and a gauge set that may be threaded along the tool to stop further penetration of the anchor at a preselected depth measurement.

Referring to FIG. 24, the insertion device 140 operates much like the broach 134. Rather than a broach 136, the actual anchor 12 is implemented. Again, the anchor 12 fits over a K-wire 84, while riders 126 may rotate and slide within the working portal 110. Similarly, the handle 139 or grip 139 may be threaded along the shaft 121 in order to gauge by the contact surface 138 the distance of penetration by the shaft 121 into the working portal 110. A tool 140 or inserter 140 may provide relief apertures 142 along the shaft 121, in order to allow free movement of a shank 124 connected directly to an anchor 12 as an inner shaft, inside the outer shaft 121. In this way, direct movement, orientation, or the like may be felt in order to assure that the splines 20 find the suitable openings created by the splines 20 of the broach head 136. An actuator 144 may operate to rotate the shank 124, the outer shaft 121, as needed for relative movement.

Figure 25:
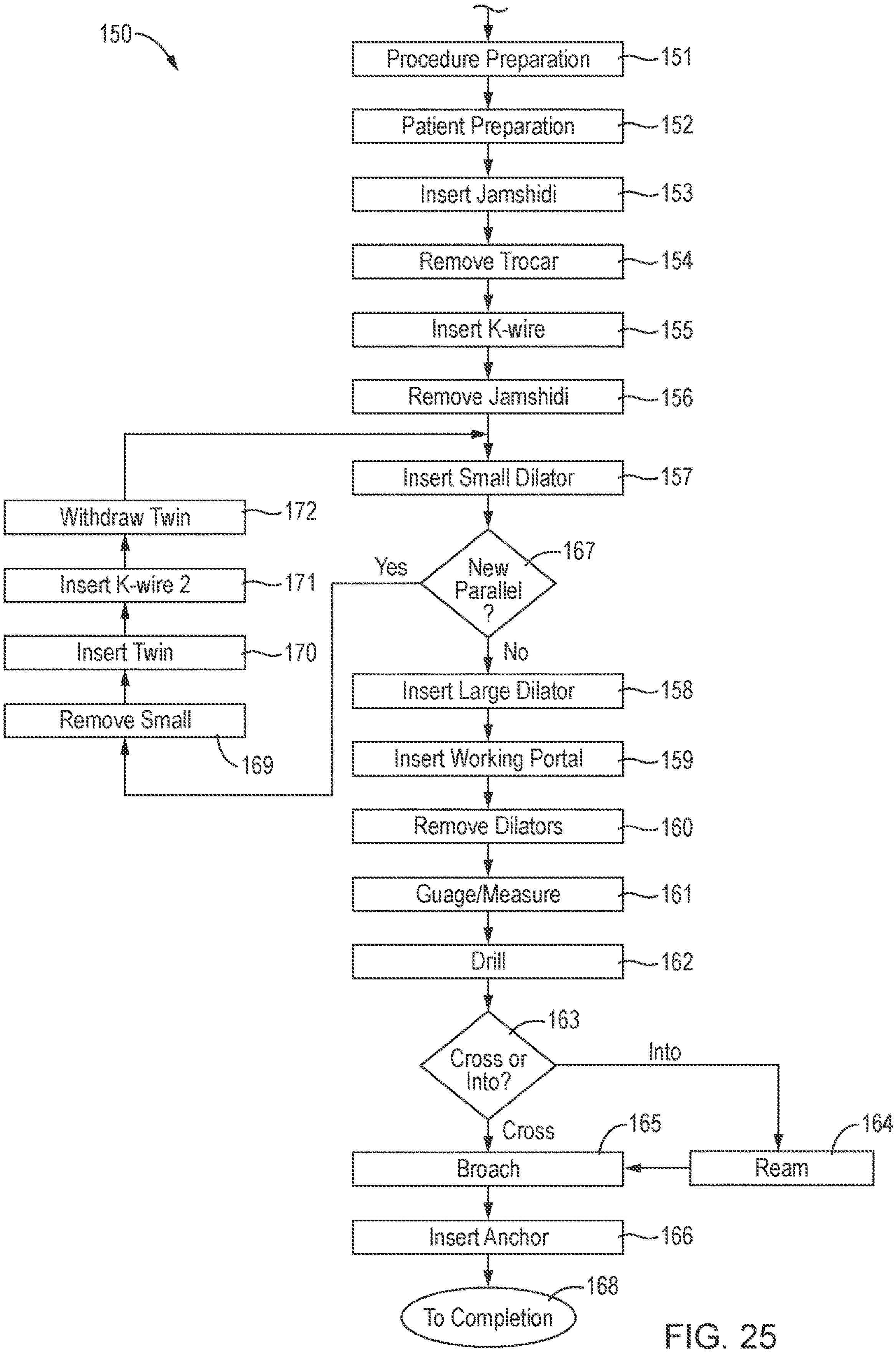
FIG. 25 is a process block diagram illustrating a procedure for implementing an anchor and the proper tooling for inserting fixation anchors to fix (rigidize) the sacroiliac joint.

Referring to FIG. 25, a process 150 is provided illustrating multiple embodiments of insertion techniques, depending upon the particular location and specific orientation of an anchor 12 in a joint 15. Initially, the procedural preparations 151 may need to be conducted, including providing all the proper tools properly laid out, sized, measured, setting measured to the extent that they can be, and so forth. Likewise, patient preparation 152 may require conventional protections for the patient and for the medical personnel as well as the site. This may involve x-rays, antiseptic sterilization of areas or spaces, draping with coverings, and so forth. Preparation 152 may actually include an initial incision through skin, fat layers, fascia, or the like in order to gain access to muscular tissue, as well as any other common patient preparation 152.

Insertion 153 of a Jamshidi needle 80 then occurs, followed by removal 154 of the trocar 79. This is followed by inserting 155 a K-wire 84 through the shaft 81 of the Jamshidi needle 80, ultimately securing the point 86 or other portion of the K-wire 84 into bone 14. The K-wire 84 may actually penetrate through and beyond the anchoring site. For example, the K-wire 84 may move past cortical bone, cancellous bone, more cortical bone, and on into soft tissue. The K-wire 84 may define a path that extends beyond the insertion of the point 18 or leading edge 18 of the actual anchor 12 inserted. One reason for this is that bone graft material may be added.

Once the K-wire 84 is properly inserted 155, removal 156 of the Jamshidi needle 80 can be done. Next, inserting 157 the small dilator 100*a* is done, followed by a decision 167 as to whether a new second, parallel, path is to be created, as described hereinbelow. If not, then insertion 158 of the large dilator 100*b* follows. The working portal 110 is next inserted 159, sliding over the outer diameter of the shaft 105 of the large dilator 100*b*. Once the working portal 110 is inserted 159 and anchored as discussed hereinabove, a user may remove 160 both the dilators 100*a*, 100*b* and gauge 161 for drilling 162. The gauge 90 with the K-wire 84 laid into the bed 96 may provide a gauging mechanism 94 for determining exactly how deeply into the path the drilling 162 needs to progress.

At this point, the next alternative in the procedure depends on the decision 163, whether the anchoring is across the bones 14*a*, 14*b*, or between the bones 14*a*, 14*b* (that is, along and inside the joint 15). If the anchoring is to be into the joint 15 (what we will call parallel to cortical surfaces, not parallel anchor paths, although the cortical surfaces are more tangential, not planar). Reaming 164 occurs, in the "inside joint" or "parallel to cortical surfaces" case. In either the cross or the parallel configuration, broaching 165 occurs, both as described hereinabove. Inserting 166 the anchor 12 using the insertion tool 140 results in the anchor 12 being fixed into place. Installation is thereby completed 158

In other words, if the decision 163 indicates a cross orientation across the joint 15 between, that is from one bone 14*a* to another bone 14*b*, then broaching 165 may proceed directly after drilling 152, and followed by anchoring 166 or inserting 166 an anchor 12. Note that the anchor 12 rotates as it moves forward into place, as a result of the helical path of the splines passing through the cortical bone as broached 165. The insertion tool may be urged rotationally in order to relieve the load on cortical bone carrying the splines 20 as they helically progress into, through, across, or along the bones 14*a*, 14*b*.

Going back now to the decision 167, if a new anchor, 12 parallel to the original K-wire 84 and small dilator 1001, is desired, then one may need to remove 169 the initial small dilator 100*a* and insert 170 the twin dilators 100*c*, 100*d*. Inserting 170 the twin dilators 100*c*, 100*d*, a second K-wire 84 may be inserted 171, followed by withdrawing 172 the dilator, and returning to the process 150 at the step of inserting 151 two small dilators 100*a* down those two parallel paths before proceeding.

Figure 26:
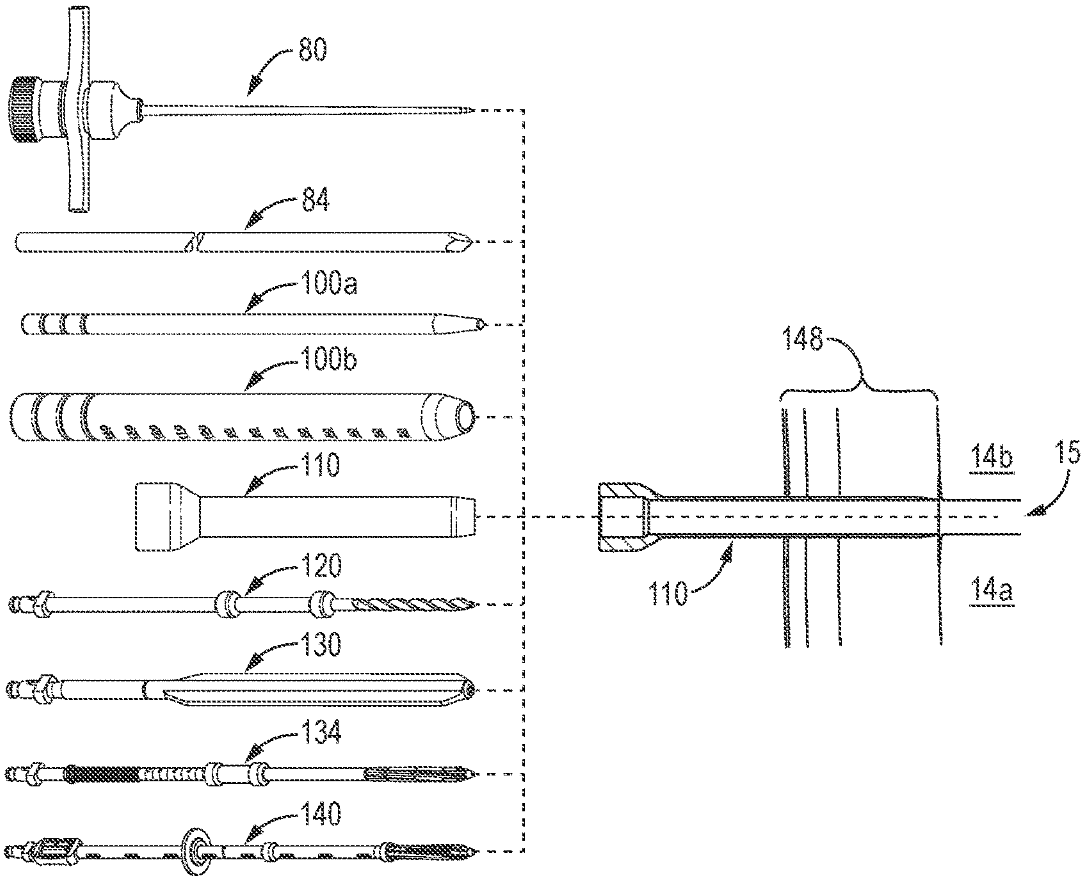
FIG. 26 is a diagram illustrating the sequence of application of the various tools in the process or procedure of FIG. 25, applied in this case to a "parallel" or "along-the-joint" insertion of an anchor.
Figure 27:
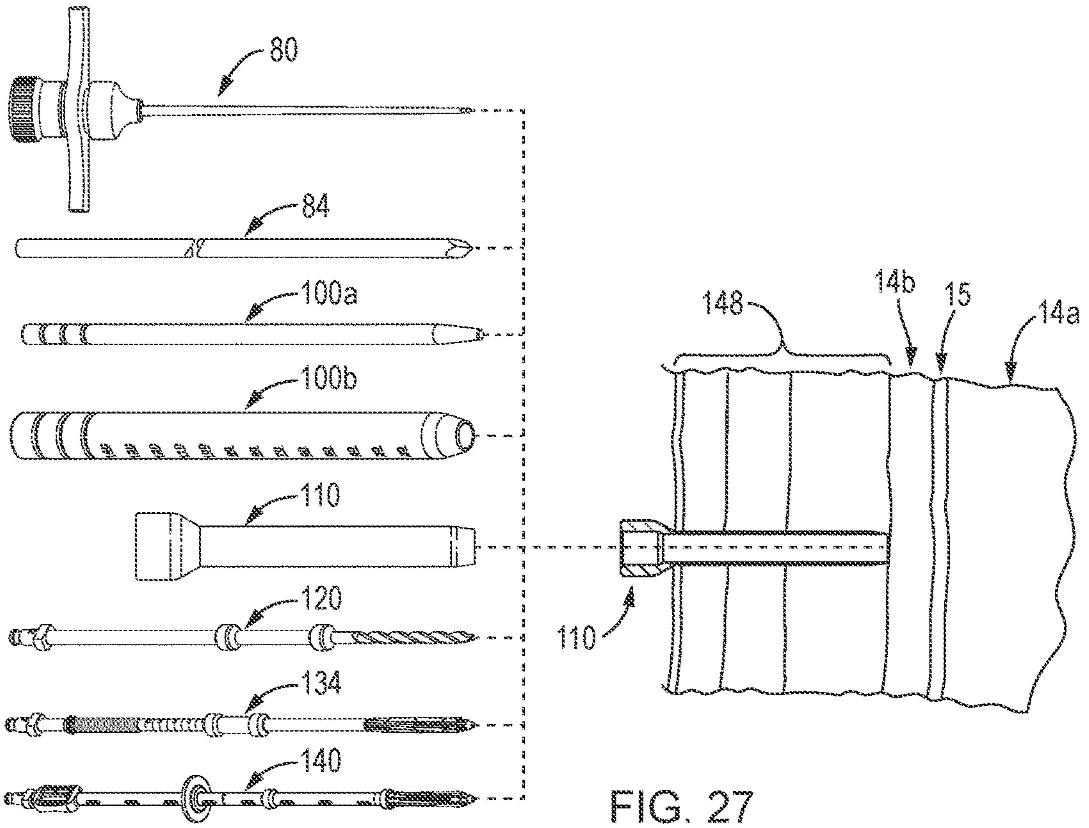
FIG. 27 is a diagram of the tools used in sequence in the procedure of FIG. 25, applied to a "cross-joint" insertion of an anchor across a joint (essentially orthogonal to a "plane" of the cortical surfaces to be fixed with one another).

Referring to FIGS. 26 and 27, the two different types of orientations, alignments, or installation configurations of anchors (the cross configuration and the along inside configuration) are illustrated to show which, and in what order different instruments are implemented. FIG. 26 refers to an insertion in which the materials 14*a*, 14*b* straddle a joint 15. Typically, at some outer extremity of a joint 15 will be ligaments securing the bone 14*a* to the bone 14*b*. In this instance, the Jamshidi needle 80 is used followed by the K-wire 84, small dilator 100*a*, large dilator 100*b* as described hereinabove. At this point, the path is ready for an access portal 110 shown on the left in the step wise instrument flow, and shown on the right as inserted through the skin, fat, fascia, and other soft tissues to get to the joint 15 between the two bones 14*a*, 14*b*.

Subsequently, the drill 120 is employed to drill through the bone 14, followed by a reamer 130 in order to clear out loose cartilage, any other loose materials, as well as scoring or abrading part of the cortical bone if necessary. That is, for example, the reamer 130 may be as important as the drill 120, since the reamer 130 makes the path for the anchor 12 to pass. A broach 134 may be employed to cut a path into cortical bone for passage of the splines 20 of the anchor 12. Ultimately, the insertion tool 140 is employed in the working portal 110 to insert the anchor 12.

At any point before, after, or during insertion of the anchor 12, any significant spaces remaining may be filled with bone graft material, typically allograft, also called homograft. This typically includes small particles of bone to aid in the early healing and growth through any available spaces by natural bone. Following insertion of all anchors 12, the working portal 110 may be withdrawn, and proper suturing may be done to close the wound.

When inserting anchors 12 across through one bone 14 into another bone 14, the Jamshidi needle 80 begins the process, followed by insertion of a K-wire 84. A small dilator 100*a* may be implemented, but the twin may also be used at this point. However, it is more common that following insertion of the small dilator 100*a* in the process of FIG. 26 that a parallel path may be set up by twin dilators 100*b* following the path of a withdrawn small dilator 100*a*, while establishing the path of the twin small dilator 100*d* in parallel to the dilator 100*c*.

The large dilator 100*b* is thus passed over the small dilator 100*a*, followed by the working portal 110 being fitted over and forced into place. Again, the working portal 110 anchors to the bone 14 and the dilators 100*a*, 100*b* may be removed.

Accordingly, the drill 120 may be implemented as described hereinabove, followed by the broach 134. It is worth noting that broaching is optional, it is not always required. Nevertheless, due to the comparatively brittle cortical bone, meaning that cortical bone will fracture in response to force much more quickly than will cancellous bone or soft tissues, which may displace and even damage traumatically, but do not necessarily chip away as the conventional fracturing of cortical bone. Thus, the broach 134 has a very useful function, but in some instances may be unnecessary.

Of course the processes 150 may be repeated for multiple anchors 12 in multiple locations in an SI-joint fixation. Herein, a diameter of an anchor or any other article or component means the diameter of a circle circumscribing the anchor, other article, or component. Effective diameter means "hydraulic diameter," which is four times the cross-sectional area divided by the perimeter (typically called "wetted perimeter," the fluid contact perimeter when applied to a solid-fluid interface, interior or exterior to the solid). One will see that effective diameter becomes the regular diameter for a circular shape, and the length of a side for a square shape. For other shapes, especially irregular shapes, the effective diameter is some other value, but useful in various fluid-related calculations.

The present invention may be embodied in other specific forms without departing from its purposes, functions, structures, or operational characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by patent is:

1. A method for fixing a first bone to a second bone, the method comprising:

providing an anchor comprising a core, extending along an axis defining axial, radial, and circumferential directions, a plurality of splines, each spline a helix extending radially away from and axially along the core and having a hyper pitch, meaning a pitch length greater than a length of the anchor and exceeding at least two lengths of the anchor;

providing access to two bones, each presenting a cortical surface to be joined to the other; and penetrating, by the anchor, fixing each of the cortical surfaces in at least two degrees of freedom with respect to the other in response to engagement of each by the splines.

2. The method of claim 1, wherein penetrating is urged by forces including an impact load from a mallet.

3. The method of claim 1, wherein the two bones are a sacrum and an ilium.

4. The method of claim 1, wherein the splines progress helically, the anchor turning circumferentially with axial progression through or between the bones, in response to engagement of, by the plurality of splines, the cortical surfaces.

5. The method of claim 1, wherein the splines define a helical angle of progression, measured as an angular measure of rotation about the axis with respect to axial progression, severely acute about the axis, meaning less than 360 degrees divided by the number of splines.

6. The method of claim 1, wherein the access is provided by at least one of an incision, a dilation, insertion of a guide, reaming, broaching, installing a portal, and inserting tools along a guided path.

7. The method of claim 6, wherein the access is provided by a process including an incision, a dilation, insertion of a guide, installing a portal, and inserting tools through the portal.

8. The method of claim 6, comprising installing multiple anchors engaging the two bones, effecting fixation with respect to one another in six degrees of freedom.

9. The method of claim 1, wherein the anchor constitutes a first anchor, and another anchor is installed, constituting a second anchor, such that:

one of the first and second anchors crosses the cortical surfaces in a direction principally orthogonal to, meaning crossing through, both cortical surfaces; and the remaining one of the first and second anchors passes along a joint region between the cortical surfaces principally parallel to both cortical surfaces, meaning engaging the cortical surfaces by some of the splines extending tangent to the cortical surfaces while a majority of the remaining one of the first and second anchors remains between the cortical surfaces.

10. The method of claim 1, wherein:

the access is provided by a process including an incision, a dilation, insertion of a guide, installing an access portal, and inserting tools through the portal, and including;

a first anchor fixing the two bones against relative translation with respect to one another principally parallel to the cortical surfaces by crossing the cortical surfaces in a direction principally orthogonal to both, meaning penetrating each and their corresponding cancellous tissue; and a second anchor fixes the two bones against relative translation therebetween in a direction principally orthogonal to the cortical surfaces, meaning toward or away from each other, by passing along both of the cortical surfaces, between them, engaging each by multiple splines of the plurality of splines of the second anchor.

11. The method of claim 1, wherein:

the material of the anchor is selected from a metal, a polymer, a reinforced polymer, and bone; and the splines have a wedge angle, meaning an angle characterized by a right triangle in which a hypotenuse equals a helical distance along a spline and an opposite side equals one pitch distance, and a sine of the wedge angle is greater than a cosine thereof; and the method comprises:

providing access through soft tissue adjacent the first and second bones, exposing corresponding cortical surfaces to be joined, and piloting a path proximate the cortical surfaces, in a location characterized by one of 1) passing along the cortical surfaces, between and approximately in a direction that the cortical surfaces both extend, and 2) penetrating through, approximately normal to, each of the cortical surfaces.

12. The method of claim 1, wherein the anchor has a pitch angle less than 15 degrees, where the pitch angle is measured from a first plane through the axis and a base of the spline proximate a head end of the anchor to the spline unwrapped about a circumference thereof and placed onto a second plane orthogonal to the first plane and tangent to a core at the base of the spline.

13. The method of claim 12, wherein the pitch angle is less than 10 degrees, and a wedge angle is greater than 90 degrees, where the wedge angle is the angle whose sine is the pitch distance divided by a helical length of the splines at an outermost circumferential surface.

14. The method of claim 12, wherein the pitch is characterized by a swept angle less than 360 degrees divided by the number of splines, where the swept angle is measured between a first plane through the axis and a spline at its closest location proximate the head end, and a second plane through the axis and the spline at its closest location proximate the point end; and the method comprises inserting the anchor with an interference fit along a broached path axially centered about a guide wire.

15. A method for fixing a first bone to a second bone, the bones each comprising a cortical portion and a medullar portion, the method comprising:

selecting an anchor comprising a core, hollow inside with splines on an outside surface, the core extending along an axis, the axis defining axial, radial, and circumferential directions with respect thereto, and each one of the plurality of splines extending radially away from, and both axially and circumferentially, along the core as a helix of pitch length greater than a length of the core, measured axially, multiplied by the number of splines;

providing access to two bones, each presenting a cortical surface to be joined to the cortical surface of the other; and penetrating, by the anchor, fixing each of the cortical surfaces in at least one degree of freedom with respect to the other in response to engagement of each of the cortical portions by the splines.

16. The method of claim 15, comprising:

inserting a Jamshidi needle into flesh a distance to reach a first bone;

removing a trocar from within the Jamshidi needle;

inserting a guide of k-wire through the Jamshidi needle;

removing the Jamshidi Needle;

inserting through the flesh and along the guide a first dilator;

inserting through the flesh a second dilator having an inner diameter larger than an outer diameter of the first dilator;

inserting through the flesh and anchoring into at least one of the first and second bones a working portal having an inner diameter larger than an outer diameter of the second dilator;

removing the dilators;

determining a distance into the working portal;

creating a path by piloting a selected distance beyond the working portal; and fixing the first bone with respect to the second bone in at least two degrees of freedom by engaging the first and second bones by the splines of the anchor due to inserting the anchor along the path.

17. An apparatus comprising:

a head;

a point;

the head and the point each lying along a central axis defining a radial direction, proceeding orthogonally away therefrom, and a circumferential direction, circumscribing the central axis orthogonal to the radial direction throughout the length of the splines; and splines extending between the head and the point, each defining a helical direction progressing both axially along the central axis and radially away therefrom simultaneously at a pitch equal to multiple lengths of the anchor along the central axis.

18. The apparatus of claim 17, wherein the point is selected from a solid point, constituted by a convergence of the splines at a corresponding narrowing of a diameter of the apparatus, and a hollow point, constituted by a tubular structure from which the splines extend radially.

19. The apparatus of claim 18, wherein the tubular structure is provided with bone growth adherence structures selected from grow-through apertures in the splines, grow through apertures in the tubular structure, grow-on structures on the splines, and grow-on structures on the tubular structure.

20. The apparatus of claim 17, wherein the apparatus is formed of a porous material capable of fostering growth of bone material therethrough.

21. A method for fixing a first bone to a second bone, the method comprising:

providing an anchor comprising a core, extending along an axis defining axial, radial, and circumferential directions, a plurality of splines, each spline a helix extending radially away from and axially along the core and having a hyper pitch, meaning a pitch length greater than a maximum length of the anchor;

providing access to two bones, each presenting a cortical surface to be joined to the other, wherein the two bones are a sacrum and an ilium; and penetrating, by the anchor, fixing each of the cortical surfaces in at least two degrees of freedom with respect to the other in response to engagement of each by the splines.

22. A method for fixing a first bone to a second bone, the method comprising:

providing an anchor comprising a core, extending along an axis defining axial, radial, and circumferential directions, a plurality of splines, each spline a helix extending radially away from and axially along the core and having a hyper pitch, meaning a pitch length greater than a maximum length of the anchor, wherein the splines define a helical angle of progression, measured as an angular measure of rotation about the axis with respect to axial progression, severely acute about the axis, meaning less than 360 degrees divided by the number of splines;

providing access to two bones, each presenting a cortical surface to be joined to the other; and penetrating, by the anchor, fixing each of the cortical surfaces in at least two degrees of freedom with respect to the other in response to engagement of each by the splines.

23. A method for fixing a first bone to a second bone, the method comprising:

providing an anchor comprising a core, extending along an axis defining axial, radial, and circumferential directions, a plurality of splines, each spline a helix extending radially away from and axially along the core and having a hyper pitch, meaning a pitch length greater than a maximum length of the anchor;

providing access to two bones, each presenting a cortical surface to be joined to the other;

penetrating, by the anchor, fixing each of the cortical surfaces in at least two degrees of freedom with respect to the other in response to engagement of each by the splines;

wherein the anchor constitutes a first anchor, and another anchor is installed, constituting a second anchor, such that:

one of the first and second anchors crosses the cortical surfaces in a direction principally orthogonal to, meaning crossing through, both cortical surfaces; and the remaining one of the first and second anchors passes along a joint region between the cortical surfaces principally parallel to both cortical surfaces, meaning engaging the cortical surfaces by some of the splines extending tangent to the cortical surfaces while a majority of the remaining one of the first and second anchors remains between the cortical surfaces.

24. A method for fixing a first bone to a second bone, the method comprising:

providing an anchor comprising a core, extending along an axis defining axial, radial, and circumferential directions, a plurality of splines, each spline a helix extending radially away from and axially along the core and having a hyper pitch, meaning a pitch length greater than a maximum length of the anchor;

providing access to two bones, each presenting a cortical surface to be joined to the other;

penetrating, by the anchor, fixing each of the cortical surfaces in at least two degrees of freedom with respect to the other in response to engagement of each by the splines;

wherein the access is provided by a process including an incision, a dilation, insertion of a guide, installing an access portal, and inserting tools through the portal, and including;

a first anchor fixing the two bones against relative translation with respect to one another principally parallel to the cortical surfaces by crossing the cortical surfaces in a direction principally orthogonal to both, meaning penetrating each and their corresponding cancellous tissue; and a second anchor fixes the two bones against relative translation therebetween in a direction principally orthogonal to the cortical surfaces, meaning toward or away from each other, by passing along both of the cortical surfaces, between them, engaging each by multiple splines of the plurality of splines of the second anchor.

25. A method for fixing a first bone to a second bone, the method comprising:

providing an anchor comprising a core, extending along an axis defining axial, radial, and circumferential directions, a plurality of splines, each spline a helix extending radially away from and axially along the core and having a hyper pitch, meaning a pitch length greater than a maximum length of the anchor;

providing access to two bones, each presenting a cortical surface to be joined to the other;

penetrating, by the anchor, fixing each of the cortical surfaces in at least two degrees of freedom with respect to the other in response to engagement of each by the splines;

wherein the material of the anchor is selected from a metal, a polymer, a reinforced polymer, and bone; and the splines have a wedge angle, meaning an angle characterized by a right triangle in which a hypotenuse equals a helical distance along a spline and an opposite side equals one pitch distance, and a sine of the wedge angle is greater than a cosine thereof; and the method comprises:

providing access through soft tissue adjacent the first and second bones, exposing corresponding cortical surfaces to be joined, and piloting a path proximate the cortical surfaces, in a location characterized by one of 1) passing along the cortical surfaces, between and approximately in a direction that the cortical surfaces both extend, and 2) penetrating through, approximately normal to, each of the cortical surfaces.

26. A method for fixing a first bone to a second bone, the method comprising:

providing an anchor comprising a core, extending along an axis defining axial, radial, and circumferential directions, a plurality of splines, each spline a helix extending radially away from and axially along the core and having a hyper pitch, meaning a pitch length greater than a maximum length of the anchor;

providing access to two bones, each presenting a cortical surface to be joined to the other;

penetrating, by the anchor, fixing each of the cortical surfaces in at least two degrees of freedom with respect to the other in response to engagement of each by the splines;

wherein the anchor has a pitch angle less than 15 degrees, where the pitch angle is measured from a first plane through the axis and a base of the spline proximate a head end of the anchor to the spline unwrapped about a circumference thereof and placed onto a second plane orthogonal to the first plane and tangent to a core at the base of the spline.

27. A method for fixing a first bone to a second bone, the method comprising:

providing an anchor comprising a core, extending along an axis defining axial, radial, and circumferential directions, a plurality of splines, each spline a helix extending radially away from and axially along the core and having a hyper pitch, meaning a pitch length greater than a maximum length of the anchor;

providing access to two bones, each presenting a cortical surface to be joined to the other;

penetrating, by the anchor, fixing each of the cortical surfaces in at least two degrees of freedom with respect to the other in response to engagement of each by the splines;

wherein the pitch angle is less than 10 degrees, and a wedge angle is greater than 90 degrees, where the wedge angle is the angle whose sine is the pitch distance divided by a helical length of the splines at an outermost circumferential surface.

28. A method for fixing a first bone to a second bone, the method comprising:

providing an anchor comprising a core, extending along an axis defining axial, radial, and circumferential directions, a plurality of splines, each spline a helix extending radially away from and axially along the core and having a hyper pitch, meaning a pitch length greater than a maximum length of the anchor;

providing access to two bones, each presenting a cortical surface to be joined to the other;

penetrating, by the anchor, fixing each of the cortical surfaces in at least two degrees of freedom with respect to the other in response to engagement of each by the splines;

wherein the pitch is characterized by a swept angle less than 360 degrees divided by the number of splines, where the swept angle is measured between a first plane through the axis and a spline at its closest location proximate the head end, and a second plane through the axis and the spline at its closest location proximate the point end; and the method comprises inserting the anchor with an interference fit along a broached path axially centered about a guide wire.

* * * * *